United States Patent
Bratcher et al.

(10) Patent No.: US 7,048,211 B2
(45) Date of Patent: May 23, 2006

(54) FLEXIBLE PROCESSING APPARATUS FOR ISOLATING AND PURIFYING VIRUSES, SOLUBLE PROTEINS AND PEPTIDES FROM PLANT SOURCES

(75) Inventors: Barry Bratcher, Owensboro, KY (US); Stephen J. Garger, Vacaville, CA (US); R. Barry Holtz, Vacaville, CA (US); Michael J. McCulloch, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 10/781,448

(22) Filed: Feb. 18, 2004

(65) Prior Publication Data

US 2004/0166026 A1 Aug. 26, 2004

Related U.S. Application Data

(60) Division of application No. 09/970,150, filed on Oct. 3, 2001, which is a continuation of application No. 09/962,527, filed on Sep. 24, 2001, now Pat. No. 6,740,740, which is a continuation of application No. 09/466,422, filed on Dec. 17, 1999, now Pat. No. 6,303,779, which is a continuation of application No. 09/259,741, filed on Feb. 25, 1999, now Pat. No. 6,033,895, which is a division of application No. 09/037,751, filed on Mar. 10, 1998, now Pat. No. 6,037,456.

(51) Int. Cl.
*A61K 8/97* (2006.01)

(52) U.S. Cl. .............................. 241/2; 424/74

(58) Field of Classification Search .................... 241/2, 241/259; 424/74; 364/500; 700/10
See application file for complete search history.

(56) References Cited

U.S. PATENT DOCUMENTS

| 4,268,632 A | 5/1981 | Wildman et al. ............ 435/232 |
| 4,333,871 A | 6/1982 | De Jong ....................... 260/112 |
| 4,347,324 A | 8/1982 | Wildman et al. ............ 435/232 |
| 4,540,490 A | 9/1985 | Shibata et al. ............. 210/323.2 |
| 4,632,318 A | 12/1986 | Hyuga ........................... 241/37 |
| 4,907,167 A * | 3/1990 | Skeirik ......................... 700/10 |
| 4,941,484 A | 7/1990 | Clapp et al. ................. 131/297 |

(Continued)

OTHER PUBLICATIONS

New Riverside University Dictionary, [Published by The Riverside Publishing Company and Houghton Mifflin Company, One Beacon Street, Boston, Massachusetts, 02108, USA (1984)], p. 589.*

(Continued)

*Primary Examiner*—Derris Banks
*Assistant Examiner*—Jason Y. Pahng
(74) *Attorney, Agent, or Firm*—Waddey & Patterson, P.C.; Lucian Wayne Beavers

(57) ABSTRACT

A flexible automated apparatus for isolating and purifying viruses, proteins and peptides of interest from a plant material is disclosed, the apparatus being applicable for large scale purification and isolation of such substances from plant material. The flexible automated apparatus provides an efficient apparatus for isolating viruses, proteins and peptides of interest with little waste material. The automated apparatus for isolating viruses, proteins and peptides of interest includes a grinding apparatus for homogenizing a plant to produce a green juice, a means for adjusting the pH of and heating the green juice, a means for separating the target species, either virus or protein/peptide, from other components of the green juice by one or more cycles of centrifugation, resuspension, and ultrafiltration, and finally purifying virus particles by such procedure as PEG-precipitation or purifying proteins and peptides by such procedures as chromatography and/or salt precipitation.

6 Claims, 32 Drawing Sheets

U.S. PATENT DOCUMENTS

| | | | | |
|---|---|---|---|---|
| 4,966,576 | A | | 10/1990 | Schulz et al. .................. 494/56 |
| 5,121,757 | A | | 6/1992 | White et al. ................ 131/297 |
| 5,131,414 | A | | 7/1992 | Fagg et al. .................. 131/297 |
| 5,267,937 | A | | 12/1993 | Zettier et al. .................. 494/56 |
| 5,377,698 | A | | 1/1995 | Litzinger et al. ............ 131/370 |
| 5,647,429 | A | * | 7/1997 | Oktay et al. ............ 165/104.26 |
| 5,676,631 | A | | 10/1997 | Kunz et al. .................... 494/71 |
| 5,687,922 | A | * | 11/1997 | Takaoka ..................... 241/259 |
| 5,765,570 | A | | 6/1998 | Litzinger et al. ............ 131/370 |
| 5,795,477 | A | | 8/1998 | Herman et al. .......... 210/360.1 |
| 5,865,719 | A | | 2/1999 | Droste et al. .................. 494/27 |
| 5,899,845 | A | | 5/1999 | Kohlstette et al. ............ 494/37 |
| 5,993,795 | A | * | 11/1999 | Osawa et al. .................. 424/74 |
| 6,037,456 | A | | 3/2000 | Garger et al. ............... 530/412 |
| 6,083,293 | A | | 7/2000 | Bath ............................ 71/16 |
| 6,106,715 | A | | 8/2000 | Thalmann et al. ..... 210/321.83 |
| 2002/0088024 | A1 | | 7/2002 | Garger et al. |

OTHER PUBLICATIONS

Samuel Wildman, "An Alternate Use For Tobacco Agriculture: Proteins For Food Plus A Safer Smoking Material" in *Plants: The Potentials For Extracting Protein, Medicines And Other Useful Chemicals—Workshop Proceedings* (U.S. Congress, Office of Technology Assessment, OTA-BP-23, Washington, DC, Sep. 1983).

L. Jervis and W.S. Pierpoint (1989) Purification technologies for plant proteins, *Jour. Of Biotechnology* 11:161-198.

Lamsal et al., Separation of Protein Fractions in Alfalfa Juice: Effects of Some Pre-treatment Methods. TEKRAN. Published Sep. 6, 2002 by the United States Department of Agriculture Agricultural Research Service.

Project Progress Report—Chemical Efficiency of the Pilot Plant in Owensboro—Part IV; Author Jan Arnarp, Oct. 11, 1995.

FOU Report No. 96/01—Chemical Efficiency of the Pilot Plant in Owensboro—Part IV by Jan Arnarp, Aug. 29, 1996.

New Riverside University Dictionary, Published by The Riverside Publishing Company and Houghton Mifflin Company, One Beacon Street, Boston, MA 02108, USA (1984), p. 589.

Project Progress Report—Chemical Efficiency of the Pilot Plant in Owensboro—Part IV; Author Jan Arnarp, Oct. 11, 1995.

FOU Report No. 96/01—Chemical Efficiency of the Pilot Plant in Owensboro—Part IV, Author Jan Arnarp, Aug. 29, 1996.

* cited by examiner

FIG. 22

Recipe

Tabs: Heat Treatment | Centrifuge 1 | Centrifuge 2 | Ultrafiltration
Sub-tabs: Sol Prep | GJ Extract | GJ Extract | Ultrafiltration UltraFiltration

| Field | Value | Range |
|---|---|---|
| Temp. Setpoint for Hold Tube | Text1 | 0-202 C |
| Max Hold Time | Text1 | 0-4095 Min |
| Holding Tube Configuration | Hold Config A | |
| Agitator 103 Speed Output | Text1 | 0-100% |
| Agitator 110 Speed Output | Text1 | 0-100% |
| Green Juice Flow to Centrifuge 1 | Text1 | 0-303 lpm |
| Centrifuge 1 Shot Frequency | Text1 | 0-1500 Sec |
| Recipe Type | S1 | |
| Ideal pH in Tank 108 | Text1 | 0-1400pH |
| Agitator 108 Speed Output | Text1 | 0-100% |
| Agitator 202 Speed Output | Text1 | 0-100% |
| Centrifuge 2 Shot Frequency | Text1 | 0-1500 Sec |
| Tank 108 Initial Make-Up Water | Text1 | 0-4000 Liters |
| Tank 108 Fill Water % of GJ | Text1 | 0-100% |
| Green Juice Flow to Centrifuge 2 | Text1 | 0-303 lpm |

| Field | Value | Range |
|---|---|---|
| Water Flow To Disintegrator | Text1 | 0-30 lpm |
| Water Flow To Press | Text1 | 0-30 lpm |
| Agitator 101 Speed | Text1 | 0-100% |
| Tank 101 Mix Time | Text1 | 0-4095 Sec |
| Concentration of buffer | Text1 | 0-1000 grams/liter |
| Grinder 1 Speed | Text1 | 0-100% |
| Ideal pH In Tank 102 | Text1 | 0-1400pH |
| Agitator 102 Speed | Text1 | 0-100% |
| Pump 102 Flow Rate | Text1 | 0-303 lpm |

Buttons: Save | Save As | Delete | Exit

FLEXIBLE PROCESSING APPARATUS FOR ISOLATING AND PURIFYING VIRUSES, SOLUBLE PROTEINS AND PEPTIDES FROM PLANT SOURCES

This application is a divisional of Ser. No. 09/970,150 filed Oct. 3, 2001, which is a continuation of U.S. patent application Ser. No. 09/962,527, filed Sep. 24, 2001 now U.S. Pat. No. 6,740,740, which is a continuation of U.S. patent application Ser. No. 09/466,422, filed Dec. 17, 1999 now U.S. Pat. No. 6,303,779, which is a continuation of U.S. patent application Ser. No. 09/259,741, filed Feb. 25, 1999 (now U.S. Pat. No. 6,033,895), which is a division of U.S. patent application Ser. No. 09/037,751, filed on Mar. 10, 1998 (now U.S. Pat. No. 6,037,456).

BACKGROUND OF THE INVENTION

1. Field of the Invention

The invention relates to a flexible automated processing apparatus for isolation and purification of biological material from plant sources.

2. Description of Related Art

Plant proteins and enzymes have long been exploited for many purposes, from viable food sources to biocatalytic reagents or therapeutic agents. During the past decade, the development of transgenic and transfected plants and improvement in genetic analysis have brought renewed scientific significance and economical incentives to these applications. The concepts of molecular plant breeding and molecular plant farming, wherein a plant system is used as a bioreactor to produce recombinant bioactive materials, have received great attention.

Many examples in the literature have demonstrated the utilization of plants or cultured plant cells to produce active mammalian proteins, enzymes, vaccines, antibodies, peptides, and other bioactive species. Ma et al. (Science 268: 716–719 (1995)) were the first to describe the production of a functional secretory immunoglobulin in transgenic tobacco. Genes encoding the heavy and light chains of murine antibody, a murine joining chain, and a rabbit secretory component were introduced into separate transgenic plants. Through cross-pollination, plants were obtained to co-express all components and produce a functionally active secretory antibody. In another study, a method for producing antiviral vaccines by expressing a viral protein in transgenic plants was described (Mason et al., Proc. Natl. Acad. Sci. USA 93: 5335–5340 (1996)). The capsid protein of Norwalk virus, a virus causing epidemic acute gastroenteritis in humans was shown to self-assemble into virus-like particles when expressed in transgenic tobacco and potato. Both purified virus-like particles and transgenic potato tubers when fed to mice stimulated the production of antibodies against the Norwalk virus capsid protein. Alternatively, the production and purification of a vaccine may be facilitated by engineering a plant virus that carries a mammalian pathogen epitope. By using a plant virus, the accidental shedding of virulent virus with the vaccine is abolished, and the same plant virus may be used to vaccinate several hosts. For example, malarial epitopes have been presented on the surface of recombinant tobacco mosaic virus (TMV) (Turpen et al. BioTechnology 13:53–57 (1995)). Selected B-cell epitopes were either inserted into the surface loop region of the TMV coat protein or fused into the C terminus. Tobacco plants after infection contain high titers of the recombinant virus, which may be developed as vaccine subunits and readily scaled up. In another study aimed at improving the nutritional status of pasture legumes, a sulfur-rich seed albumin from sunflower was expressed in the leaves of transgenic subterranean clover (Khan et al Transgenic Res. 5:178–185 (1996)). By targeting the recombinant protein to the endoplasmic reticulum of the transgenic plant leaf cells, an accumulation of transgenic sunflower seed albumin up to 1.3% of the total extractable protein could be achieved.

Work has also been conducted in the area of developing suitable vectors for expressing foreign genetic material in plant hosts. Ahlquist, U.S. Pat. No. 4,885,248 and U.S. Pat. No. 5,173,410 describe preliminary work done in devising transfer vectors which might be useful in transferring foreign genetic material into plant host cells for the purpose of expression therein. Additional aspects of hybrid RNA viruses and RNA transformation vectors are described by Ahlquist et al in U.S. Pat. Nos. 5,466,788, 5,602,242, 5,627,060 and 5,500,360 all of which are herein incorporated by reference. Donson et al, U.S. Pat. No. 5,316,931 and U.S. Pat. No. 5,589,367, herein incorporated by reference, demonstrate for the first time plant viral vectors suitable for the systemic expression of foreign genetic material in plants. Donson et al. describe plant viral vectors having heterologous subgenomic promoters for the systemic expression of foreign genes. The availability of such recombinant plant viral vectors makes it feasible to produce proteins and peptides of interest recombinantly in plant hosts.

Elaborate methods of plant genetics are being developed at a rapid rate and hold the promise of allowing the transformation of virtually every plant species and the expression of a large variety of genes. However, in order for plant-based molecular breeding and farming to gain widespread acceptance in commercial areas, it is necessary to develop a cost-effective and large-scale purification system for the bioactive species produced in the plants, either proteins or peptides, especially recombinant proteins or peptides, or virus particles, especially genetically engineered viruses.

Some processes for isolating proteins, peptides and viruses from plants have been described in the literature (Johal, U.S. Pat. No. 4,400,471, Johal, U.S. Pat. No. 4,334,024, Wildman et al., U.S. Pat. No. 4,268,632, Wildman et al., U.S. Pat. No. 4,289,147, Wildman et al., U.S. Pat. No. 4,347,324, Hollo et al., U.S. Pat. No. 3,637,396, Koch, U.S. Pat. No. 4,233,210, and Koch, U.S. Pat. No. 4,250,197, the disclosure of which are herein incorporated by reference). The succulent leaves of plants, such as tobacco, spinach, soybean, and alfalfa, are typically composed of 10–20% solids, the remaining fraction being water. The solid portion is composed of a water soluble and a water insoluble portion, the latter being predominantly composed of the fibrous structural material of the leaf. The water soluble portion includes compounds of relatively low molecular weight (MW), such as sugars, vitamins, alkaloids, flavors, amino acids, and other compounds of relatively high MW, such as native and recombinant proteins.

Proteins in the soluble portion of plant biomass can be further divided into two fractions. One fraction comprises predominantly a photosynthetic protein, ribulose 1,5-diphosphate carboxylase (or RuBisCO), whose molecular weight is about 550 kD. This fraction is commonly referred to as "Fraction 1 protein." RuBisCO is abundant, comprising up to 25% of the total protein content of a leaf and up to 10% of the solid matter of a leaf. The other fraction contains a mixture of proteins and peptides whose subunit molecular weights typically range from about 3 kD to 100 kD and other compounds including sugars, vitamins, alkaloids, flavors, amino acids. This fraction is collectively referred to as "Fraction 2 proteins." Fraction 2 proteins can be native host materials or recombinant materials including proteins and peptides produced via transfection or transgenic transformation. Transfected plants may also contain virus particles having a molecular size greater than 1,000 kD.

The basic process for isolating plant proteins generally begins with disintegrating leaf biomass and pressing the resulting pulp to produce "green juice". The process is typically performed in the presence of a reducing agent or antioxidant to suppress unwanted oxidation. The green juice, which contains various protein components and finely particulate green pigmented material, is pH adjusted and heated. The typical pH range for the green juice after adjustment is between 5.3 and 6.0. This range has been optimized for the isolation of Fraction 1 protein (or ribulose 1,5-diphosphate carboxylase). Heating, which causes the coagulation of green pigmented material, is typically controlled near 50° C. The coagulated green pigmented material can then be removed by moderate centrifugation to yield "brown juice." The brown juice is subsequently cooled and stored at a temperature at or below room temperature. After an extended period of time, e.g. 24 hours, ribulose 1,5-diphosphate carboxylase is crystallized from the brown juice. The crystallized Fraction 1 protein can subsequently be separated from the liquid by centrifugation. Fraction 2 proteins remain in the liquid, and they can be purified upon further acidification to a pH near 4.5. Alternatively, the crystal formation of ribulose 1,5-diphosphate carboxylase from brown juice can be effected by adding sufficient quantities of polyethylene glycol (PEG) in lieu of cooling.

The basic process for isolating virus particles is described in Gooding et al. Phytopathological Notes 57:1285 (1967), the teaching of which are herein incorporated by reference). To purify Tobacco Mosaic Virus (TMV) from plant sources in large quantities, infected leaves are homogenized and n-butanol is then added. The mixture is then centrifuged, and the virus is retained in the supernatant. Polyethylene glycol (PEG) is then added to the supernatant followed by centrifugation. The virus can be recovered from the resultant PEG pellet. The virus can be further purified by another cycle of resuspension, centrifugation and PEG-precipitation.

Existing protocols for isolating and purifying plant viruses and soluble proteins and peptides, however, present many problems. First, protein isolation from plant sources have been designed in large part for the recovery of Fraction 1 protein, not for other biologically active soluble protein components. The prior processes for large-scale extraction of $F_1$ proteins was for production of protein as an additive to animal feed or other nutritional substances. Acid-precipitation to obtain Fraction 2 proteins in the prior art is not effective, since most proteins denature in the pellet form. This is especially troublesome for isolating proteins and peptides produced by recombinant nucleic acid technology, as they may be more sensitive to being denatured upon acid-precipitation. Second, the existing methods of separation rely upon the use of solvents, such as n-butanol, chloroform, or carbon tetrachloride to eliminate chloroplast membrane fragments, pigments and other host related materials. Although useful and effective for small-scale virus purification, using solvents in a large-scale purification is problematic. Such problems as solvent disposal, special equipment designs compatible with flammable liquids. facility venting, and worker exposure protection and monitoring are frequently encountered. There are non-solvent based small-scale virus purification methods but these are not practical for large scale commercial operations due to equipment and processing limitations and final product purity (Brakke Adv. Virus Res. 7:193–224 (1960) and Brakke et al. Virology 39: 516–533(1969)). Finally, the existing protocols do not allow a streamline operation such that the isolation and purification of different viruses, virus-like particles, proteins and peptides can be achieved with minimum modification of a general purification procedure.

There is a need in the art for an efficient, non-denaturing and solvent-limited large-scale method and apparatus for virus and soluble protein isolation and purification. This need is especially apparent in cases where proteins and peptides produced recombinantly in plant hosts are to be isolated. The properties of these proteins and peptides are frequently different from those of the native plant proteins. Prior art protocols are not suitable to isolate recombinant proteins and peptides of interest. In addition, the vast diversity of recombinant proteins and peptides from plants and the stringent purity requirement for these proteins and peptides in industrial and medical application requires an efficient and economical procedure for isolating and purifying them. Efficient virus isolation is also of great importance because of the utility of viruses as transfection vectors and vaccines. In some situations, proteins and peptides of interest may be attached to a virus or integrated with native viral proteins (fusion protein), such that isolating the protein or peptide of interest may in fact comprise isolating the virus itself.

There is a need for apparatus that efficiently performs virus or protein isolation from mass quantities of plant material without negatively impacting the environment. In order to be cost effective, such apparatus needs to be capable of processing large quantities of plant bio-matter. Where the virus or protein isolated is intended for production as a pharmaceutical product, consistent and verifiable methodology is required. Therefore, there is a need for automated apparatus for isolating virus or proteins where the automated apparatus monitors and provides verification of methodology used in the isolation process.

SUMMARY OF THE INVENTION

The present invention relates to an automated processing apparatus for isolating and purifying viruses, proteins and peptides of interest from a plant host, applicable on a large scale. Moreover, the present invention provides an efficient and flexible system for isolating a variety of viruses, proteins and peptides of interest.

In general, the present invention includes an automated processing apparatus that includes a means for homogenizing bio-matter, a means for adjusting pH of juice of homogenized bio-matter, a means for heating the juice of homogenized bio-matter to a predetermined temperature for a predetermined length of time, a means for centrifuging the heat treated juice of homogenized bio-matter to separate pellet from supernatant, and a computer connected to each of the above means, the computer for monitoring and controlling the automated processing apparatus.

The computer controlled automated processing apparatus provides a reliable and reproducible way of extracting material of interest from plant material. In cases where the material of interest is intended for pharmaceutical uses, reliable and reproducible processing is highly advantageous. Further, the computer includes memory, storage and outputting means (i.e., a printer) thereby providing a permanent record of all processing related information.

The invention also relates to a computer for controlling an automated processing apparatus for processing bio-matter. The computer includes a monitor for displaying information, memory for storing collected data, means for inputting data, and means for outputting data. The computer is further connected to, for control and operation of the following: motors within a means for homogenizing bio-matter; means for adjusting pH of juice of homogenized bio-matter; means for heating the juice of homogenized bio-matter to a predetermined temperature for a predetermined length of time; and means for centrifuging the heat treated juice of homogenized bio-matter to separate pellet from supernatant.

The computer of the present invention reduces human intervention by directly controlling a variety of devices in the automated processing apparatus. The operation is more reliable and tracked by the computer in order to produce a permanent record of the processing steps.

The invention also relates to an automated computer controlled method for obtaining a virus from a plant. The method includes various steps such as having the computer control homogenization of a plant to produce a green juice homogenate. The computer also controls, monitors and adjustment of pH of the green juice homogenate to a first predetermined pH level. Thereafter, the computer controls heating of the green juice homogenate to a predetermined temperature. The computer controls centrifuging of the green juice homogenate to produce a pellet and also controls re-suspension of the pellet in a liquid solution. The computer also adjusts the pH of the liquid solution containing the re-suspended pellet to a predetermined second pH level. The method also includes having the computer control centrifuging the liquid solution containing the re-suspended pellet to produce a supernatant. As well, the method includes having a computer control an ultrafiltration apparatus for purifying the virus from the supernatant.

The present invention further relates to an automated plant processing apparatus that includes a first grinder for grinding plant material, a second grinder for further grinding of the plant material, and a press for separating solids and liquid from the ground plant material. The automated plant processing apparatus further includes a computer connected to the first grinder, the second grinder and the press for control thereof.

The computer is further connected to a plurality of further devices for further processing of the liquid extracted by the press. For instance, the computer is connected to and controls a pH adjusting tank that holds the extracted liquid. Sensors on and about the tank are connected to the computer enabling the computer to sense the pH condition of the liquid and add pH adjusting material as necessary to the tank. The computer is further connected to temperature sensors in both a heater and a cooler. Liquid flows through the heater and cooler after the pH is adjusted in the tank.

After heating and cooling, the pH adjusted liquid is fed into a second tank. The second tank includes a plurality of sensors that are also connected to the computer such that the condition and level of the liquid in the second tank is monitored by the computer. The computer further controls a first centrifuge downstream of the second tank. Flow of liquid into the first centrifuge is controlled by the computer such that supernatant S1 and pellet P1 are separated by the first centrifuge.

The computer is further connected to a third tank and a second centrifuge for further processing of the pellet P1. The third tank is provided with sensors connected to the computer for sensing the pH of the pellet P1 and a liquid providing valve such that the pellet P1 is re-suspended to release more of the material of interest. The computer controls introduction of pH adjusting material into the third tank to effect the re-suspension of the material of interest in the pellet P1. The computer further controls the introduction of the re-suspended pellet P1 into the second centrifuge for separation of waste pellet from a supernatant S2.

These and other objects, features, aspects and advantages of the present invention will become readily apparent to those skilled in the art from the following detailed description, which, taken in conjunction with the annexed drawings, discloses a preferred embodiment of the present invention.

BRIEF DESCRIPTION OF THE FIGURES

FIG. 1 is a flowchart that is divided into FIG. 1A and FIG. 1B showing an example of steps for isolating and purifying viruses and soluble proteins and peptides from plant sources in accordance with the present invention;

FIG. 2 is a perspective schematic view of an automated processing apparatus that includes a plurality of computer controlled devices that extract material of interest from plant sources in accordance with the present invention;

FIG. 3 is a side view, part elevation and part cutaway, of a grinder and press apparatus of the automated processing apparatus depicted in FIG. 2, in accordance with the present invention;

FIG. 4 is a cutaway perspective view of a first grinder of the grinder and press apparatus depicted in FIG. 3, in accordance with the present invention;

FIG. 5 is a cutaway perspective view of a second grinder of the grinder and press apparatus depicted in FIG. 3, in accordance with the present invention;

FIG. 6 is an end view of the grinder and press apparatus of FIG. 3, shown with a conveyer and a dryer device of the automated processing apparatus in accordance with the present invention;

FIG. 7 is a side view of the dryer device depicted in FIG. 6, in accordance with the present invention;

FIG. 8 is a side view of a pH adjuster tank of the automated processing apparatus depicted in FIG. 2, in accordance with the present invention;

FIG. 9 is a schematic side view of a heater of the automated processing apparatus depicted in FIG. 2, the heater for heating green juice extracted by the grinder and press apparatus in accordance with the present invention;

FIG. 10 is a side view of an insulated pipe assembly of the automated processing apparatus depicted in FIG. 2, with insulation shown fragmentarily in a cross-section, the insulated pipe assembly for maintaining the green juice at a predetermined temperature for a predetermined period of time in accordance with the present invention;

FIG. 11 is a side view of coolers of the automated processing apparatus depicted in FIG. 2. the coolers for cooling the green juice retained in the pipe assembly depicted in FIG. 10, in accordance with the present invention;

FIG. 12 is a side cutaway view of a tank and re-circulation system of the automated processing apparatus depicted in FIG. 2, in accordance with the present invention;

FIG. 13 is a schematic side view of a centrifuge of the automated processing apparatus depicted in FIG. 2, the centrifuge shown in a liquid extraction mode, in accordance with the present invention;

FIG. 14 is another schematic side view of the centrifuge depicted in FIG. 13, shown in a pellet expulsion mode, in accordance with the present invention;

FIG. 15 is a schematic chart showing operative connections between each of the various devices of the automated processing apparatus depicted in FIG. 2, in accordance with the present invention;

FIG. 22 is a representation of a Recipe screen displayed on the computer depicted in FIG. 19, utilized in the automated control of the automated processing apparatus depicted in FIG. 2, in accordance with the present invention.

Figure 2:
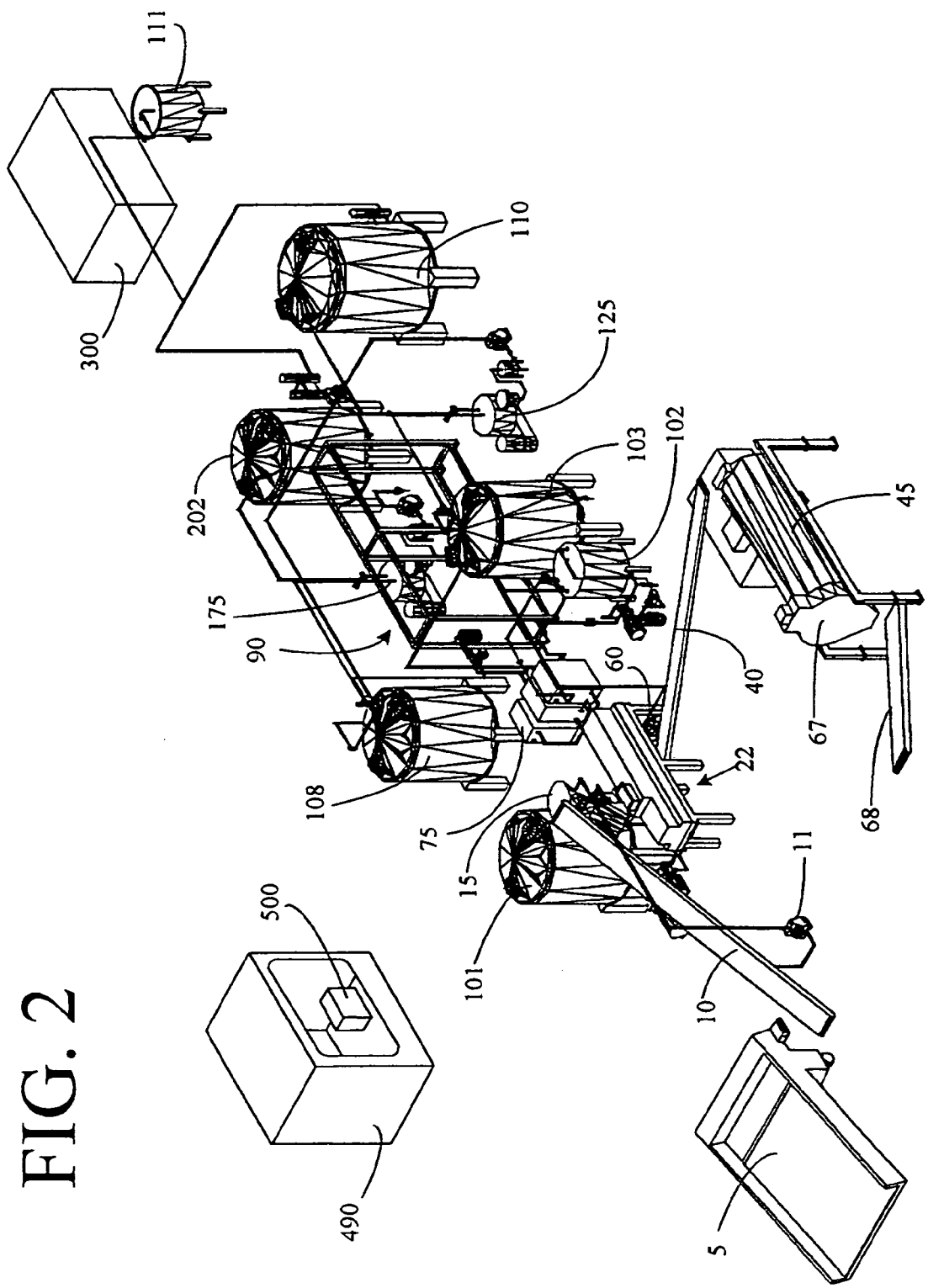
Figure 19A:
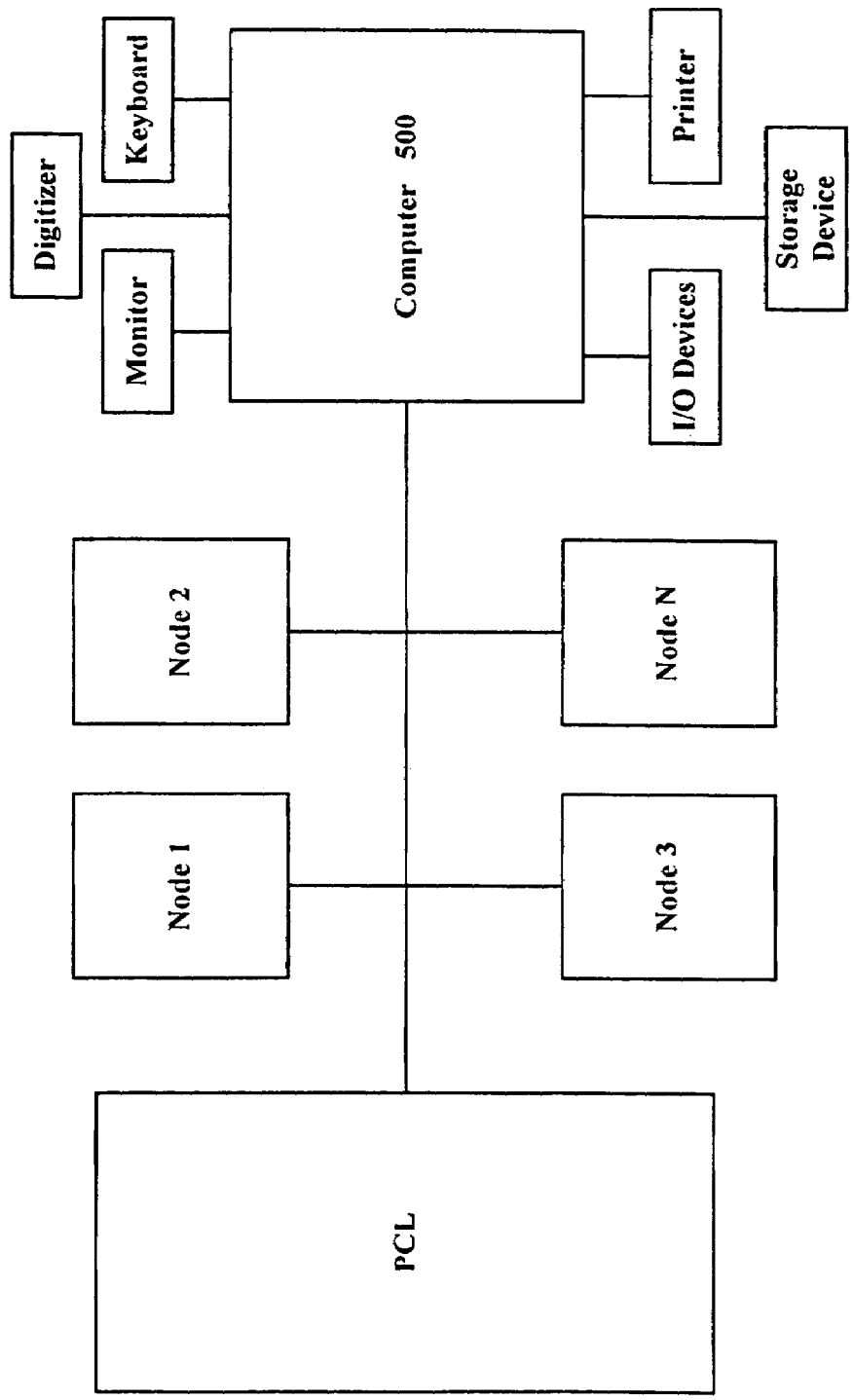
FIG. 19A is a block diagram showing schematically a computer and a programmed logic controller (PLC) of the automated processing apparatus of the present invention.
Figure 19B:
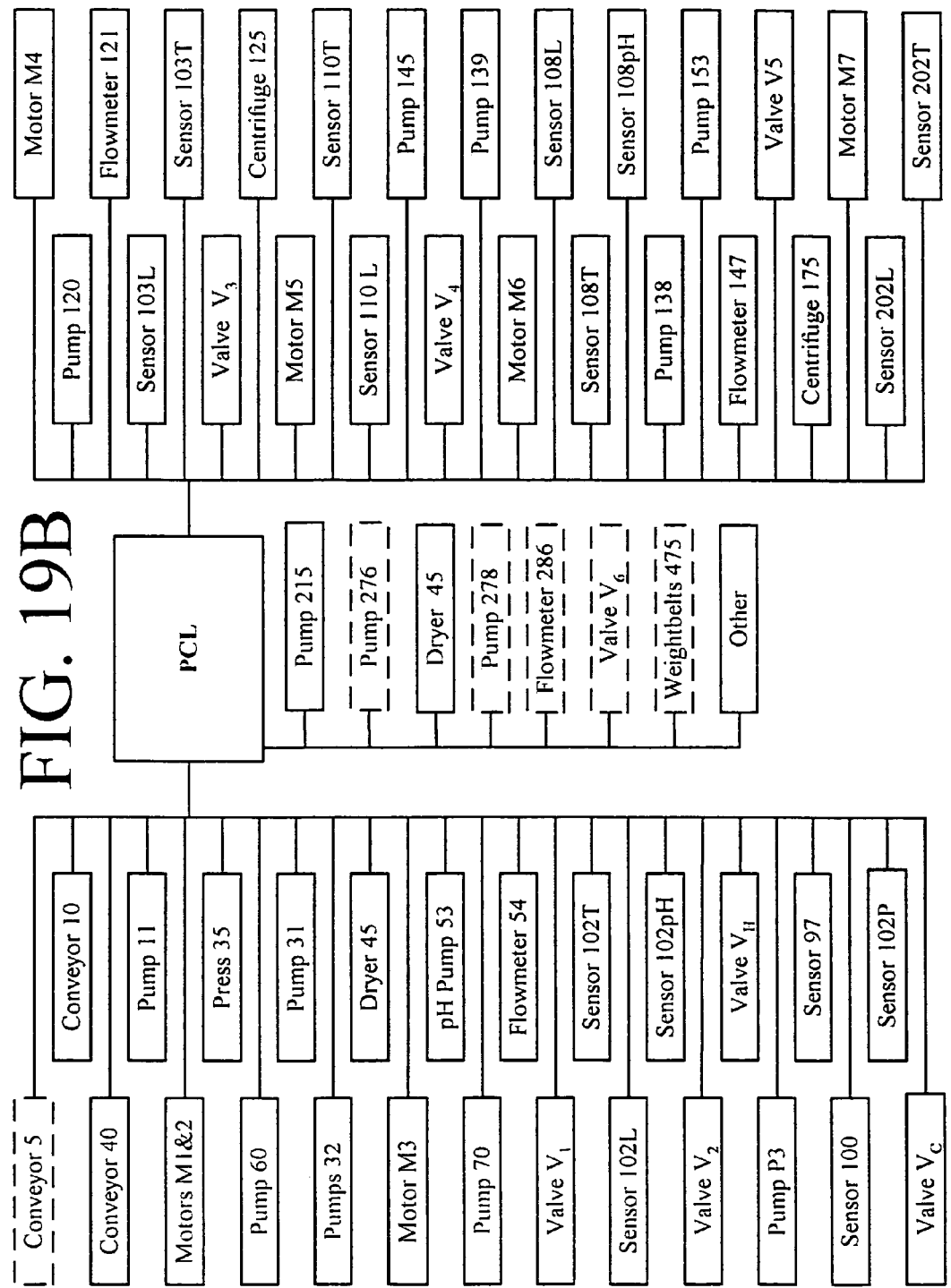
FIG. 19B is a block diagram showing schematically connections between the PLC and various sensors, motor, valves and pumps of the automated processing apparatus depicted in FIG. 2, in accordance with the present invention.
Figure 29:
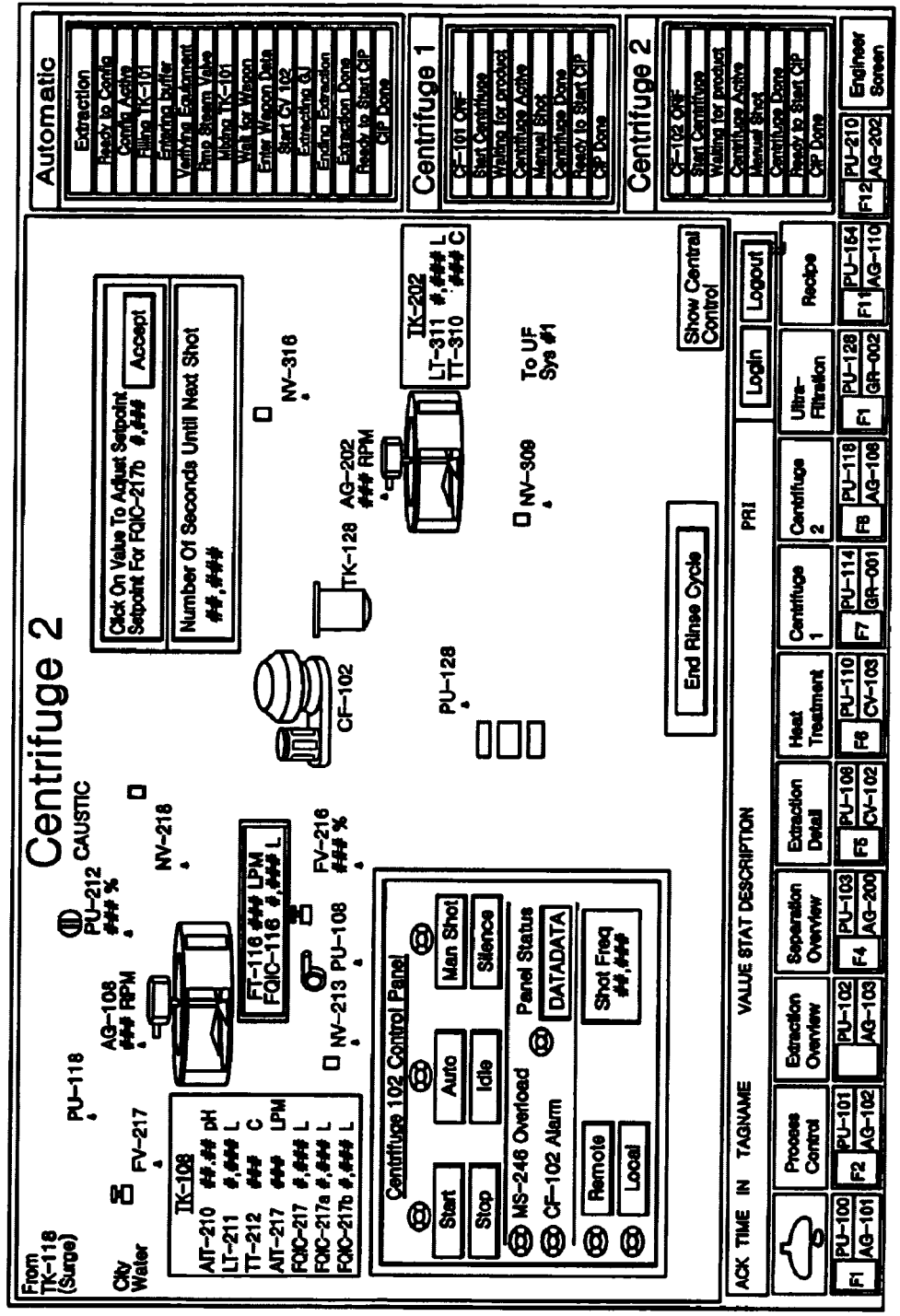
Figure 30:
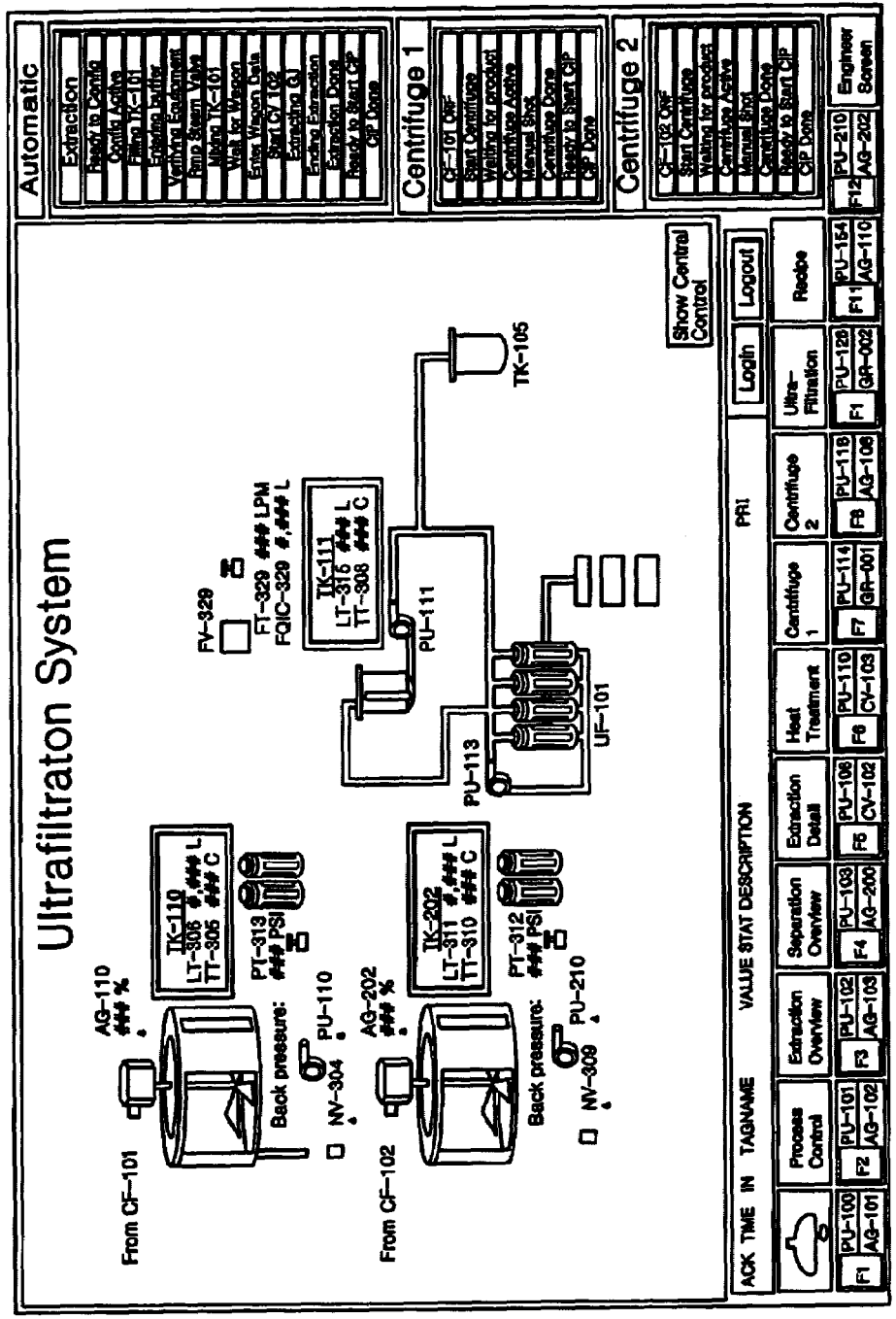

FIG. 29 is a representation of a centrifuge 2 screen displayed on the computer depicted in FIG. 19, utilized in the automated control of the automated processing apparatus depicted in FIG. 2, in accordance with the present invention; and FIG. 30 is a representation of an ultrafiltration system screen displayed on the computer depicted in FIG. 19, utilized in the automated control of the automated processing apparatus depicted in FIG. 2, in accordance with the present invention.

DETAILED DESCRIPTION OF THE INVENTION

The present invention features a novel automated processing apparatus for isolating and purifying viruses, proteins, virus-like particles and peptides and soluble components, sugars etc., of interest from a plant host. Moreover, the present invention provides a more efficient and environmentally safe processing apparatus for isolating viruses, proteins and peptides of interest than those methods and apparatus described in the prior art. In addition, the present invention is applicable for large scale production, where the term large scale production refers to processing large quantities of a bio-mass on a mass production level.

In general, the present automated processing apparatus for isolating viruses, proteins and peptides of interest comprises a plurality of computer controlled devices and apparatuses that are configured for homogenizing plant material to produce a green juice and remove fibrous material from the plant material, adjusting the pH of the green juice, heating the green juice, and separating from other components of the green juice by one or more cycles of centrifugation. Thereafter, the resulting juice having virus particles or desired protein(s) of interest is filtered and subjected to ultrafiltration to produce a concentrated juice. The concentrated juice may further be purified by such procedure as PEG-precipitation or purifying proteins and peptides by such procedures as chromatography, including affinity separation, and/or salt precipitation.

The automated processing apparatus of the present invention is configured to perform various processing steps, including methods for isolating viruses, proteins and peptides of interest in accordance with the methods disclosed in co-pending U.S. application Ser. No. 09/259,741 which is a division of U.S. application Ser. No. 09/037,751, filed on Mar. 10, 1998, now U.S. Pat. No. 6,037,456. U.S. application Ser. No. 09/259,741 is incorporated herein by reference in its entirety. Further, U.S. application Ser. No. 09/037,751, filed on Mar. 10, 1998, now U.S. Pat. No. 6,037,456 is also incorporated herein by reference in its entirety.

It should be understood from the following description that the automated processing system of the present invention is a flexible system that may also be used to process plant material in a manner that differs from the methods disclosed in the co-pending application and issued patent mentioned above. For instance, it should be understood that the automated processing apparatus described below may be used to process bio-matter and plant material using methods that differ from those disclosed in co-pending U.S. application Ser. No. 09/259,741, by changing, for instance, grinder and press apparatus configuration (described in greater detail below), the pH settings of the pH adjuster portion (described below) of the automated processing apparatus, centrifugation parameters and/or the filtration parameters (also described below). Other parameters, such as the temperature and duration of heating of processed extracted juice (green juice) may also be altered. Other alterations of the described processes may be adjusted as will be apparent to one of ordinary skill in the art.

Definitions

In order to provide a clear and consistent understanding of the specification and the claims, including the scope given herein to such terms, the following definitions are provided:

In the following description, the terms "bio-mass", "bio-matter" and "plant source" all refer to any harvested plant, seed or portion of a plant that may be processed to extract or isolate material of interest such as viruses, proteins and/or peptides therefrom. For instance, as is described in U.S. Pat. No. 6,037,456 and in co-pending U.S. application Ser. No. 09/259,741, bio-matter or plant material may include tobacco plants that have been infected with a manipulated tobacco mosaic virus. Alternatively, other plants such as corn, rice, grains or other desirable plants may be processed using the automated processing apparatus in accordance with the present invention to isolate viruses, proteins and peptides of interest, that may be contained in such bio-matter. Further the bio-matter process may include many types of plants or portions of plants such as seeds, flowers, stalks, stems, roots, tuber, as well as leaf portions of plant material.

The term "green juice" refers to liquid extracted from processed bio-matter by the automated processing apparatus of the present invention. However, it should be understood that the term green juice may refer to any liquid extracted from a plant material or bio-matter regardless of the extracted liquid's color.

A "virus" is defined herein to include the group consisting of: a virion wherein the virion includes an infectious nucleic acid sequence in combination with one or more viral structural proteins; a non-infectious virion wherein the non-infectious virion includes a non-infectious nucleic acid in combination with one or more viral structural proteins; and aggregates of viral structural proteins wherein there is no nucleic acid sequence present or in combination with the aggregate and wherein the aggregate may include virus-like particles (VLPs). The viruses may be either naturally occurring or derived from recombinant nucleic acid techniques and include any viral-derived nucleic acids that can be adopted whether by design or selection, for replication in whole plants, plant tissues or plant cells.

A "virus population" is defined herein to include one or more viruses as defined above wherein the virus population consists of a homogenous selection of viruses or wherein the virus population consists of a heterogenous selection including any combination and proportion of the viruses.

"Virus-like particles" (VLPs) are defined herein as self-assembling structural proteins wherein the structural proteins are encoded by one or more nucleic acid sequences wherein the nucleic acid sequence(s) is inserted into the genome of a host viral vector.

"Protein and peptides" are defined as being either naturally-occurring proteins and peptides or recombinant proteins and peptides produced via transfection or transgenic transformation.

The terms "material of interest" and "materials of interest" refer to any material, compound, organic structure or combination of materials to be isolated using the automated processing apparatus in accordance with the present invention. The material or materials of interest may include, but are not limited to: virons, virus-like particles viruses, proteins and/or peptides, receptors, receptor antagonists, antibodies, single-chain antibodies, enzymes, neuropolypeptides, insulin, antigens, vaccines, peptide hormones, calcitonin, and human growth hormone. Further, the material or materials of interest may be an antimicrobial peptide or protein consisting of protegrins, magainins, cecropins, melittins, indolicidins, defensins, β-defensins, cryptdins, clavainins, plant defensins, nicin and bactenecins. Virus can include, for instance, TMV-based viruses. Other virus of interest may be a polyvirus, a tobamovirus, a bromovirus, a carmovirus, a luteovirus, a marafivirus, the MCDV group, a necrovirus, the PYFV group, a sobemovirus, a tombusvirus, a tymovirus, a capillovirus, a closterovirus, a carlavirus, a potexvirus, a comovirus, a dianthovirus, a fabavirus, a nepovirus, a PEMV, a furovirus, a tobravirus, an AMV, a tenuivirus, a rice necrosis virus, caulimovirus, a geminivirus, a reovirus, the commelina yellow mottle virus group and a cryptovirus, a Rhabdovirus, or a Bunyavirus.

An illustration of one possible set of processing steps performed by the automated processing apparatus of the present invention is presented in FIG. 1. These steps relate generally to, for instance, a process for extracting protein and or virus material from tobacco and represent only one possible application of the automated processing apparatus of present invention. It should be understood that the steps shown in FIG. 1 are intended merely to visualize one possible combination of steps performed by the present invention and are not to be construed as being limiting to the procedures or orders of their appearances depicted therein. Any modifications to the instant invention which are functionally equivalent to the procedures and conditions disclosed herein are within the scope of the instant invention. Further, it should be understood that the various devices and apparatus utilized in the automated processing apparatus of the present invention may be utilized in a variety of processing operations, not just the steps depicted in FIG. 1.

The various steps depicted in FIG. 1 are explained in greater detail below. Thereafter follows a description of the various apparatuses that make up the automated processing apparatus of the present invention.

FIG. 2 is a perspective view of the automated processing apparatus for processing bio-matter in accordance with one embodiment of the present invention. In the opening description that follows of processes for extracting virus and, or proteins from bio-matter shown in FIG. 1, reference is made to several devices depicted in FIG. 2 and other drawings. A detailed description of each depicted device and controlling computer follows the opening description of the various processes.

Homogenization

The following processing steps are, in general, typical processing steps that the automated processing apparatus of the present invention is adapted to perform. The initial step of the present invention includes homogenizing the subject plant (see (A) in FIG. 1). In the present invention, a grinder and press apparatus 22 (see FIGS. 2, 3, 4 and 5) is used to homogenize bio-matter to remove green juice from plant pulp. The homogenizing step may optionally be performed in the presence of a suitable reducing agent or oxidizing agent, such as sodium metabisulfite ($Na_2S_2O_5$), to suppress unwanted oxidation.

The grinder and press apparatus 22 homogenizes the bio-matter producing green juice and removing unwanted pulp. The subsequent steps to isolate and purify viruses and soluble proteins/peptides may be performed generally according to the following procedures.

pH Adjustment and Heat Treatment of Green Juice

In this example of an application of the automated processing apparatus of the present invention, after homogenization, the pH of the initial green juice is adjusted (see (B) in FIG. 1) to a value of, for instance, between about 4.0 and 5.2 in a tank 102 depicted in FIG. 8 (and described later below). Thereafter, the green juice is heated to a temperature of between about 45–50° C. for a minimum of one minute. In some usages of the present invention, heat treatment may be adjusted to last between 10 to 15 minutes or longer. Those skilled in the art will readily appreciate that the time allocated for heat treatment will vary depending on the recovery of the desired species. Therefore, following pH adjustment, the heating time may vary from about one minute to over 15 minutes. Those skilled in the art will appreciate that pH may be adjusted using many suitable acids or bases well known in the art. The pH of green juice influences the distribution of virus, proteins and peptides in the supernatant S1 or pellet P1 during subsequent centrifugations.

Figure 9:
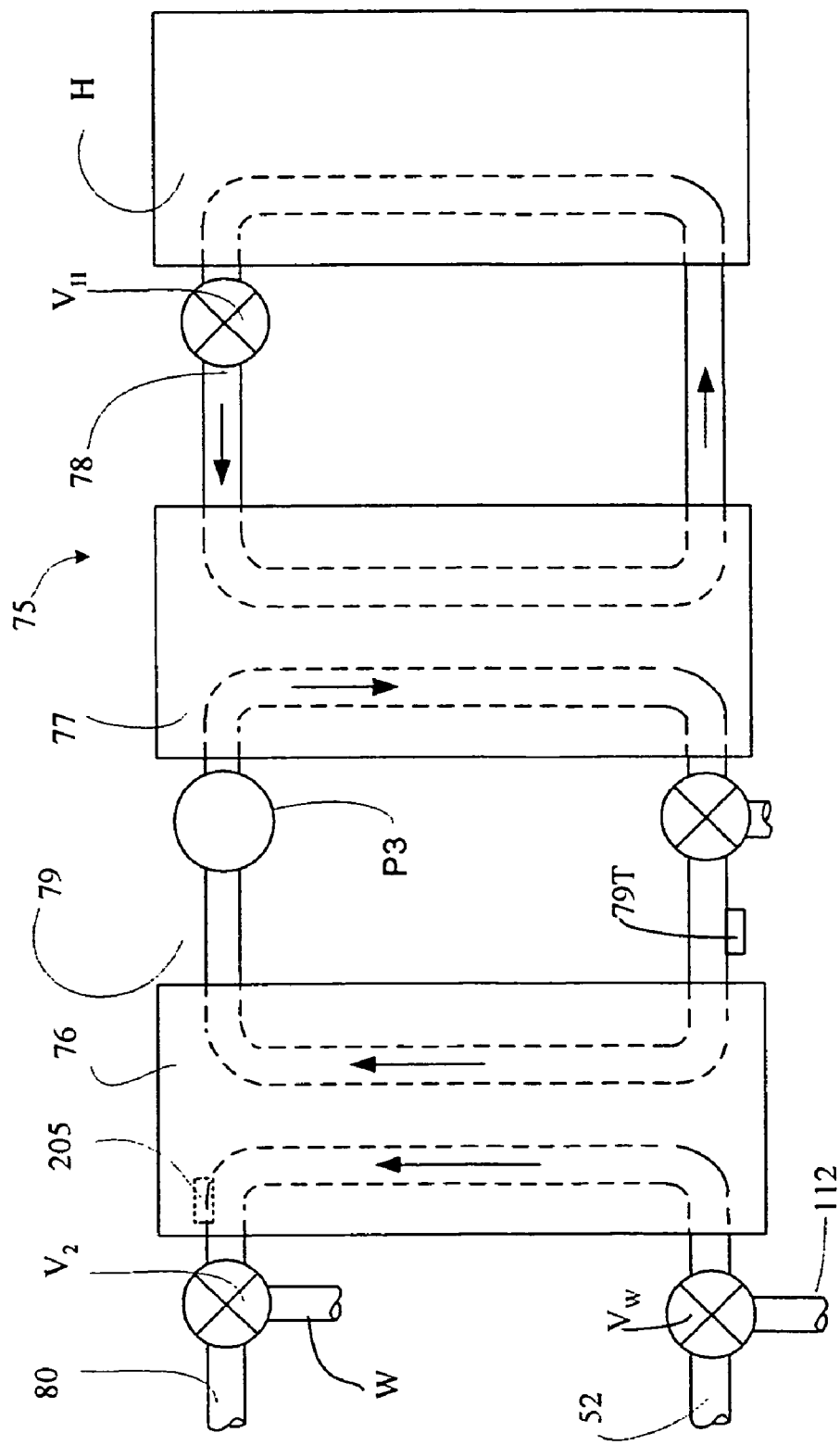

In the automated processing apparatus, heating of the green juice is effected in a heater 75 shown in FIGS. 2 and 9, as is also described in greater detail below. The duration of heating is effected by an insulated piping system 90 shown in FIGS. 2 and 10, and described in greater detail below.

The heat-treated and pH adjusted green juice is quite unique in that the pH of green juice influences the distribution of virus, proteins and peptides in the supernatant or pellet during subsequent centrifugations. Depending on the species of interest, the pH of green juice may be readily controlled to facilitate the isolation and purification of the desirable product, either virus particles or proteins and peptides. It thus provides a streamlined operation such that the isolation and purification of different viruses and proteins and peptides can be optimized with small modifications of a general purification procedure.

After heating, the juice is cooled in a cooling apparatus, described in greater detail below.

Centrifugation of Green Juice

Figure 13:
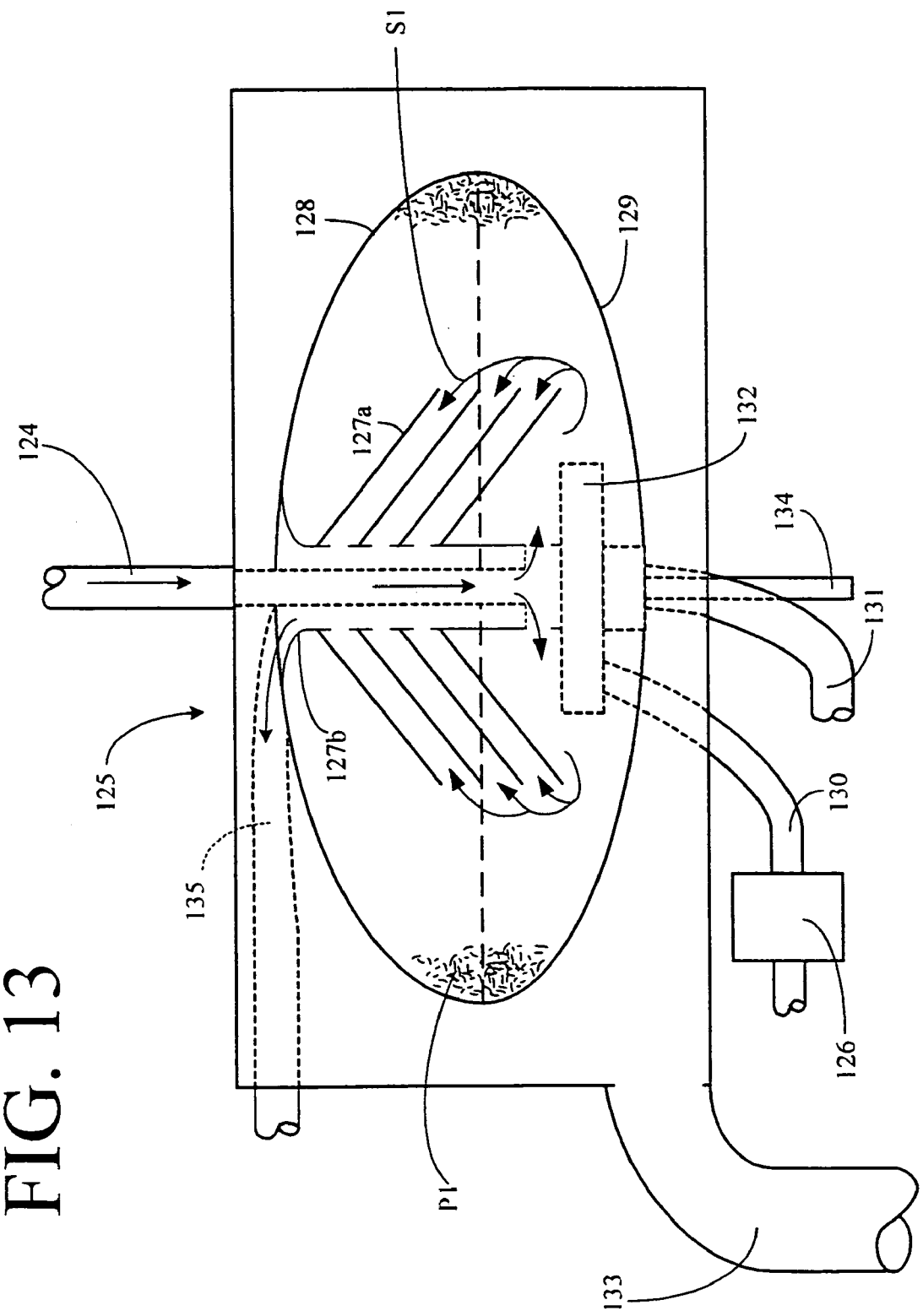
Figure 14:
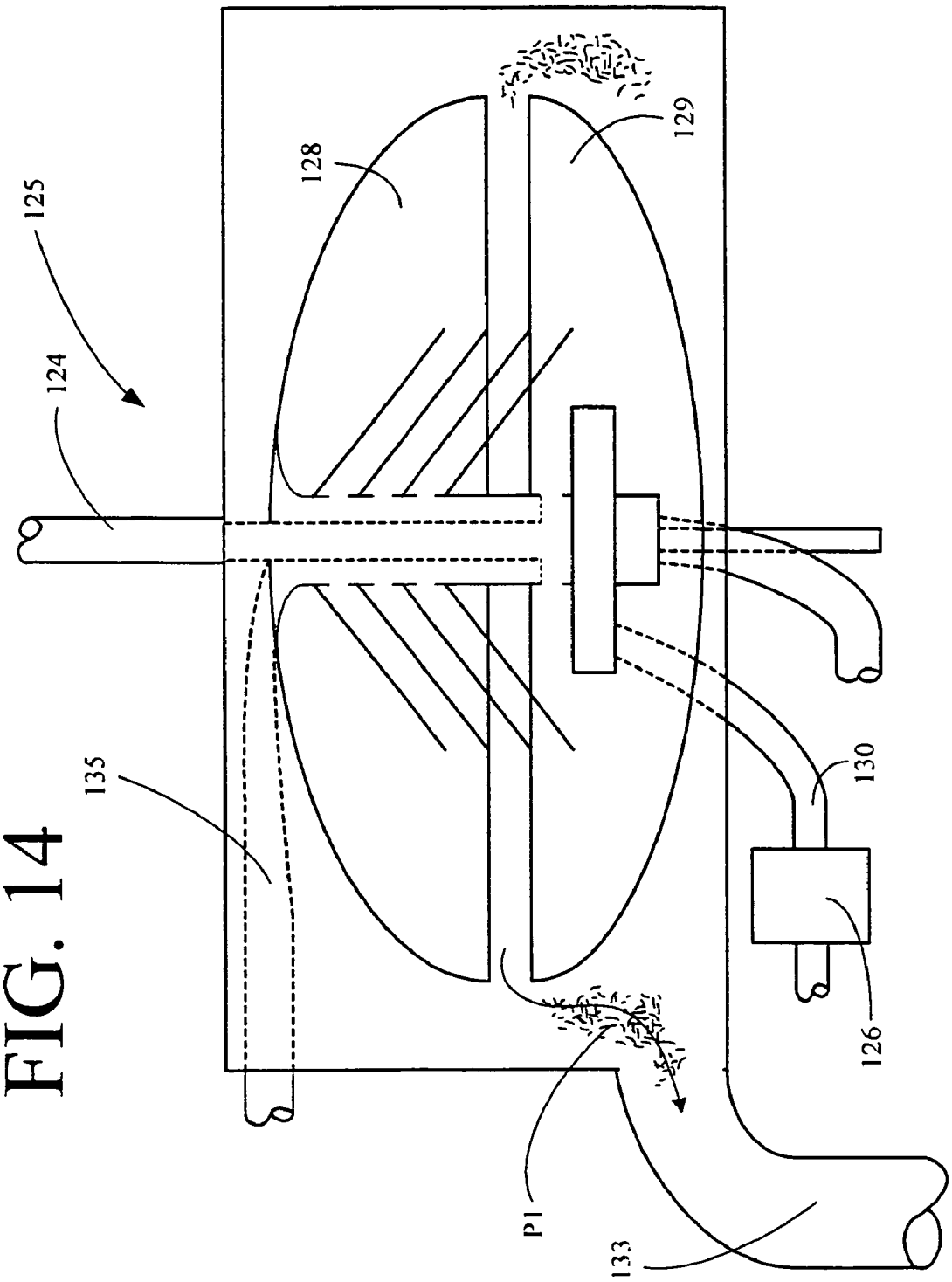

The pH-, heat-treated and cooled green juice may then be subjected to centrifugation (see (C) in FIG. 1). Those of skill in the art may readily determine suitable conditions for centrifugation, including time interval, dwell time for expulsion of solid pellet material and G-force. It is generally contemplated that centrifugation should be of sufficient G-force and time to pellet substantially all of Fraction 1 protein, chloroplast and other host materials, while retaining the desired target species in the supernatant fraction or at a sufficient speed and time to pellet the target species with Fraction 1 protein, chloroplast and other host materials. For example, centrifugation at 3000×G for two minutes or at 6000×G for three minutes have been effectively applied to the green juice in some embodiments of the instant invention. In the present invention, a first centrifuge 125 is employed, as depicted in FIGS. 2, 13 and 14.

According to the present invention, a majority of Fraction 1 protein, unassembled fusion proteins and peptides, chloroplast and other host materials that are insoluble at a pH of between about 4.0 and 5.2 (in the above pH treatment step) remain in the pellet (P1) (see (D) in FIG. 1) separated by centrifugation (B), while Fraction 2 proteins including recombinant proteins and peptides may generally remain in the supernatant (S1) (see (E) in FIG. 1). The virus, however, may partition between pellet and supernatant after centrifugation, depending upon the pH of the green juice, the virus species, virus nucleic acid construct, plant species, plant age, and source of plant tissue, among other factors. At a low pH, preferably below a pH of about 5.0, the virus is predominantly retained in the pellet (P1). At a pH of between about 5.0 and 5.2, virus is present in the supernatant (S1) as well. Depending on the species of interest, the pH of green juice and subsequent centrifugation conditions may be readily controlled to facilitate the isolation and purification of the desirable product, either virus particles or proteins and peptides. Thus, the automated processing apparatus of the present invention provides a streamlined operation such that the isolation and purification of different viruses and proteins and peptides can be achieved flexibly allowing for modifications of a general purification procedure.

Resuspension of Pellet in a pH Controlled Buffer

The pellet P1 obtained by centrifugation of the pH-adjusted and heat treated green juice typically contains Fraction 1 protein, unassembled fusion proteins and peptides, viruses, and other host materials as represented at (D) in FIG. 1. The pellet P1 may be re-suspended in water or in a buffer solution having the desired pH range, or pH adjusted to that range. The optimal pH is determined by the final species of interest. For instance, in some instances, the pH range of re-suspension is about 5.0 to 8.0 for isolating and purifying virus particles (see (F) FIG. 1). In other instances, the pH range of re-suspension is between 2.0 to 5.0 if the desired product is a fusion protein/peptide (see (G) FIG. 1). Those skilled in the art may readily choose appropriate buffer solution or acids or bases to reach the designed pH range without undue experimentation. Re-suspension of the pellet P1 is effected in a second pH adjuster tank 108, shown in FIGS. 2, 15, 16 and 17 and described in greater detail below.

Isolation and Purification of Virus

Viruses can be recovered from either the pellet (P1) alone, the supernatant (S1), or both the supernatant (S1) and pellet (P1) after centrifugation (C) of the green juice depending upon the pH and degree of virus partitioning. Further, it is possible to recover a product from the supernatant (S1) and recover more of that same product from the pellet (P1). Alternatively, it is possible to recover a first product from the supernatant (S1) and a second product from the pellet (P1).

When the pH of green juice is adjusted to a low value, for example, about 4.0 in. step (B) in FIG. 1, the virus is in general quantitatively retained in the pellet along with Fraction 1 protein chroloplast and other host material after centrifugation of the green juice ((D) in FIG. 1). After re-suspension ((F) in FIG. 1) in a solution having a pH of about 5.0 to 8.0, the mixture may be subjected to another centrifugation step (H) using a second centrifuge 175 shown in FIGS. 2 and 17. Virus particles are predominantly retained in the supernatant (S2) indicated at (I) in FIG. 1 and may be separated from Fraction F1 protein, chroloplast fragments and other host materials in the pellets. Typically only about 5–10% of the starting green juice protein remains in S2. The virus containing supernatant may then be ultrafiltered (J), if necessary, using a molecular weight cut-off (MWCO) in the range of about 1–500 kD membrane. For example, a 100 kD MWCO membrane is used in an ultrafiltration apparatus 300 (shown in FIGS. 2 and 18) of the automated processing apparatus for retaining virus particles in the concentrates, while smaller protein components filter through. The ultrafiltration (J) step results in a substantial further reduction in the process volume. From ultrafiltration (J) or centrifugation, a final purification of virus (K) may be accomplished by methods such as PEG-precipitation, centrifugation, re-suspension, and clarification.

In some instances, virus particles may also be obtained from the supernatant (S1) at (E) in FIG. 1 after the centrifugation of the green juice. The supernatant (S1) fraction normally contains Fraction 2 proteins and peptides. In some instances, the pH of green juice may be adjusted (B) to a value between about 5.0 and 5.2, preferably around pH 5.0. A significant portion of virus particles may then be recovered from the supernatant (S1) (at (E) in FIG. I) in addition to the pellet (P1) (at (D) in FIG. 1) after centrifugation (at (C) in FIG. 1) of the green juice. The virus containing supernatant may be ultrafiltered (at (L) in FIG. 1) using a molecular weight cut-off membrane in the range of about 1–500 kD. For example, a 100 kD MWCO membrane has been successfully used in the ultrafiltration apparatus 300 of the automated processing apparatus of the present invention to retain virus particles in the concentrates (shown in FIG. 2 and described in greater detail below), while smaller protein components, e.g. Fraction 2 proteins filter through. The ultrafiltration step (L) results in a substantial further reduction in the process volume. From ultrafiltration or centrifugation, a final purification of virus (Q) may be accomplished by prior art methods such as PEG-precipitation (M), centrifugation, resuspension, and clarification.

The present methods of isolating and purifying virus particles represent significant advantages over the prior art methods. They allow the ultrafiltration of virus-containing supernatant (S1 and/or S2), which significantly reduces the processing volume and removes plant components, such as, sugars, alkaloids, flavors, and pigments and Fraction 1 and 2 proteins. Desired virus particles can be enriched as particulate. The concentration and purification of virus particles is thus rapid and effective.

Isolation and Purification of Soluble Proteins and Peptides

The Fraction 2 proteins including recombinant proteins and peptides remain soluble after pH adjustment and heat treatment and centrifugation of green juice (see FIG. 1). The Fraction 2 protein-containing supernatant has removed sufficient Fraction 1 proteins, chloroplast and other host materials, to enable an efficient isolation and purification of Fraction 2 proteins, especially recombinant proteins and peptides, using size fractionation by ultrafiltration (L), concentration and diafiltration.

Ultrafiltration (L) is typically performed using a MWCO membrane in the range of about 1 to 500 kD according to methods well known in the art. In some embodiments of the instant invention, a large MWCO membrane is first used to filter out the residual virus and other host materials. Large molecular weight components may remain in the concentrates. Filtrates containing the proteins/peptides of interest may be optionally passed through another ultrafiltration membrane, typically of a smaller MWCO, such that the target compound can be collected in the concentrates. Additional cycles of ultrafiltration may be conducted, if necessary, to improve the purity of the target compound. The choice of MWCO size and ultrafiltration conditions depends on the size of the target compound and is an obvious variation to those skilled in the art. The ultrafiltration step generally results in a reduction in process volume of about 10- to 30-fold or more and allows diafiltration to further remove undesired molecular species. Finally, proteins or peptides of interest may be purified using standard procedures such as chromatography, salt precipitation, solvent extractions including super critical fluids such as $CO_2$ and other methods known to those of skill in the art.

The method of isolating and purifying Fraction F2 proteins by the automated apparatus of the present invention represents significant advantages from the prior art methods. First, it does not require acid-precipitation of F2 proteins. Acid-precipitation in the prior art may not be desired since many proteins may be denatured or lose enzymatic or biological activity. Fraction F2 proteins including recombinant proteins and peptides in the instant invention are not retained in a pellet form, thereby minimizing the risk of protein denaturation. The present method thereby minimizes denaturation of proteins and peptides of interest. Second, because the more abundant component, Fraction 1 protein, is eliminated during the early stages of purification, the downstream process allows the ultrafiltration of Fraction F2 proteins. Ultrafiltration of Fraction F2 proteins permits significant reduction of processing volume and allows rapid concentration and purification of proteins and peptides. Desirable proteins and peptides can be enriched by molecular weight. Rapid concentration and purification also reduces or eliminates the degradation or denaturation due to endogenous protease activities. Ultrafiltration of Fraction F2 proteins is not applicable with methods in the prior art. Finally, the concentration of Fraction F2 proteins including recombinant proteins and peptides requires no solvents and no additional chemicals.

Plant protein and peptide isolation procedures in the prior art frequently use solvents such as n-butanol, chloroform, and carbon tetrachloride to eliminate chloroplast membrane fragments, pigments and other host related materials. Such methods are not easily practiced on a large and commercially valuable scale since these methods present the problems of safety and solvent disposal, which often require designing special equipment compatible with flammable fluids, and hence require facility venting and providing protective equipment to workers.

Isolation and Purification of Unassembled Fusion Proteins and Fusion Peptides

During virus replication or during the process of isolating and purifying a virus, its coat protein may become detached from the virus genome itself, or accumulate as unassembled virus coat protein, or the coat protein may never be incorporated. One of ordinary skill in the art can envision that the coat protein can be designed through established recombinant nucleic acid protocols to intentionally be unassembled for commercial recovery of proteins having a plurality of biochemical features. This coat protein may contain a recombinant component integrated with the native coat protein, or fusion proteins. These unassembled fusion proteins typically co-segregate in the pellet (P1) with Fraction F1 protein after centrifugation of pH adjusted and heated green juice. The pellet may then be re-suspended in water or in a buffer with a pH value within the range of about 2.0 to 4.0 (see (G) in FIG. 1) followed by another centrifugation (see (R) in FIG. 1). The unassembled protein may be further purified according to conventional methods including a series of ultrafiltration, centrifugation and chromatography steps. The fusion peptide may be obtained followed by chemical cleavage of the desired peptide or protein from the fusion peptide (fusion proteins).

Isolation and Purification of Sugars, Vitamins, Alkaloids, and Flavors

Sugars, vitamins, alkaloids, flavors, amino acids from a plant may also be conveniently isolated and purified using the method of the instant invention. After ultrafiltration (L) of the pH adjusted and heated green juice, the permeate contains Fraction F2 proteins, viruses and other materials, including sugars, vitamins, alkaloids, and flavors. The permeate produced thereby may be separated from the Fraction F2 protein and other host materials by further ultrafiltration (N). Sugars, vitamins, alkaloids, flavors (T) may then be further purified by a series of low molecular weight cutoff ultrafiltration steps.

Figure 1A:
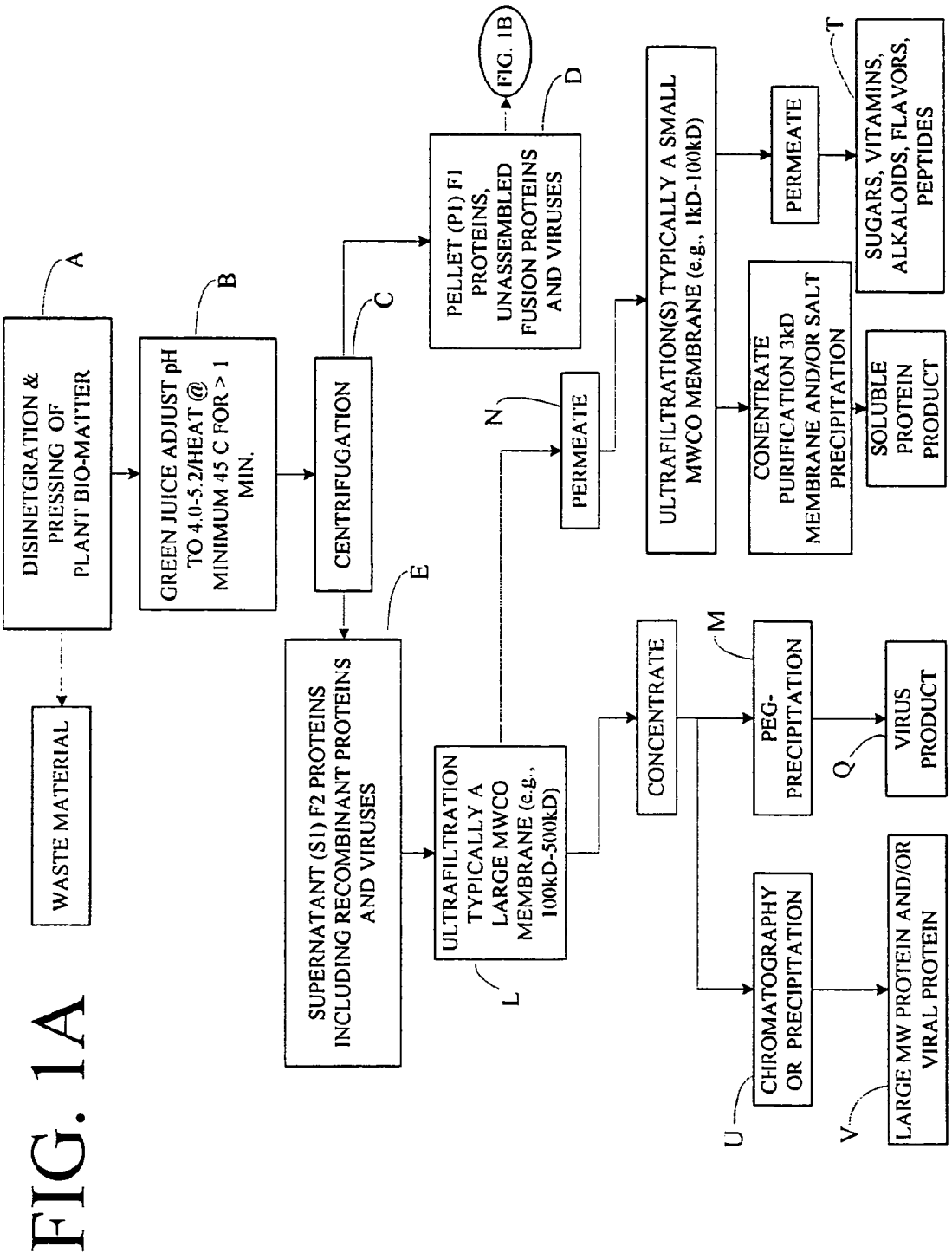

Isolation of Large Molecular Weight Proteins and/or Viral Proteins and Other Proteins As shown on the left hand side of FIG. 1 (see FIG. 1A) after ultrafiltration (L), the concentrate may be subjected to chromatography or precipitation techniques (U) to yield large molecular weight proteins or viral protein (V).

Figure 1B:
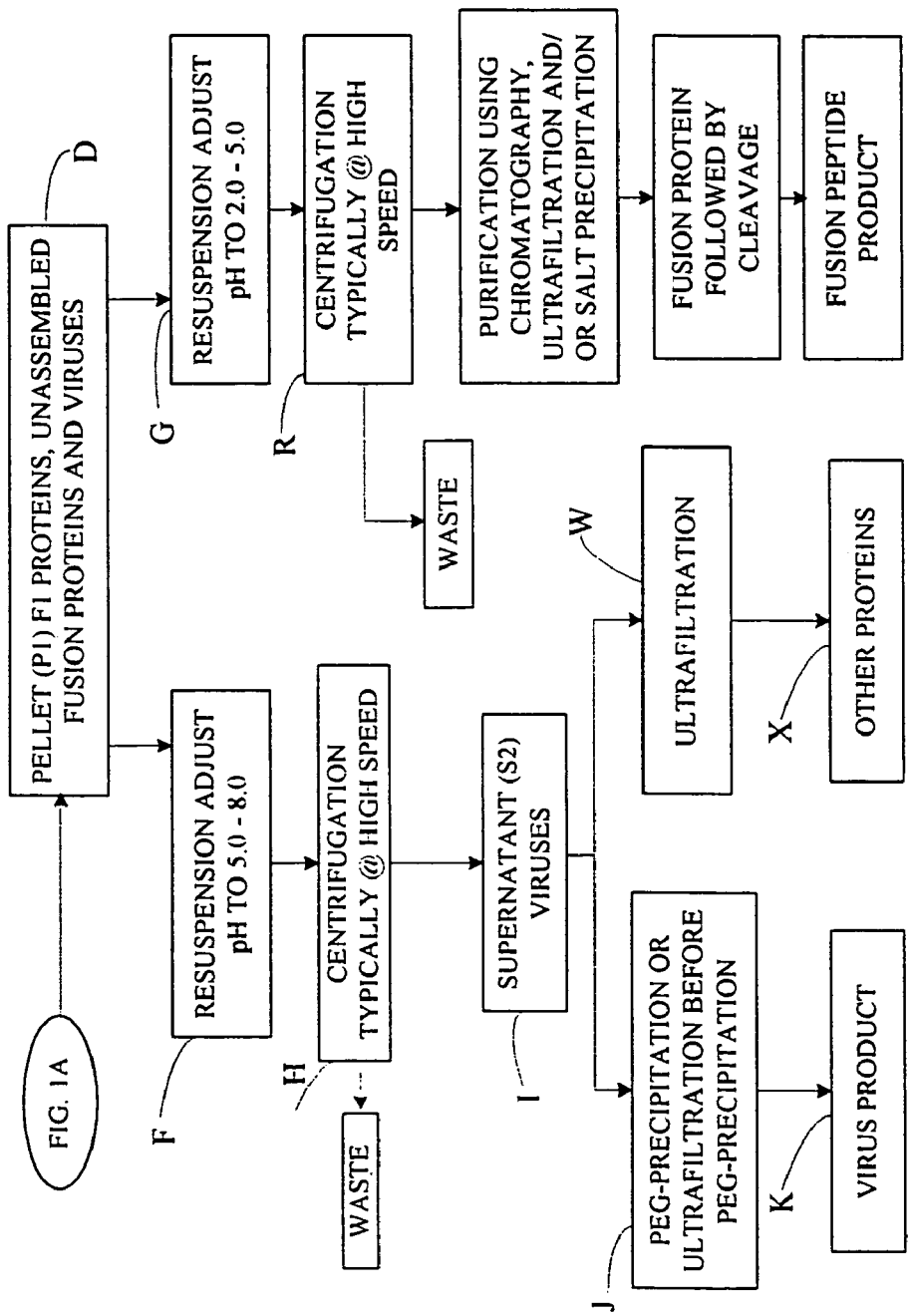

Further, as shown in FIG. 1 (center of FIG. 1B) it is also possible to extract additional proteins (X) from the supernatant S2 via ultrafiltration (W).

Automated Apparatus

Description is now provided for the automated processing apparatus of the present invention. The automated processing apparatus is described below device by device, with reference to FIGS. 2 through 18, and computer control of the automated processing apparatus is described below with reference to FIGS. 19–28.

The automated processing system of the present invention is controlled from a central location, for instance, a control room 490 that houses a computer 500 (see FIG. 19) but may also be controlled at various locations around the processing equipment via SCADA (supervisory control and data acquisition) nodes. The computer 500 and SCADA nodes are described in greater detail below with respect to FIG. 19, and also with the description of the various elements of the automated processing system below.

The automated processing system of the present invention includes a first conveyer 5 for bringing plant material from harvesting means (not shown) into the devices of the automated processing apparatus. The harvesting means (not shown) includes, for example, farm equipment such as a truck, tractor or trailer used to harvest and/or collect and haul harvested plant materials. The conveyer 5 is, for instance, manufactured by Balzer Manufacturing Corp., Mountain Lake Minn., and is a stationary conveyer box including a chain conveying mechanism for moving plant material from a lower end thereof to an upper end thereof. It should be understood that the conveyer 5 is an optional feature for convenience only and is not a required element in the automated processing apparatus of the present invention. The conveyer 5 is manually operated, but in an alternate embodiment may be connected to and controlled by the computer 500 or may be manually operated.

The harvesting means deposits the harvested plant material onto the lower end of the conveyer 5 as the conveyer 5 moves the material upward and then via beater bars, moves over to a narrow second conveyer 10. The second conveyer 10 is, for instance, a conveyer manufactured by MAC Manufacturing, Lebanon Junction Ky. and includes an endless belt that moves harvested material from a lower end thereof to an upper end thereof. The second conveyer 10 moves the harvested material upward, feeding the harvested material into a chute 15 that guides the harvested material into a grinder assembly 22 that is depicted separately in FIG. 3.

The second conveyer 10 is connected to the computer 500 (described below) for automated operation, but may also be manually operated. In an alternate embodiment, the second conveyer 10 is equipped with weigh belts (not shown) under the endless belt for determining the weight of mass transported by the second conveyer 10. It is desirable to monitor the mass of material entering the grinder assembly 22 in order to achieve a desired mass feed rate.

In an alternate embodiment, the second conveyer 10 is equipped with a juice collection tray (not shown) for collecting juice falling from the bio-matter being conveyed. If, for instance, the bio-matter being processed is a leafy substance such as tobacco leaves, juice may be draining from the recently harvested material. This juice may contain the material of interest. Therefore, it is advantageous to capture and retain this juice. As shown in FIG. 2, an optional pump 11 pumps juice collected from the juice collection tray beneath the conveyer 10 and pumps the collected juice into the grinder assembly 22 to minimize loses. It should be understood that the collection tray and pump 11, although depicted are optional features.

Figure 3:
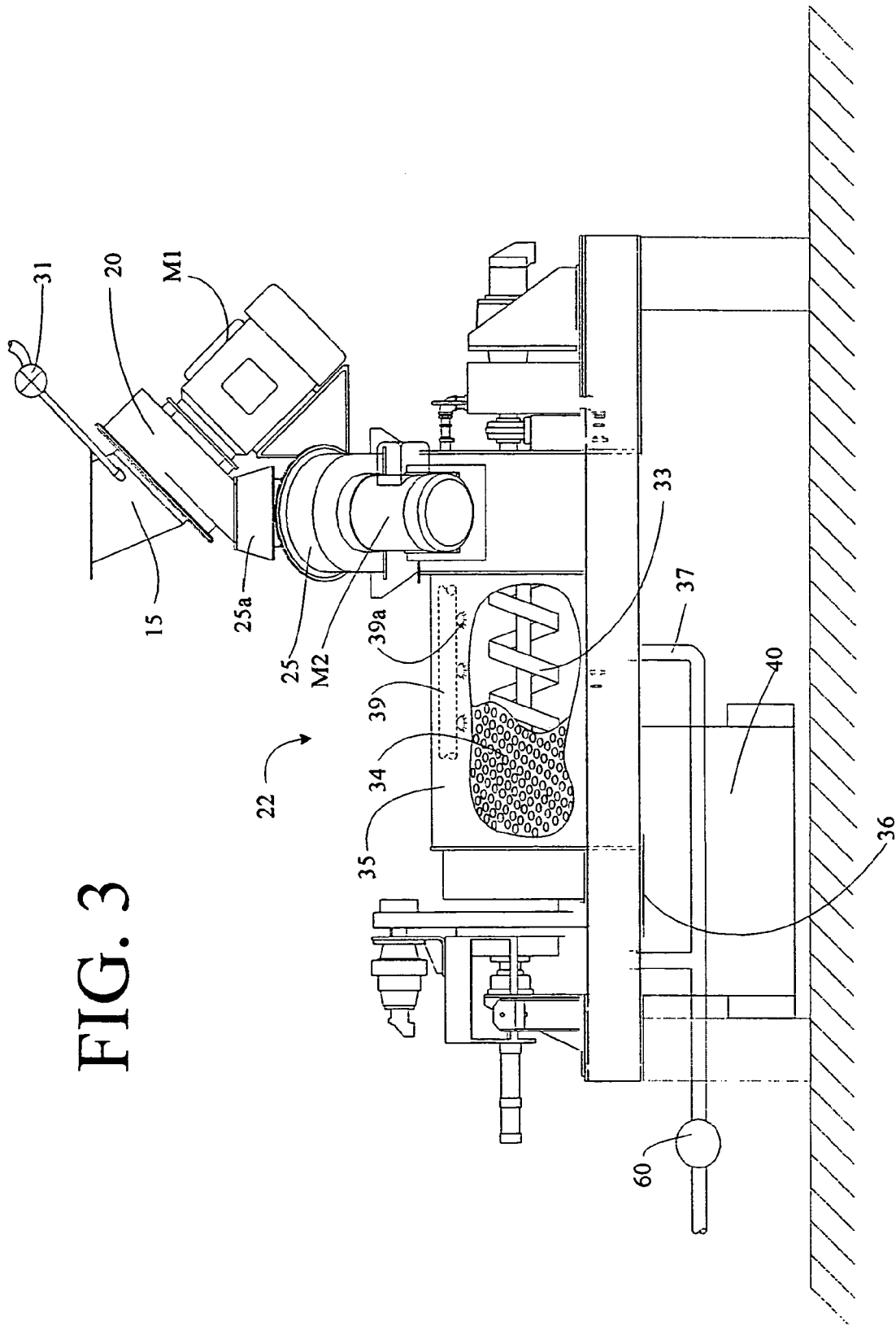

The grinder assembly 22 includes a first grinder 20, a second grinder 25 and a press 35 that are indicated in FIG. 2, but are more clearly shown in FIG. 3 with other portions of the automated processing apparatus of the present invention removed to provide greater clarity.

The first grinder 20 is attached to and supported by the second grinder 25 and further the first grinder 20 exhausts ground bio-matter directly into the second grinder 25. The second grinder is attached to and is supported by the press 35. Further, the second grinder 25 exhausts ground bio-matter directly into the press 35.

The first grinder 20 is powered by a large electric motor M1 shown in FIG. 3 having a power capability of approximately 60 horsepower and being capable of rotating at speeds of up to 3600 rpm. A liquid feed is connected to the first grinder 20 such that liquid can be selectively fed in to the first grinder 20 via control of a pump 31, as is described in greater detail below.

Figure 4:
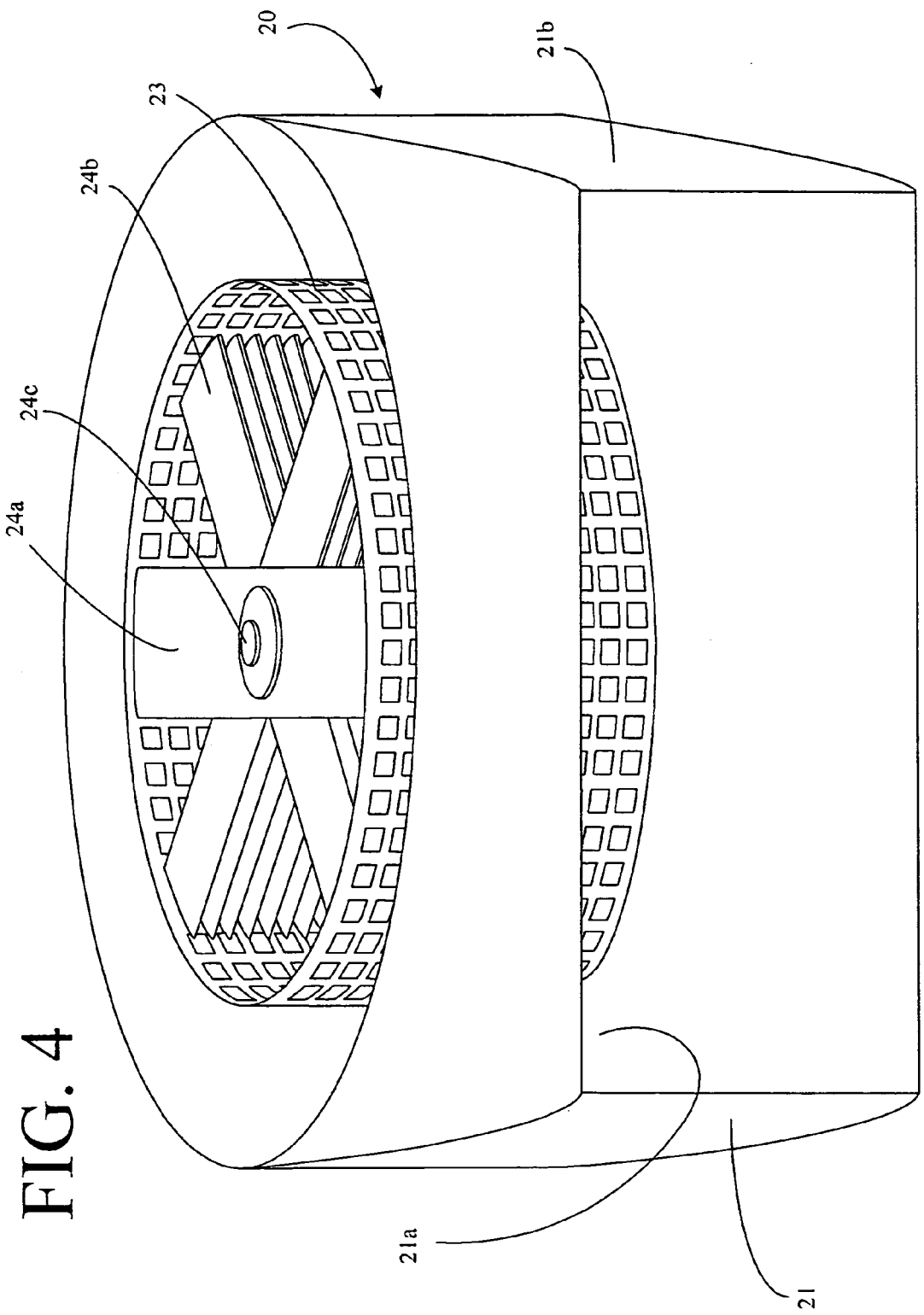

A portion of the first grinder 20 is shown in FIG. 4 with the chute 15 removed to reveal a shroud 21, a screen 23 and blades 24a and 24b. The blades 24a and 24b are supported on a shaft 24c of the electric motor M1. The first grinder 20 may be any of a variety of grinders, however the model currently employed is model RP-18 Disintegrator manufactured by Hosokawa Bepex Corporation, Japan. The screen 23 is held in place between the shroud 21 and the chute 15 in a fixed position surrounding the blades 24a and 24b. The screen 23 is formed with a plurality of ½ inch square holes encircling the blades 24a and 24b. The holes in the screen 23 are not limited to the ½ inch size shown, but may be sized anywhere between ¼ inch to several inches depending on the bio-matter being processed. However, in the depicted configuration, the holes are about ½ inch square and are dimensioned for optimal cutting and subsequent disintegration of leafy bio-matter such as tobacco leaves. The holes in the screen 23 are shown slightly spaced apart from one another but may also be close together to allow maximum penetration of cut plant material out of the screen 23 after cutting by the blades 24a and 24b. The shroud 21 surrounds the screen 23 but is radially spaced apart from the screen 23 and captures cut plant material from the first grinder 20 exiting through the holes in the screen 23 and directs the cut plant material out of the shroud 21 through a chute 21b into a further chute 25a (FIG. 3) of the second grinder 25.

There is a plurality of blades 24b in the first grinder 20 offset from adjacent blades 24b by 90° forming an X shaped array of blades, as shown in FIG. 4. The blade 24a is offset by 45° from the adjacent blade 24b. The blade 24a is the first blade to engage bio-matter entering the first grinder 20 with a clearance between the ends of the blade 24a and the screen 23 of about ⅛$^{th}$ of an inch. The blades 24a and 24b are thin, sharp blades much like lawn mower blades with sharp leading edges to cut into the plant material. The blades 24b have a length that is almost equivalent with the inner diameter of the screen 23 with a clearance therebetween of about ⅛ of an inch or less. The size of the holes in the screen 23 are such that the plant material is retained within the screen 23 until the plant material has been cut to a small size enabling the bio-matter to pass through the holes in the screen 23.

The shroud 21 is formed with a bottom 21a that engages the screen 23 such that cut plant material can only pass out of the screen 23 via the holes in the screen 23. The shroud 21 is further formed with the chute 21b that directs cut plant material into the second grinder 25 for further cutting.

The chute 15 is removeably fixed to the shroud 21 and engages the upper edge of the screen 23 thereby forming a cutting chamber for processing plant material. Therefore, all plant material entering the first grinder 20 through the chute 15 is cut by the rotating blades 24a and 24b until the plant material is small enough to fit through the holes in the screen 23.

After leaving the shroud 21 through the chute 21b, cut plant material enters the second grinder 25 via the chute 25a shown in FIG. 3. The second grinder 25 is similar to the first grinder in shape and configuration but is designed to further cut and grind the plant material entering through the chute 25a. The second grinder 25 is an RP-12 Disintegrator manufactured by Hosokawa Bepex, a Japanese manufacturer.

Figure 5:
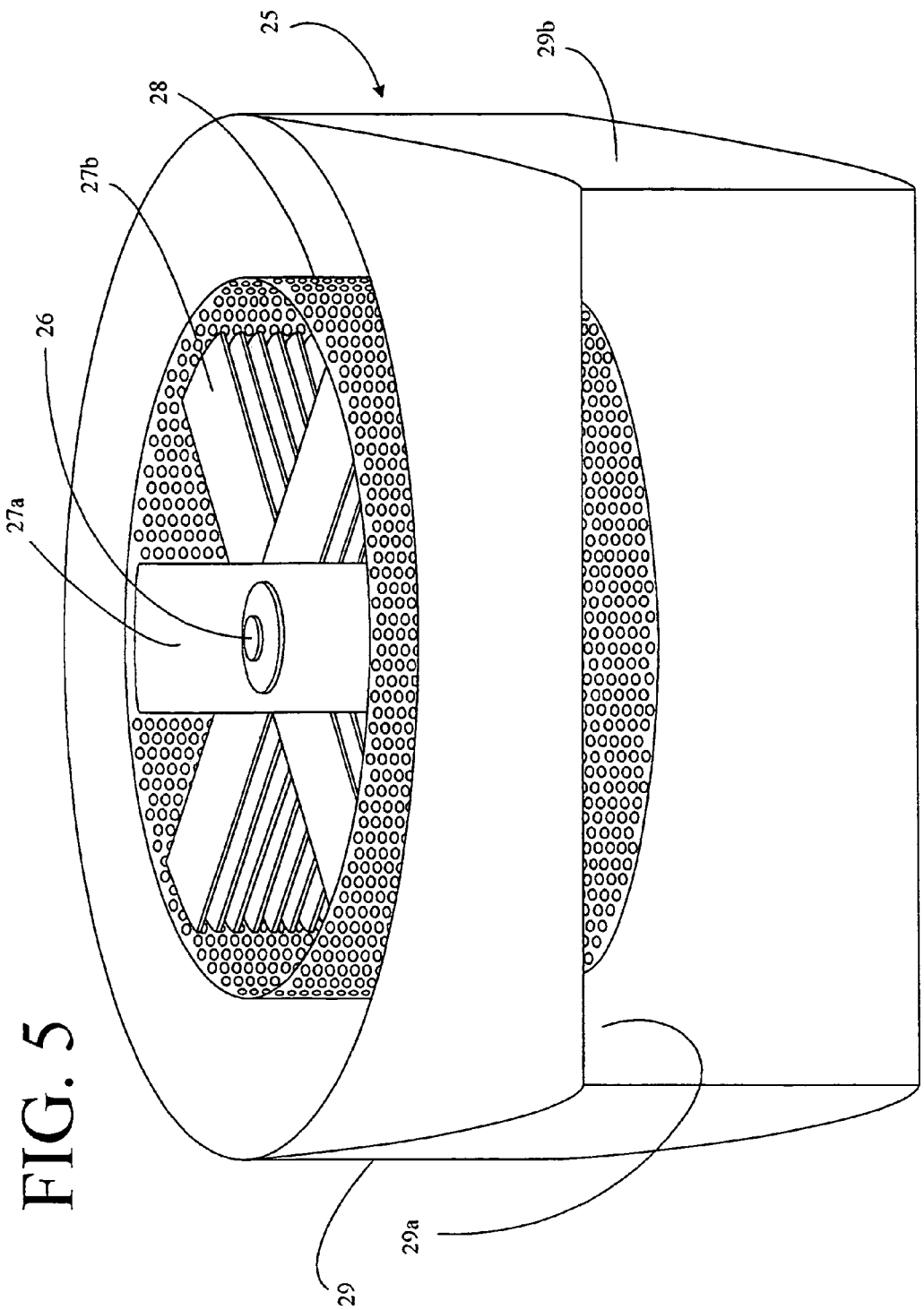

FIG. 5 shows the second grinder 25 with the chute 25a removed to reveal a motor shaft 26 of a motor M2 (see FIG. 3). The motor M2 is similar to the motor M1 having approximately the same power and speed. The shaft 26 supports blade hammers 27a and 27b. The blade hammers 27a and 27b are surrounded by a screen 28. The screen 28 is further encircled by a shroud 29 formed with a bottom 29a and a chute 29b.

The blade hammers 27b are offset from one another by 90° forming an X-shaped pattern, as is shown in FIG. 5. The blade hammers 27b have a length that is approximately equal to the inner diameter of the screen 28 such that as bio-matter is cut by the blade hammers 27b and pulverized if trapped between the ends of the blade hammers 27b and the inner surface of the screen 28. In other words, the ends of the blade hammers 27b almost contact the inner surface of the screen 28 with a clearance of preferably less than $\frac{1}{8}^{th}$ of an inch, and more preferably between $\frac{1}{16}^{th}$ and $\frac{1}{64}^{th}$ of an inch. The screen 28 is formed with small round holes having a $\frac{3}{8}^{th}$ inch diameter. The small round holes are dimensioned along with the holes in the screen 23 in the first grinder for optimal disintegration of leafy bio-matter such as tobacco leaves.

It should be understood that the screens 23 and 28 depicted have been dimensioned for optimal cutting and disintegration of leafy bio-matter and the present invention is not limited to the size and shape of the holes in the screens 23 and 28 described above. Alternatively, the holes in the screens 23 and 28 are dimensioned and shaped for the specific bio-matter being processed. For example, for processing of a grain or seed material, holes in the screens 23 and 28 should be smaller and may have a rectangular shape much like a slit, have a triangular shape or other shape that optimizes the disintegration of the material being processed. Typically, the holes in the screen 23 are larger than the holes in the screen 28 such that the first grinder 20 reduces the size of the bio-matter being processed and the second grinder 25 further reduces the size of the bio-matter to maximize cellular disruption of the bio-matter being processed.

The blade hammer 27a is offset from the adjacent blade hammer 27b by 45° and is slightly shorter that the blade hammers 27b. The blade hammer 27a is a thin blade much like a lawn mower blade and engages plant material as the bio-matter first enters the second grinder 25. The blade hammers 27b are thicker than the blades 24a, 24b and 27a. The blade hammers 27b being thicker than the blades 24a and 24b, and having the above mentioned ends in close proximity to the inner surface of the screen 28 act as hammers to further pulverize the bio-matter entering the second grinder 25.

The shroud 29 includes a bottom 29a that contacts and supports the screen 28. The screen 28 is further held in position by the chute 25a such that the screen 28 is fixed in place with respect to the shroud 29. The shroud 29 and chute 25a define a chamber within the second grinder 25 for further cutting, hammering and pulverizing plant material The shroud 29 further includes a chute 29b that directs the cut bio-matter and green juice now released from the bio-matter into the press 35, as is described in greater detail below.

The combination of the first and second grinders 20 and 25 effectively cuts, pulverizes and disintegrates bio-matter entering the grinding assembly 22 in order to maximize cellular disruption and maximize release of intracellular material. Specifically, the bio-matter is effectively disintegrated so that when pressed in the press 35 a maximum amount of the material of interest is extracted from the solid or pulp material of the bio-matter being processed.

In the embodiment of the first and second grinders 20 and 25 shown in FIGS. 4 and 5, the first grinder 20 is provided with knives 24a and 24b and the second grinder 25 is provided with hammers 27a and 27b. However, it should be understood that various configurations of knives and hammers may be employed in the grinders. For example, for processing some bio-matter it is advantageous for both the first and second grinders to be provided with knives. Alternatively, for some bio-matter it is advantageous for both the grinders to be provided with hammers in order to pulverize the bio-matter. In yet another embodiment, the knife blades and/or hammers in either the first and/or the second grinders may be pivotable about a pivot pin offset from the motor's. The size, configuration and arrangement of each set of knife blades and/or hammers is determined by the nature of the bio-matter being processed and the material of interest being extracted from the bio-matter.

The press 35 depicted in FIG. 3 is a commercially available press manufactured by Rietz Manufacturing, Santa Rosa, Calif., although any press with similar features may be employed. The press 35 is a corkscrew type press having an elongated auger bit shaped shaft 33 that presses any and all solid pulp materials from the cut bio-matter against a rotating cone (not shown) thereby forcing the pulp against the cone and also against a fine mesh screen 34 forcing all green juice from the pulp materials. The fine mesh screen 34 has very small holes in cases where leafy material is processed such that only green juice passes therethrough. However, it should be understood that the configuration of the mesh screen 34 is not fixed but rather depends upon the nature and characteristics of the bio-matter being processed. For example, in cases where a seed or grain-like material or other non-leaf material is being processed, the mesh screen 34 may have finer holes to retain solid matter or may have a filter paper-like liner that allows the extracted juice therethrough. The pressed pulp material is forced out through an exhaust port 36 (shown in FIG. 3) and onto a third conveyer 40 (shown in FIGS. 3 and 6) that takes the pulp material to a dryer 45, depicted in FIGS. 2, 6 and 7, that is described in greater detail below.

Green juice extracted from the bio-matter is collected within the press 35 and exits the press 35 via pipe 37 and is pumped by a first pump 60 to a pH adjuster tank 102, shown in FIG. 2. The first pump 60 is controlled by a computer 500 that is described in greater detail below.

A feed pipe 39 mounted within the press 35 is provided with spray nozzles for periodically spraying liquid onto the auger shaft 33 thereby rinsing the shaft and solid material within the press 35 of any residue in order to maximize capture of the material of interest from the bio-matter. The feed pipe 39 is supplied with liquid from a tank 101 in a manner described in greater detail below along with a description of the tank 101.

Figure 6:
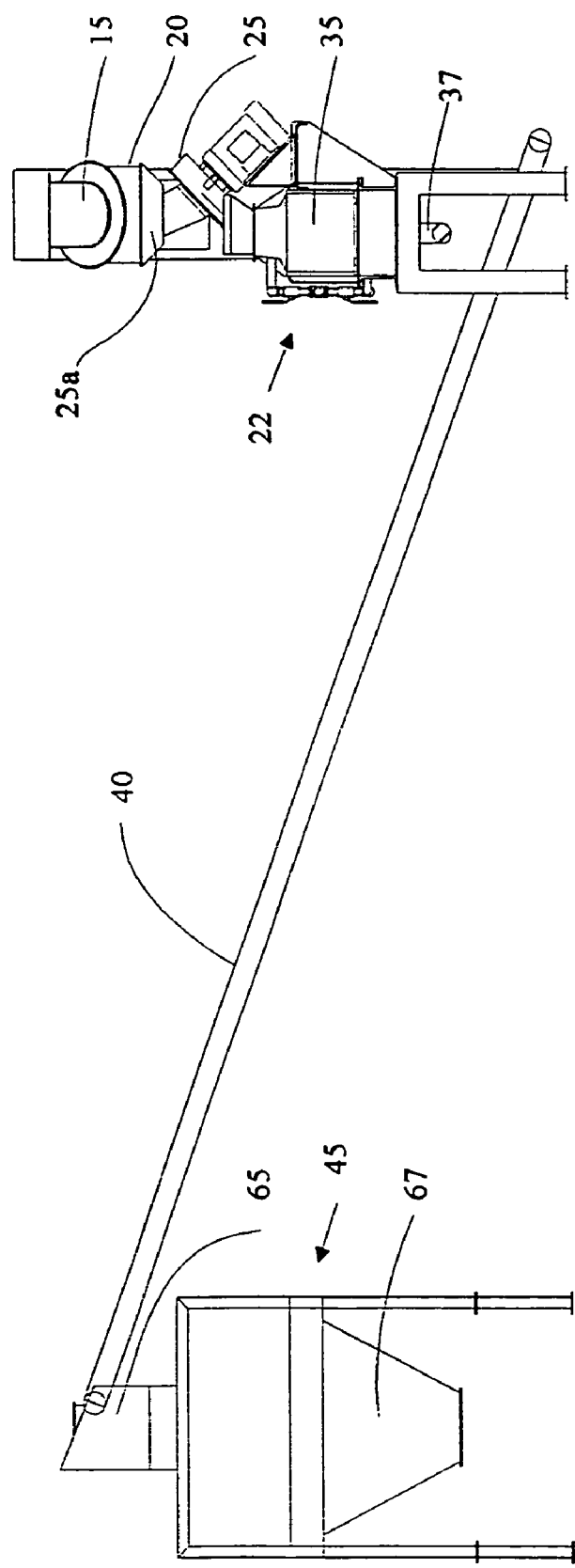
Figure 7:
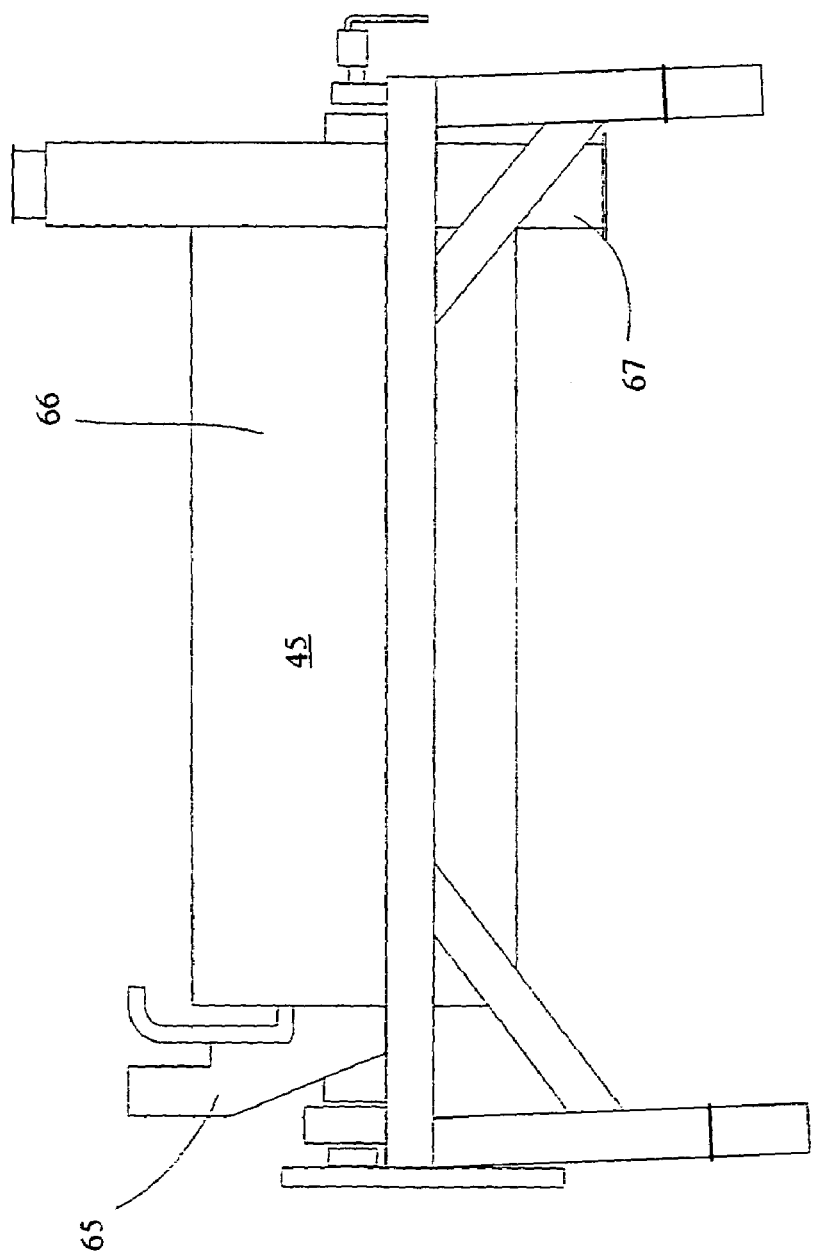

The dryer 45 is a rotating drum-type kiln manufactured by Cardwell manufacturing model number RSD 692 as shown in FIGS. 2, 6 and 7. The dryer 45 is controlled (on/off) by the computer 500, but may alternatively be manually controlled. A sensor in the dryer 45 controls provides a status signal to the computer 500 indicating operating status of the dryer 45. The conveyer 40 is a Quick Key Spool Conveyer manufactured by Sweet Manufacturing, Springfield Ohio, and delivers waste pulp material from the bottom of the grinder assembly 22 to a chute 65 at the top of one end of the dryer 45. The chute 65 directs the waste pulp material into a rotating drum 66. The rotating drum 66 is heated to a temperature above 212° Fahrenheit thereby heating and drying the waste pulp material. The temperature of the rotating drum 66 is preferably above 212° Fahrenheit but may be anywhere in the range of about approximately 212° to approximately 500° Fahrenheit.

The heat within the rotating drum 66 drives moisture out of the waste pulp material thereby reducing the weight of the waste pulp making it easier to dispose of. However, alternatively, if the waste material includes active biological substances, the dryer 45 may be heated to a temperature necessary to kill or otherwise render inactive any microbial matter that may remain within the waste plant material rendering the pulp material generally harmless to the environment.

The waste material exits the rotating drum 66 through a chute 67 located at a lower end of the rotating drum 66. As is shown in FIG. 7, the rotating drum 66 is inclined and the chute 67 is located at the lower end of the rotating drum 66. Therefore, all waste material eventually drops out of the rotating drum 66 via the chute 67 where it is collected on another conveyor 68 (shown in FIG. 2) that delivers the waste pulp material to a truck bed or trailer (not shown) and hauled away for use as, for instance, mulch. The heated and dried waste pulp may be returned to the field.

Figure 8:
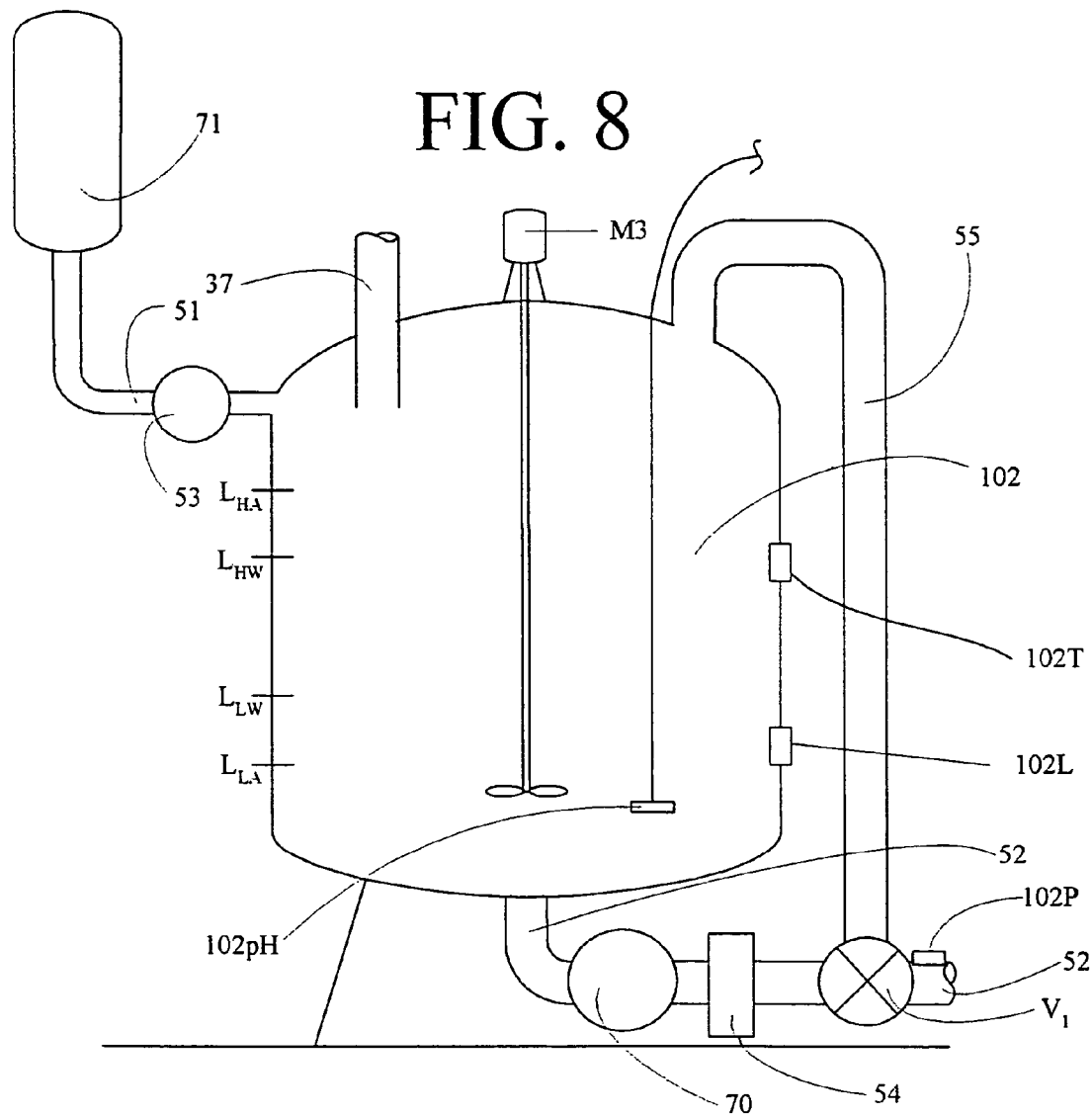

As mentioned above, the green juice extracted from the plant material exits the press 35 via pipe 37 and is pumped by a pump 60 (see FIG. 3) to a pH adjuster tank 102 shown in FIGS. 2 and 8. In FIG. 8, the pH adjuster tank 102 is shown separated from other portions of the automated processing apparatus. The pump 60 is controlled by the computer 500, as is described in greater detail below.

The pH adjuster tank 102 includes a motor M3 that powers an agitator to keep the green juice within the tank moving, stir pH adjusting material in with the green juice, eliminate settling of suspended matter in the green juice and maintain the green juice in a generally homogeneous state. The green juice enters the tank through the pipe 37 at the top of the tank 102. However, it should be understood that the location of the pipe 37 is not restricted to the location depicted. The pipe 37 may alternatively be located on the side or bottom of the tank 102. A pH adjuster inlet pipe 51 located on the tank 102 facilitates addition of a pH adjuster material to adjust the pH of the green juice in a manner described in greater detail below. In line in the inlet pipe 51 is a pump 53 that is selectively operated by the computer 500 to control flow of pH adjusting material into the tank 102 in a manner described in greater detail below. Further, the motor M3 that provides power to the agitator is also controlled by the computer 500, as is described below.

Although the pH adjuster inlet pipe 51 is shown on the side of the tank 102, it may alternatively be located at either the top or bottom of the tank 102. A pH sensor 102 pH is located inside of the tank 102, and in a lower portion of the tank, preferably near the bottom of the tank 102. The location of the pH sensor 102 pH is preferably in a position where the sensor 102 pH is in constant contact with green juice in the tank 102 for pH sensing but far enough away from the pipe 51 such that the pH readings from the pH sensor 102 pH are indicative of the green juice's current pH state, not the pH state of the inflowing pH adjusting material. A temperature sensor 102T and a level sensor 102L are also provided within the tank 102. The pump 53, temperature sensor 102T, level sensor 102L, motor M3 and pH sensor 102 pH are connected to a computer 500 (see FIG. 19) as is described in greater detail later below. Green juice exits the tank 102 through pipe 52. The pipe 52 is also provided with a pressure sensor 102P that detects the fluid pressure in the pipe 52 and sends such signals to the computer 500.

A pump 70 and flow-meter 54 are connected in the pipe 52 such that pH adjusted green juice in the tank 102 is pumped out of the tank 102 by the pump 70, thereby defining the downstream direction flow of green juice.

Downstream from the pump 70 is a magnetic type flow-meter 54 that is connected to the computer 500, as is described below. Also connected to the pipe 52 downstream from the flow-meter 54 is a valve $V_1$. The valve $V_1$ is designed to selectively change the flow of the green juice from the pipe 52 to a return pipe 55 that diverts green juice back into the tank 102 in a manner described in greater detail below. The valve $V_1$ is connected to, and controlled by signals from the computer 500.

During initial stages of processing, the tank 102 begins to fill with green juice supplied from the grinder and press apparatus 22. At this time, the valve $V_1$ is set such that all flow of green juice goes through the return pipe 55 and back into the tank 102 defining a re-circulation loop. Green juice is re-circulated back into the tank 102 in order to allow the proper pH level to be attained by the introduction of pH adjuster from the tank 71. The computer 500 monitors the flow of green juice through the flow meter 54 and the readings from the pH sensor 102 pH in order to determine the proper amount of pH adjuster pumped into the tank 102 via the pump 53.

The computer 500 also monitors the level of green juice within the tank 102 via signals from the level sensor 102L. Once the level of green juice in the tank 102 reaches a predetermined level, the valve $V_1$ is opened allowing pH adjusted green juice to flow onward to the heater assembly 75. The computer 500 is configured to return the valve $V_1$ back to re-circulation mode if the pH of the green juice is not within a predetermined range, or if other problems detected downstream from the tank 102 make re-circulation necessary.

With the valve $V_1$ in a position that allows flow of green juice to continue through the pipe 52, the green juice is pumped from the pH adjuster tank 102 to a heater assembly 75 shown in FIGS. 2, 9, 15, 16 and 17. The heater assembly 75, as shown separately in FIG. 9, includes a first heat exchanger 76, a second heat exchanger 77 and a heating unit H. Within the heater assembly 77, a heating fluid (such as hot water or steam) is produced in the heater H and then provided to the second heat exchanger 77 via a circulating pipe 78. A heat source within the heater H provides heat to heat the heating fluid in the pipe 78. The heat source may be any of a variety of heat sources such as an electric or gas heater. The heating fluid passes through the heat exchanger 77 providing heat to the heat exchanger 77 thereby heating a liquid in pipe 79. Heat from the heater H is controlled by a valve $V_H$, which is connected to and controlled by the computer 500. The liquid in pipe 79 is, for instance, city water fed into the pipe 79, heated in the heat exchanger 77 and recirculated by a pump $P_3$, the pump $P_3$ being connected to and controlled by the computer 500. A temperature sensor 79T provides temperature readings in the pipe 79 to the computer 500 for control of the pump $P_3$.

The green juice flowing through pipe 52 enters the heat exchanger 76 and is heated by heat transmitted from the liquid in pipe 79. It should be understood that within each of the heat exchangers 76 and 77 there is at least one heater core or radiator for effecting the transmittal of heat between the respective fluids in the pipes 52 and 79, and 78 and the pipe 79. The simplified depiction of the heat exchangers 76 and 77 in FIG. 9 is provided only to show the separation of fluids and not the actual design of such well known heat exchangers.

A temperature sensor 205 within the heat exchanger 76 monitors the temperature of the green juice flowing out of the heat exchanger 76. The temperature sensor 205 is connected to the computer 500 shown in FIG. 19. The flow of the green juice through the heat exchanger 76 is known from the flow-meter 54 and controlled via the pump 70 and valve $V_1$. Ideally the flow of green juice is maintained at a constant predetermined rate, for instance, 20 gallons per minute or a range of between 15 and 30 gallons per minute. Further, the flow of water re-circulating through the second heat exchanger 77 via the pipe 79 is controlled by the pump $P_3$ thereby providing a means for selectively controlling the amount of heat provided by the water flowing from the second heat exchanger 77 to the heat exchanger 76 and subsequently to green juice. In other words, by controlling the flow of water through the heat exchanger 77, the amount of heat provided to the green juice flowing through the heat exchanger 76 is controlled.

If a problem is detected by the computer 500 in the heating stages of the processing in the automated processing apparatus of the present invention, a valve $V_2$ is provided in the pipe 52 downstream of the heat exchanger 76. The valve $V_2$ is connected to the pipe 52, a pipe 80 and a waste pipe W. The position of the valve $V_2$ is electronically controlled by the computer 500 such that in normal operation, the valve $V_2$ allows heated green juice to flow from the heat exchanger 76 through the pipe 52 and into the pipe 80 and on to other portions of the automated processing apparatus. However, if a problem is detected by the computer 500, the valve $V_2$ is positioned to cause flow of green juice to go to the waste pipe W and a valve $V_W$ in the pipe 52 allows fresh water from the pipe 112 to flow into the heat exchanger 76, thereby rinsing and flushing out the heat exchanger 76. For instance, if the sensor 205 sends signals to the computer 500 indicating that the green juice has been heated above a predetermined threshold temperature, then the overheated portion of the green juice may be discarded by diversion to the waste pipe W and the heat exchanger 76 flushed out and cooled with fresh water prior to resumption of the green juice heating process.

Figure 10:
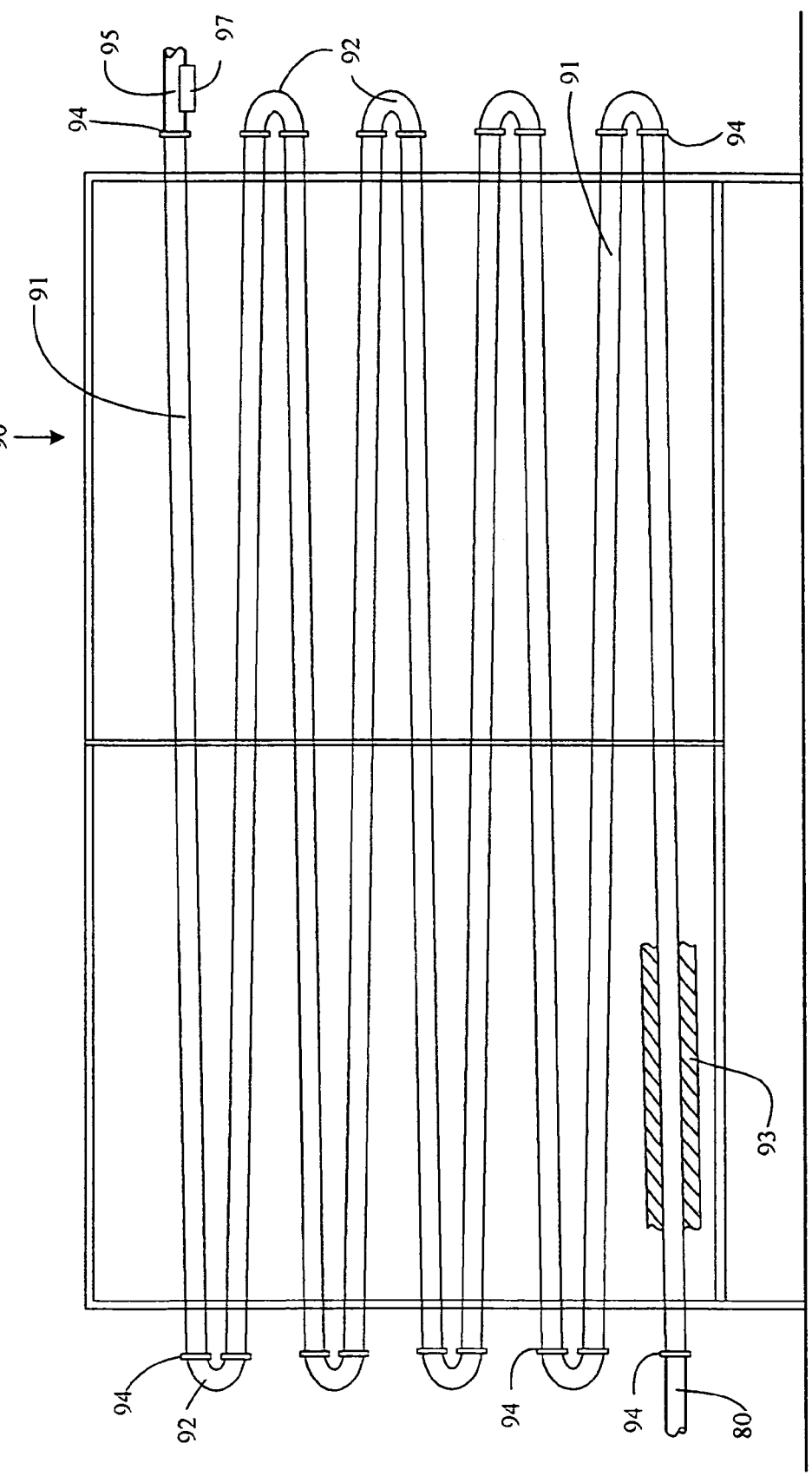

The pipe 80 connected to the valve $V_2$ is further connected to a heat retaining pipe assembly 90 shown in FIG. 10. The heated and pH adjusted juice exits the heater assembly 75 via the pipe 80 and enters the heat retaining pipe assembly 90. The pipe assembly 90 includes a plurality of pipes 91 and a plurality of detachable elbows 92. Each of the pipes 91 is wrapped or otherwise covered with heat insulation 93. However, for clarity and simplification of the drawing, only a small portion of the heat insulation 93 is shown in FIG. 10. The pipes 91 are further slightly inclined in order to facilitate connection to the elbows 92, as depicted in FIG. 10. Further, the inclination of the pipes allows for air to rise to the top most pipe 91 thereby permitting the heated juice to completely fill the heat retaining pipe assembly 90 and ensure that the juice remains at the desired temperature throughout passage through the pipes 91 without interference from air bubbles. An air bleeding valve (not shown) may also be provided at the top of the heat retaining pipe assembly 90 to permit removal of air pockets. Further, the inclination of the pipes 91 ensures proper drainage of the pipes after cleaning. It should be understood that although only nine pipes 91 are shown, any number of pipes may be coupled together by the elbows 92 in order to facilitate an appropriate length of heat retention piping.

The elbows 92 and the pipes 80, 91 and 95 are formed with mating flanges 94 such that the various elbows and pipes can be connected to one another in a versatile manner. For instance, in the pipe configuration depicted in FIG. 10, the pipe 80 is connected to the lowest pipe 91 in the pipe assembly 90 and the pipe 95 is connected to the upper most, with all intermediate pipes 91 being connected in series by elbows 92 to define a lengthy continuous flow path for the green juice. Therefore, as heated green juice enters the pipe assembly 90 from pipe 80, the green juice is retained in a heat insulated environment throughout the length of all of the assembled pipes 91. Alternatively, the pipe 95 may be connected to any one of the other pipes 91 with an appropriate removal of one of the elbows 92, thereby shortening the flow path of the green juice. As mentioned above, there may be an infinite number of pipes making it possible to lengthen the flow path of the green juice as necessary. The length of the heat retention piping is calculated by determining the time interval the juice is to be maintained at a predetermined temperature and the rate of flow of the juice through the heat retention piping. Therefore, the above described configuration provides a flexible system for pH treatment and heating juice in a variety of predetermined parameters. By selectively coupling a predetermined number of the pipes 91 together with an appropriate number of elbows 92, the flow path of the green juice may be shortened or lengthened accordingly.

A temperature sensor 97 is provided in pipe 95 (FIG. 10) to monitor the temperature of the heated green juice leaving the heat retaining pipe assembly 90. The temperature sensor 97 is connected to the computer 500 so that the computer 500 monitors the temperature of the green juice.

Figure 11:
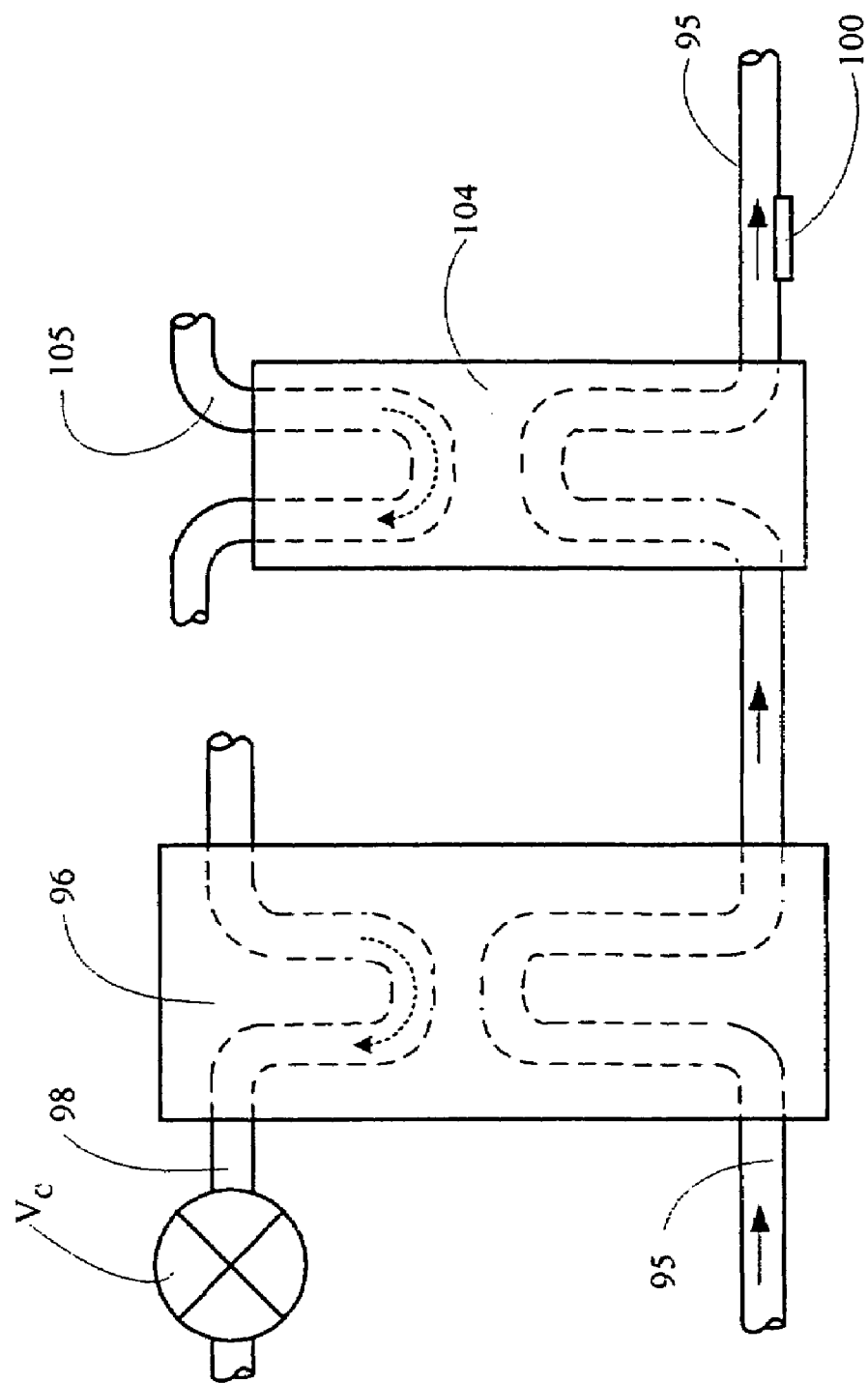

As shown in FIG. 11, upon exiting the pipe assembly 90 via the pipe 95, the heated green juice enters a first cooler 96 (heat exchanger) that is supplied with tap water via a pipe 98 to cool the green juice. Flow of the tap water is controlled by a valve $V_C$ that is connected to the computer 500. The green juice then passes through a second cooler 104 supplied with chilled water via a pipe 105. The chilled water in the pipe 105 is chilled by a remote chiller (not shown) to a predetermined temperature of between 40° and 60° C., but preferable about 50° C. A temperature sensor 100 in the pipe 95 downstream from the second cooler 104 monitors the temperature of the chilled juice and is connected to the computer 500.

Figure 12:
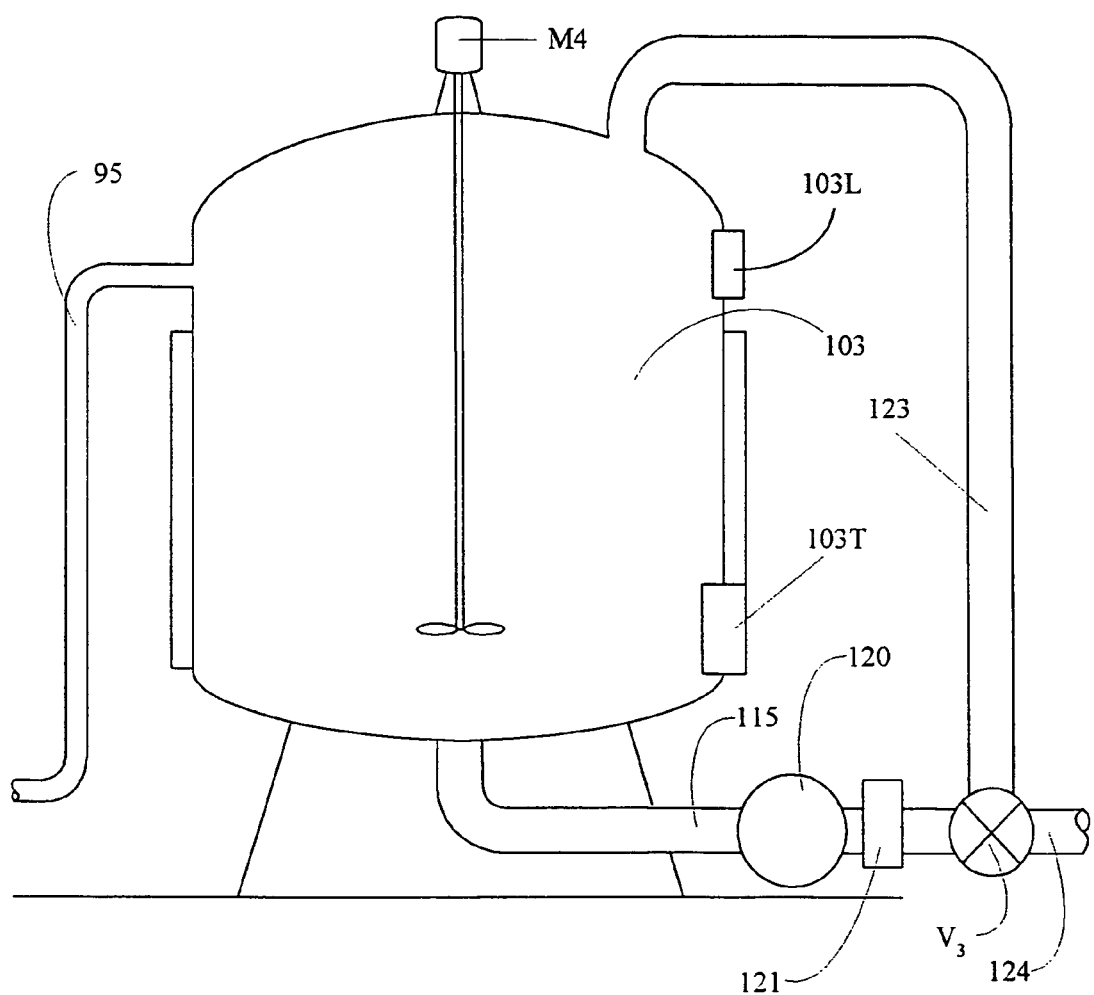
Figure 16:
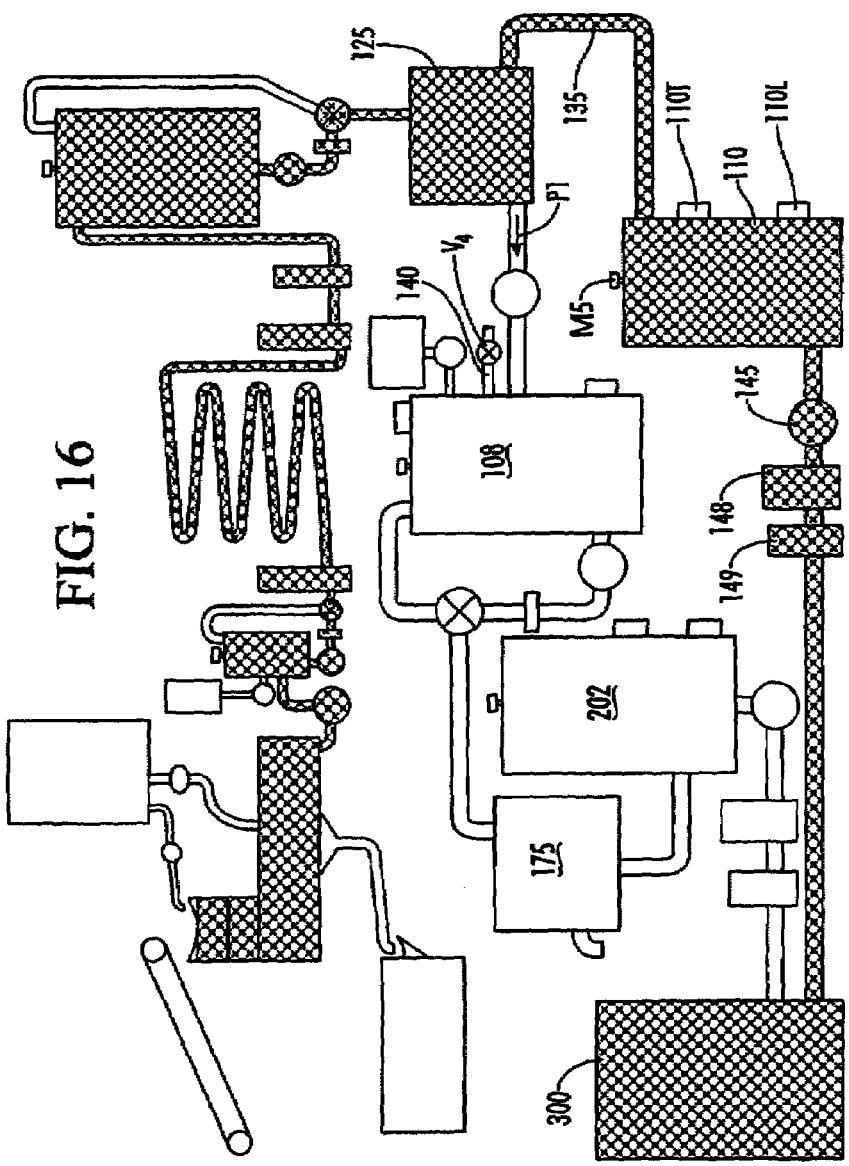
FIG. 16 is another schematic chart, similar to FIG. 15, showing a representation of the flow of a portion of the plant material processed by the automated processing apparatus depicted in FIG. 2, in accordance with the present invention.
Figure 17:
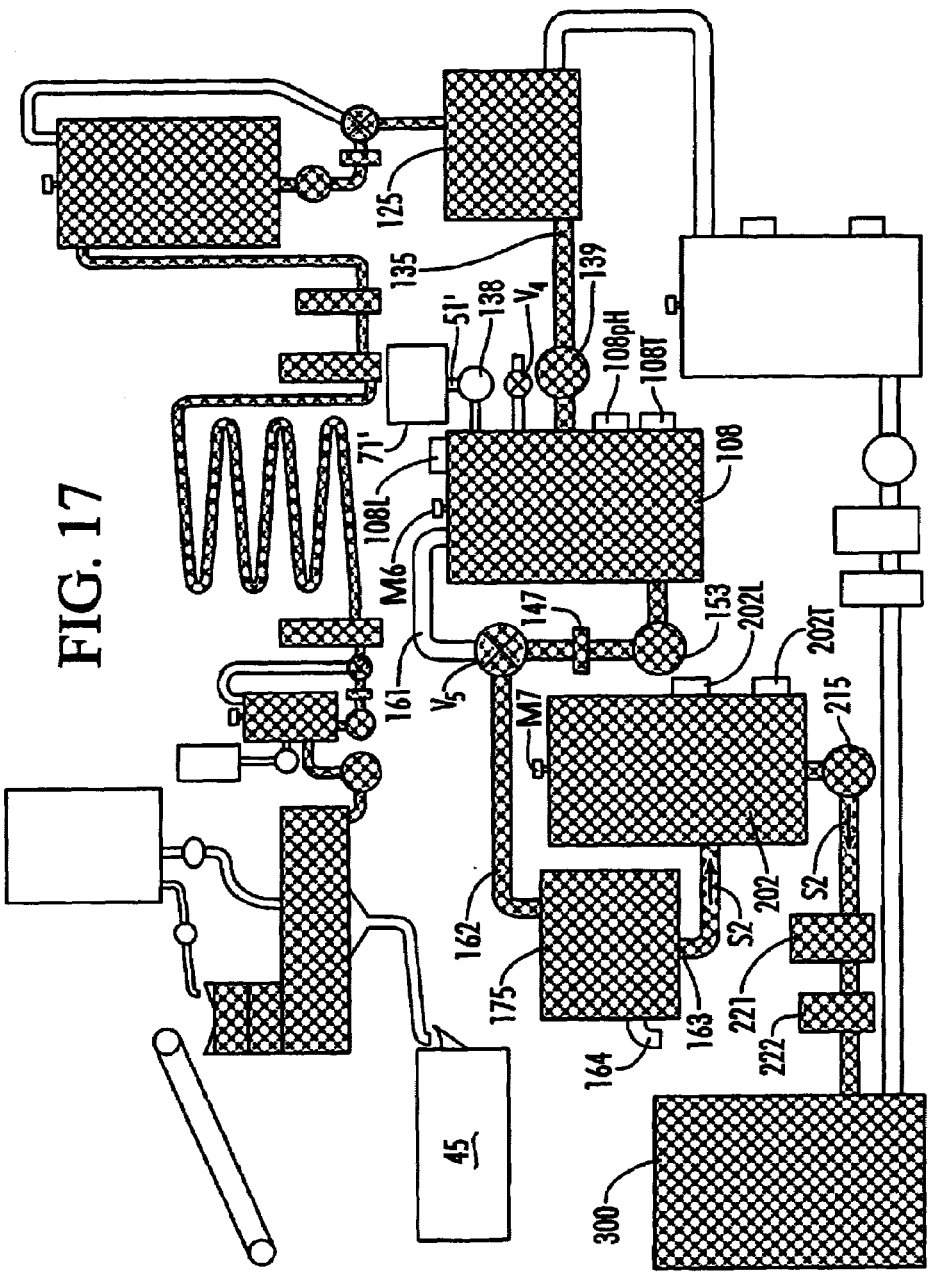
FIG. 17 is another schematic chart, similar to FIGS. 15 and 16, showing a partial representation of the flow of another portion of the plant material processed by the automated processing apparatus depicted in FIG. 2, in accordance with the present invention.
Figure 18:
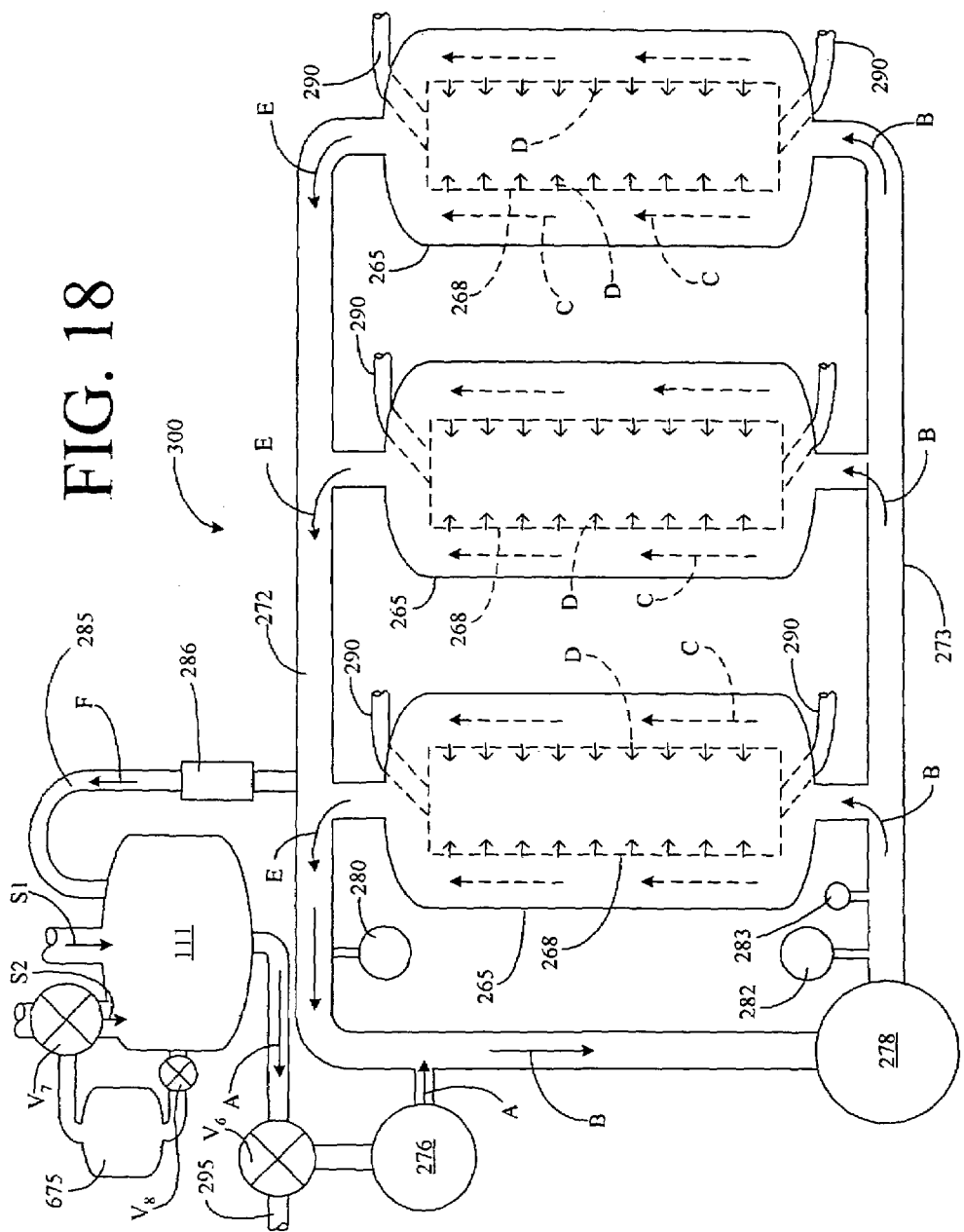
FIG. 18 is a schematic side view of an ultrafiltration system of the automated processing apparatus depicted in FIG. 2, in accordance with the present invention.

After leaving the second cooler 104, the chilled green juice then flows to a first surge tank 103 shown in FIGS. 2, 12 and schematically in FIG. 16, 17 and 18.

From the tank 102 to the tank 103 flow of the green juice is effected by the pump 70 described above with respect to the description of the tank 102 in FIG. 8. The pump 70 and valve $V_1$ provide control of the portions of the automated processing apparatus between the tank 102 and tank 103. For instance, if a problem is detected via one of the above described sensors, the valve $V_1$ is operable to revert the flow of green juice to re-circulation mode back into the tank 102, thereby isolating the green juice from the detected troubled element of the automated processing apparatus. For example, if the green juice is being over heated, flow to the heater is stopped by the valve $V_1$ operating in re-circulation mode, the heater assembly 75 can be flushed out removing damaged green juice via the waste pipe W and the process can be re-started.

Similarly, the tank 103 is also provided with a re-circulation loop, as is described below.

The tank 103 is equipped with a stirring mechanism powered by a motor M4 to keep the juice in a homogenized state thereby reducing the possibility of sedimentation. The tank 103 is further provided with a temperature sensor 103T that transmits temperature readings to the computer 500. The tank 103 is also provided with a level sensor 103L that senses the level of the green juice in the tank 103 and transmits the level information to the computer 500. It should be understood that the pipe 95, although shown in FIG. 12 with an inlet at the top if the tank 103, may be connected to the tank 103 at any location. Similarly, the temperature sensor 103T is shown near the base of the tank 103, but may be located at on any liquid contacting portion of the tank 103.

An outlet pipe 115 is connected to the bottom of the tank 103 for directing juice out of the tank 103 to a pump 120 that is controlled by the computer 500. Downstream from the pump 120 on the pipe 115 is a flow meter 121 that monitors the flow of juice pumped by the pump 120 from the tank 103. Further, a valve $V_3$ is installed downstream from the pump 120 and the flow meter 121 in order to control flow of juice from the tank 103 to a first centrifuge 125 shown in FIG. 13. The valve $V_3$ is connected to a re-circulation pipe 123 that diverts juice from the valve $V_3$ back into the tank 103 thereby definings another re-circulation loop. The valve $V_3$ is also connected to a pipe 124 that feeds the above mentioned first centrifuge 125.

The valve $V_3$ is operable to change flow of green juice out of the pipe 115 to flow into either the re-circulation pipe 123 or the pipe 124. In other words, the valve $V_3$ is operated to change flow of the juice out of the tank 103 so that the juice may be fed to the first centrifuge 125 or may be fed back into the tank 103 via the pipe 123. Operation of the first centrifuge 125 is such that flow of juice to the first centrifuge 125 must be periodically interrupted, as will be more clearly understood from the following description of the operation of the first centrifuge 125.

Juice enters the first centrifuge 125, shown in FIGS. 13 and 14, through the pipe 124. It should be understood that depiction of the location of the pipe 124 and other elements of the centrifuge 125, described further below, are purely schematic and are not intended to be dimensionally accurate.

The centrifuge 125 is a commercially available centrifuge, such as those manufactured by Westfalia Separator AG, a German company. In the automated processing system of the present invention, a Westfalia Separator centrifuge, model SAMR-15037 is used.

The centrifuge 125 is a solids discharging type centrifuge, similar to those described in, for instance, U.S. Pat. Nos 5,899,845, 5,267,937, 4,966,576 and 5,865,719 all assigned to Westfalia Separator AG. The centrifuge 125 includes a controller 126 electronically connected to the computer 500. The controller 126 controls water pressure that is selectively provided through a pipe 130 to a hydraulic actuator 132, as is described in greater detail below. The centrifuge 125 includes series of stacked conical shells 127a that are supported on a manifold 127b that diverts liquid from within the centrifuge 125 out through a pipe 135. The centrifuge 125 also includes an upper shell 128 and a lower shell 129 supported on a shaft 134.

Operation of the centrifuge 125 is controlled by the computer 500 in the following manner. The shaft 134 is powered by a motor (not shown) such that the upper and lower shells 128 and 129 rotate at a predetermined high rate of speed forcing pellet P1 radially outward against the radial surfaces of the upper and lower shells 128 and 129. At the same time, supernatant S1 is separated from the pellet P1 and the supernatant S1 travels upward along the surfaces of the stacked conical shells 127a into the manifold 127b and out the pipe 135. At predetermined intervals, the controller 126 is actuated introducing fluid pressure to the hydraulic actuator 132 forcing the upper and lower shells 128 and 129 apart (see FIG. 14) thereby allowing pellet P1 to be expelled from the centrifuge 125 via the pipe 133. The fluid pressure from the hydraulic actuator 132 is exhausted through a relief pipe 131 and the upper and lower shells 128 and 129 close for further separation of pellet P1 from supernatant S1. At those intervals where the pellet P1 is expelled from the centrifuge (FIG. 14) the flow of juice into the centrifuge 125 via the pipe 124 is interrupted by operation of the valve $V_3$ (FIG. 12) thereby causing juice to re-circulate back into the tank 103. The computer 500 is programmed to synchronously control both the operation of the centrifuge 125 and the valve $V_3$ in order to provide timely flows of juice and allow proper purging of pellet from the centrifuge 125 with minimal waste juice.

Operation of the centrifuge 125 involves a two stage operation. In the first stage, with the centrifuge bowl spinning the upper and lower shells 128 and 129 close (FIG. 13) and juice is fed into the centrifuge 125 via operation of the valve $V_3$. The operation the centrifuge 125 spins to impart a force of between 2500 G and 5000 G, but preferably at least 3000 G on the juice within causing pellet P1 to separate from the supernatant S1.

The pellet P1 moves to the radially outer portions of the centrifuge under such force. In the second stage of operation, the flow of juice into the centrifuge 125 is stopped by operation of the valve $V_3$, thereby causing the juice to re-circulate back into the tank 103. Further, via computer control, the shells 128 and 129 are opened thereby expelling the pellet P1 out the pipe 133. The duration of time the shells 128 and 129 are open is referred to as dwell time and is preprogrammed into the computer 500 in order to maximize expulsion of the semi-solid pellet P1.

In FIG. 14, the lower shell 129 is depicted as moving downward in response to fluid pressure introduced to the hydraulic actuator 132. It should be understood the present invention is not limited to the depiction of the centrifuge in FIGS. 13 and 14. Alternatively, the upper and lower shells 128 and 129 of the centrifuge 125 may be fixed in place and a baffle, piston or valve may be operated thereby providing a means for pellet P1 to exit the centrifuge 125.

Figure 15:
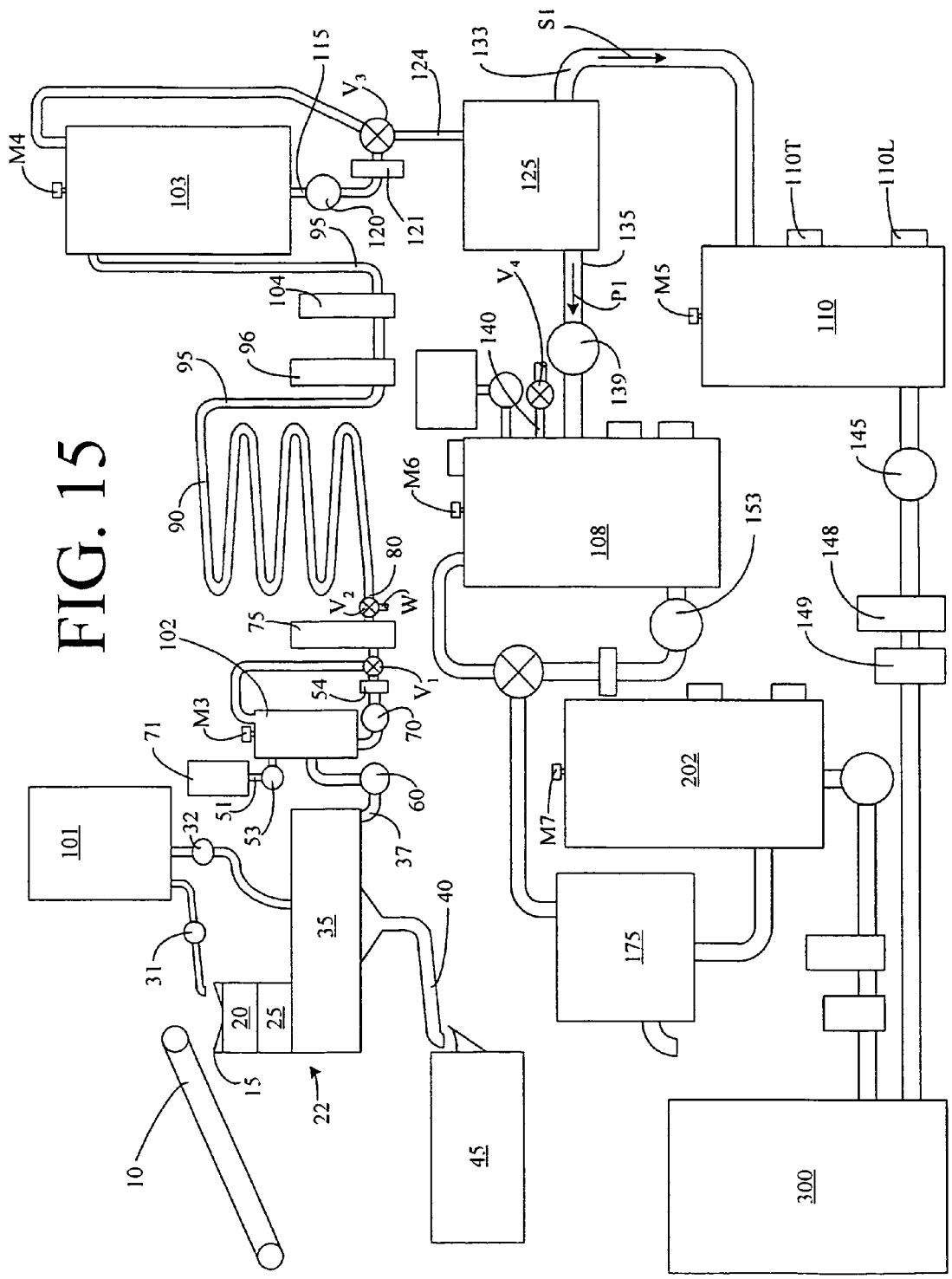

The elements of the present invention described above with respect to FIGS. 2–14 are depicted schematically in FIGS. 15, 16 and 17 along with additional elements of the automated processing system of the present invention. Attention is now turned to the relationships between the various elements of the present invention and their various interconnections and to the additional elements depicted in FIGS. 15, 16 and 17.

FIGS. 15, 16 and 17 are all schematic diagrams showing a representation of the various relationships and connections between the conveyor 10, the grinder and press apparatus 22, the dryer 45, the tank 102, the heater 75, the heat retention pipes 90, the coolers 96 and 104, the tank 103 and the centrifuge 125, each described above. It should be understood that the elements of the automated processing system of the present invention depicted in FIGS. 15, 16 and 17 are not dimensionally accurate but rather are merely representative of connections and interactions between the various elements shown therein. For instance, the tanks 101, 102, 103, 108, 110 and 202 may be the same size or alternatively, their respective sizes may vary depending upon production needs. Further, although not shown, each of the tanks 103, 108, 110 and 202 is provided with a water cooling jacket provided with chilled water to ensure that the juice in each of the tanks is maintained at a generally low temperature, for instance in the range of 20–45° C.

It should also be understood that the impeller blades of each agitator in each of the tanks 102, 103, 108, 110 and 202 is located at a position low in the tank but spaced apart from the bottom of the tank to maximize mixing and suspension of materials and to minimize formation of foam and aeration of liquid in each tank. Further, control by the computer 500 of the respective motors powering the agitators in each tank is effected in response to the level sensor in each tank. For instance, the agitator in the tank 102 is not provided with power by the computer 500 until the liquid level within the tank 102 reaches a minimum level. Further, for some of the tanks, such as tanks 102 and 108, the speed of the agitator impeller is determined by the computer 500 based upon the level of liquid within each respective tank. For instance if the level of liquid within the tank 102 is above a predetermined level a faster agitator speed may be desirable and if the level of liquid is below a predetermined level, a slower agitator speed may be desirable in order to further minimize foaming.

As shown in FIGS. 15, 16 and 17, the tank 101 is provided in the automated processing apparatus of the present invention for selectively supplying liquid to either or both of the first grinder 20 and press 35. For instance liquid from the tank 101 is supplied to the pipe 39 (FIG. 3) in the press 35. Liquid to bio-matter ratios are important during operation of the automated processing system of the present invention to ensure proper disintegration of the bio-matter. For example, in the case where a leafy bio-matter such as tobacco is being processed, additional liquid may be necessary to ensure proper suspension in liquid of the desired material of interest. Such liquid is added to the first grinder 20 and/or press 35. However, if too much liquid added during the grinding process, then later steps in the process may result in a less than optimal product. Therefore, a bio-matter/liquid ratio is predetermined for the bio-matter being processed. As the bio-matter is fed to the grinder and press apparatus 22, an appropriate flow of liquid is added to the grinder 20 and press 35 as pre-programmed into the computer 500.

Typically, the tank 101 is typically supplied with de-ionized water, distilled water or the like but alternatively includes a salt that serves as a buffering agent. Liquid from the tank 101 is fed into one or both of the grinder and the press via pumps 31 and 32 depending upon the nature of the harvested material or bio-matter. The pumps 31 and 32 are controlled by the computer 500. The liquid in the tank 101 alternatively has mixed therein any one of the following: salt (buffer); an anti-oxidant to prevent oxidation of the harvested material; a detergent to protect the protein of interest; a detergent to solublize the protein of interest; a chelating agent; a protease inhibitor; or an osmoticom such as sucrose to give osmotic strength to the protein of interest. Although not shown in FIGS. 15, 16 and 17, the tank 101 is equipped with a motor and agitator similar to the motor and agitator in the tanks 102 and 103 as described above.

Bio-matter fed to the grinder and press apparatus 22 via the conveyer 10 is disintegrated in order to maximize cellular disruption. Specifically, the inventors have determined that for tobacco plants approximately 95% of the cells of the bio-matter disintegrated by the grinder and press apparatus 22 are disrupted thereby releasing the material of interest for processing in subsequent steps by the automated processing apparatus of the present invention. The combination of the first grinder 20, the second grinder 25 and the press 35 maximizes cell disruption thereby ensuring a greater yield of the material of interest.

As described above, solid waste from the grinder and press apparatus 22 is taken from the press 35 to the dryer 45 via a conveyer 40, as depicted schematically in FIG. 15. Green juice from the press 35 is pumped through the pipe 37 via the pump 60 to the pH adjusting tank 102. In the pH adjusting tank 102, the green juice is treated with a pH adjusting material fed from the tank 71 via a pipe 51. The amount of pH adjusting material provided from the tank 71 to the tank 102 is manipulated by operation of the pump 53, which is controlled by the computer 500 in response to signals from the pH sensor 102 pH (FIG. 8), the flow meter 54 and the level sensor 102L.

Green juice in the tank 102 is selectively circulated out and back into the tank 102 via operation of the pump 70, the valve $V_1$ and pipe 55 (FIGS. 8 and 15). Re-circulation of the green juice through the pipe 55 and the stirring action of the agitator controlled by the motor M3 ensures uniform pH and consistency of the green juice in the tank 102.

The level sensor 102L sends signals to the computer 500 to indicate the level of green juice within the tank 102. The level signal in combination with the pH signal from the pH sensor 102 pH are important for determining the amount of pH adjusting material to be added to the tank 102. Once the level of the tank 102 reaches a predetermined level, the valve $V_1$ is manipulated by the computer to allow the flow of green juice from the pH adjusting tank 102 out the pipe 52 to the heater 75.

The flow of green juice into the pH adjusting tank 102 from the grinder and press apparatus 22 and flow of green juice out of the tank 102 puts processing demands on the computer 500 with respect to proper pH adjustment. Specifically, when the automated processing system is up and running, and green juice flows in and out of the tank 102, a dynamic adjustment of pH in the tank 102 is required. The computer 500 is programmed to respond to combinations of: changes in level of green juice in the tank 102; signals from the flow-meter 54 indicating the amount of green juice exiting the tank 102; and the adjustment position of the valve $V_1$ allowing flow to the heater 75 (or re-circulation of green juice back into the tank 102) in order to continuously adjust the pH of the green juice in the tank 102. Specifically, adjustment of the pH in the green juice is a dynamic operation with the valve $V_1$ allowing flow to the heater 75 because fresh untreated green juice is typically entering the tank 102 from the grinder and press apparatus 22 and leaving the tank 102 via the pipe 52. Therefore, the pH adjustment of the green juice is always in flux and must be continuously monitored.

After pH adjustment, green juice flows away from the tank 102 via the pipe 52 to the heater 75, as described above with respect to FIG. 9. The re-circulation capabilities effected by inclusion of the valve $V_1$ and re-circulation pipe 55 at the tank 102 serve several purposes. If the heater 75 is malfunctioning, or is not providing heat within predetermined parameters, the valve $V_1$ is operated by the computer 500 and set so that the green juice re-circulates to the tank 102. As mentioned above, if the green juice is heated to a temperature that might damage the material of interest, the green juice affected may be discarded out the waste pipe W via operation of the valve $V_2$ controlled by the computer 500, and the heat exchanger 76 flushed with fresh water to clean that portion of the system and cool the heat exchanger 76.

Next, as shown in FIG. 15, green juice flows from the heater 75 into the heat retention pipes 90, through the pipe 95, to the cooler 96, through the chiller 104, and then into the tank 103, all described previously.

Like the tank 102, the tank 103 includes a re-circulation system with the valve $V_3$ and re-circulation pipe 123. The valve $V_3$ is selectively operated by the computer 500 to control the feed of green juice into the centrifuge 125. Specifically, the computer 500 operates the valve $V_3$ to stop the flow of green juice to the centrifuge 125 for a time period corresponding to the above described dwell time, where solids are expelled from the centrifuge 125.

In the centrifuge 125, the green juice is separated by centrifugal forces into pellet P1 (semi-solid material) and supernatant (liquid material). From the centrifuge 125, two separate flow paths are defined, one path defined by the flow of supernatant S1 out of the centrifuge 125, as depicted in gray in FIG. 16, and one path defined by the flow of pellet P1 out of the centrifuge as depicted in gray in FIG. 17. Description is first provided for the flow path of the supernatant S1 with reference to FIG. 16.

The supernatant S1 exhausted from the centrifuge 125 passes through the pipe 133 to a tank 110, shown in FIG. 16. The tank 110 is provided with a temperature sensor 110T, a level sensor 110L and an agitator (not shown) powered by a motor M5, each being connected to the computer 500. The agitator powered by the motor M5 is, for instance, for the purpose of minimizing or preventing precipitation of any remaining particulate matter in the supernatant S1. The tank 110 serves as a holding tank for the supernatant S1 Structurally, the tank 110 is generally similar or the same as the tank 103 depicted in FIG. 12.

From the tank 110, the supernatant S1 is directed via a pump 145 through a first filter 148 and a second filter 149. The first and second filters 148 and 149 are configured to remove particles larger than a predetermined size, depending upon the bio-matter being processed by the automated processing apparatus of the present invention. For instance, in the instance where virus is being processed from tobacco plants, the first filter 148 is set to remove particles having a size greater than 100 microns and the second filter 149 is set to remove particles having a size greater than 50 microns. However, it should be understood that the filtration step performed by the first and second filters 148 and 149 is dependent upon the protein, virus or bio-matter being processed and the filters 148 and 149 are not limited to the 100 micron and 50 micron size restrictions mentioned above. Larger or smaller size filters are installable in accordance with the material being processed. Further, in some processing applications of the present invention, only one filter may be necessary. Two filters are employed at this stage of the automated processing apparatus of the present invention to minimize the possibility of one or the other filters becoming restricted or clogged with matter greater than the determined filtration size.

After passing through the filters 148 and 149, the supernatant then passes to an ultra filtration device 300 that is described in greater detail below with respect to FIG. 18.

The flow of the pellet P1 out of the centrifuge 125 is now described with reference to FIG. 17. The pipe 135 directs the flow of pellet P1 out of the centrifuge 125 to a pump 139 and into another tank 108. The pellet P1 is semi-solid or very thick slurry of material having been separated from the supernatant S1 by the centrifuge 125. Depending upon the bio-matter being processed and the material of interest being extracted, liquid may be added to the pellet P1 via opening and closing of a valve $V_4$ connected to a liquid feed and the tank 108. The valve $V_4$ may be connected to a tank (not shown) filled with de-ionized water or may alternatively be connected to the tank 101. The specific liquid added via control of valve $V_4$ depends upon the nature of the bio-matter being processed and the material of interest being extracted. Operation of the valve $V_4$ is controlled by the computer 500.

The tank 108 is generally serves the same purpose as the tank 102 depicted in FIG. 8 and includes a temperature sensor 108T, a level sensor 108L, a pH sensor 108pH and an agitator powered by a motor M5. The tank 108 includes a pH adjuster feed pipe 51' that is in turn connected to a pH feed tank 71' for selectively supplying a pH adjuster liquid into the tank 108 in a manner similar to that described above with respect to FIG. 8 and the pH feed tank 71. Specifically, a pump 138 controlled by the computer 500 selectively pumps pH adjusting material into the tank 108 in order to re-suspend the pellet P1. Like the tank 102, the tank 108 is connected to a pipe having a pump 153 that directs the re-suspended pellet P1 through a flow meter 147 and onward to a valve $V_5$. The flow meter 147, like the flow meter 54, is connected to the computer 500 providing signals indicating flow information of the re-suspended pellet P1. The valve $V_5$ is connected to a re-circulation pipe 161 and a pipe 162. The valve $V_5$ is operable via signals from the computer 500 to direct re-suspended pellet P1 back into the tank 108, or allow the re-suspended pellet P1 to flow to a second centrifuge 175.

In a manner similar to tank 102, the computer 500 processes signals from the pH sensor 108pH, the level sensor 108L and the flow meter 153 in order to re-circulate the re-suspended pellet P1 through the tank 108 in order to bring the pH level in the re-suspended pellet P1 to a predetermined level, and to progressively feed the re-suspended pellet P1 into the centrifuge 175.

However, in one operational embodiment of the automated processing system, the tank 108 is gradually filled during operation of the centrifuge 125. Typically, all of the pH adjusted, heated and cooled green juice is subjected to centrifugation in the centrifuge 125 before operation of the centrifuge 175 begins. Specifically, all of the pellet P1 is loaded into the tank 108 before operation of the centrifuge 175 begins. Therefore, the pellet P1 is processed as a batch, rather than being dynamically processed. A predetermined amount of liquid is added via the valve $V_4$ and then the pH is adjusted without further pellet P1 being loaded into the tank 108.

In many processing operations, the amount of pellet P1 loaded into the tank 108 is much less than the amount of green juice that flows through the tank 102. As described above, pH adjustment of the green juice in the tank 102 is a dynamic process that occurs with green juice flowing into the tank 102 and selectively flowing out of the tank 102. The action of the centrifuge 125 removes supernatant S1 from the pellet P1 in such a way that the amount of pellet P1 is ideally considerably less that the amount of supernatant S1. Consequently, in most processing operations, all of the pellet P1 is fed into the tank 108 and a predetermined amount of water and/or liquid is supplied via the valve $V_4$. Thereafter, pH adjustment is effected by addition of pH adjusting material via the pump 138. The amount of pellet P1 is predictable if the amount of bio-matter being processed is known. The amount of water and/or liquid supplied via the valve $V_4$ is easily calculated and amount of pH adjusting material is more easily added via the pump 138 because the pH adjusting process in the tank 108 is not always a dynamic operation when done in a batch. However, it should be understood that for extremely large processing volumes of bio-material, operation of the pH adjusting performed in tank 108 can be dynamic in a manner similar to pH adjustment in tank 102 with pellet P1 flowing into the tank 108 and pH adjusted pellet P1 selectively flowing out of the tank 108 via control of the valve $V_5$ and pump 153.

The centrifuge 175 is preferably similar, and may be identical to the centrifuge 125. Specifically, the centrifuge 175 operates in a manner generally the same as the centrifuge 175 separating the re-suspended pellet P1 into liquid and semi-solid portions, a supernatant S2 and pellet waste. The supernatant S2 is directed out of the centrifuge via a pipe 163 and into another tank 202. The pellet waste is directed out of the centrifuge 175 via a pipe 164 and is discarded.

The tank 202 includes a level sensor 202L, a temperature sensor 202T and an agitator powered by a motor M7. Operation of the motor M7 is effected by the computer 500. The sensors 202L and 202T are connected to the computer 500 sending signals thereto. The stirring mechanism powered by the motor M7 in tank 202 is, for instance, for the purpose of minimizing or preventing settling of any remaining particulate matter in the supernatant S2. A pump 215 downstream from the tank 202 provides control for flow of the supernatant S2 out of the tank 202 and through a third filter 221 and fourth filter 222. The pump 215 is connected to the computer 500, as shown in FIG. 19.

The third and fourth filters 221 and 222 are configured to remove particles larger than a predetermined size, depending upon the bio-matter being processed by the automated processing apparatus of the present invention. For instance, in the instance where tobacco mosaic virus is being processed from tobacco plants, the third filter 221 is set to remove particles having a size greater than 100 microns and the fourth filter 222 is set to remove particles having a size greater than 50 microns. However, it should be understood that the filtration step performed by the third and fourth filters 221 and 222 is dependent upon the protein, virus or bio-matter being processed. The filters 221 and 222 are not limited to the 100 micron and 50 micron size restrictions mentioned above. Further, in some processing applications of the present invention, only one filter may be necessary. Two filters are employed at this stage of the automated processing apparatus of the present invention to minimize the possibility of one or the other filters becoming restricted or clogged with matter greater than the determined filtration size.

After passing through the filters 221 and 222, the supernatant then passes to an ultra-filtration device 300 that is described in greater detail below with respect to FIG. 18.

After leaving the filter 149, the supernatant S1 flows to the ultrafiltration system 300, and more specifically into the tank 111 depicted in FIGS. 2 and 18. Further, the supernatant S2 upon passing through the filter 222 also flows into the tank 111 depicted in FIGS. 2 and 18.

Hereinafter the supernatants S1 and S2 now in the tank 111 are referred to as retentate for reasons which will become clearer in the description below of the ultrafiltration process.

Referring now to FIG. 18, the ultrafiltration system 300 is schematically depicted along with the above mentioned tank 111. The ultrafiltration system 300 includes at least one tangential flow filter unit 265. In the embodiment depicted in FIG. 18. the ultrafiltration system 300 includes three tangential flow filter units 265, however it should be understood that the number of tangential flow filter units is flexible and could be 6 or more in number. For some applications of the automated processing apparatus of the present invention only one unit 265 is necessary, for other applications a plurality of units 265 may be desirable. In other words the specific number of tangential flow filter units 265 is determined by the specific application of the present invention and the present invention is not limited to a configuration of three tangential flow filter units 265.

Each tangential flow filter unit 265 includes a membrane 268 that allows particles of a predetermined size to flow therethrough thereby defining a filtration threshold. For instance, in the case where supernatant from tobacco bio-matter infected with tobacco mosaic virus is being subjected to ultrafiltration, a membrane is employed that retains particles having a molecular weight of about 100 k or higher (retentate) and allows all particles having a molecular weight smaller than about 100 k to permeate the membrane 268 in a manner described in greater detail below. The predetermined filtration threshold (or permeability) in this example is 100 k molecular weight.

It should be understood that the molecular threshold of the ultrafiltration system 300 is not limited to 100 k molecular weight described above. For instance, for proteins, viruses and other matter processed from bio-matter other than the example mentioned above, a membrane having a different permeability may be more advantageous. For instance, processing of bio-matter harvested from corn or rice plants will likely require a different permeability requiring a different type of membrane. Examples of ultrafiltration systems and membranes for ultrafiltration systems are found in the following documents, which are incorporated herein by reference: U.S. Pat. Nos. 4,227,999, 6,106,715 and U.S. Pat. No. 6,120,688.

It should also be understood that tangential flow filter unit 265 and the membrane 268 may be any of a variety of configurations, not only the configuration depicted. For instance, a canister filter, spiral filter, plate and frame filter, ceramic filter or hollow fiber filter type arrangement may alternatively be used.

Each of the tangential flow filter units 265 in FIG. 18 is connected at a first end to a feed manifold 273 and at a second end to a retentate manifold 272. A pump 276 is selectively controlled to pump liquid from the tank 111 into the manifolds 272 and 273, as shown in FIG. 18. Another pump 278 causes the retentate to re-circulate through the tangential flow filter units 265 from the feed manifold 273 to the retentate manifold 272. A pressure gauge 282 is installed on the manifold 273 to monitor the pressure therein and another pressure gauge 280 is installed on the manifold 272. A temperature gauge 283 is also installed on the feed manifold 273 to monitor the temperature of the retentate. The pressure gauges 280 and 282 and the temperature gauge 283 are not connected to the computer 500, but in an alternate embodiment are connected to the computer to provide the measured parameters.

A pipe 285 is connected to the retentate manifold 272 in order to allow the retentate to flow back into the tank 111, as is described in greater detail below. The pipe 285 is provided with a flow meter 286.

A valve $V_6$ is provided downstream from the tank 111 just before the pump 276. The valve $V_6$ is controllable to direct retentate into the manifold 273 or to direct the retentate out a pipe 295 to storage vessels (not shown) for further processing outside the automated processing system of the present invention.

A pipe 95 and valve $V_6$ are connected to the tank 111 to allow concentrate (retentate with liquid removed as a result of being subjected to the ultrafiltration process) to leave the ultrafiltration system 300.

The ultrafiltration system 300 operates as follows. Retentate is pumped from the tank 111 by the pump 276 with the valve $V_6$ set to supply liquid into the manifold 273 as indicated in FIG. 18 by the arrows A. The pump 278, when operating, circulates the retentate from the manifold 272 into the manifold 273 as indicated by the arrows B. Therefore, the pressure within the manifold 273 is typically greater than the pressure in the manifold 272 causing the retentate in the manifold 273 to flow through the tangential flow filter units 265 as indicated by the dashed lined arrows C. As the retentate flows tangentially past the membranes 268, those molecules having a molecular weight below the predetermined threshold pass through the membrane 268 and exit through the pipes 290 as indicated in FIG. 18 by the small arrows D. For instance, excess water typically permeates the membrane 268 and passes out of the pipes 290. Larger molecules are retained in the retentate passing through the tangential flow filter units 265. Since the retentate is flowing tangentially along the length of the membranes 268, the likelihood of clogging the membrane 268 is reduced. The retentate exits the tangential flow filter units 265 and returns to the manifold 272 as indicated by the arrows E.

At predetermined intervals, a portion of the retentate is allowed to flow from the manifold 272 into the pipe 285 under the control of the flow meter 286 thereby mixing with portions of the retentate remaining in the tank 111, as indicated by the arrow F. The flow from the manifold 272 back into the tank 111 assists in the ultrafiltration process by maintaining a more homogenous retentate, and preventing the re-circulating retentate from becoming too concentrated to the point where, for instance, proteins might precipitate or the viscosity of the retentate becomes to greater than a desired level. The flow meter 286 may be manually controlled or alternatively may be connected to the computer 500 for automated control.

As the ultrafiltration process continues, the desired concentration of the retentate eventually is attained. At this point, the ultrafiltration process is stopped and the retentate is pumped from the tank 111 via a pump (not shown) through the pipe 295 with the valve $V_6$ manipulated to allow flow through the pipe 295.

In most processing operations, both the supernatant S1 and supernatant S2 are fed directly into the tank 111. Alternatively, the supernatant S2 may be subjected to ultrafiltration separately from the supernatant S1, for instance, in processing procedures where a first material of interest is to be extracted from the supernatant S1 and a separate material of interest is to be extracted from the supernatant S2. In such cases, a valve $V_7$ (shown in FIG. 18) is installed upstream from the tank 111 in order to divert the supernatant S2 into a holding tank 675. After ultrafiltration of the supernatant S1 and thorough cleaning of the ultrafiltration system 300, the supernatant S2 may be subjected to ultrafiltration and/or may be processed in other ways, depending upon the desired material of interest by opening valve $V_8$, shown in FIG. 18. Although not shown in FIG. 19B, the valves $V_7$ and $V_8$ may be connected to and controlled by the computer 500 or may be manually operated.

It should be understood that using the automated processing apparatus of the present invention it is possible to extract a material of interest from the supernatant S1, and also extract the same material of interest from the supernatant S2. However, it is also possible to extract a first material of interest from the supernatant S1 and a second separate material of interest from the supernatant S2, as is clearly shown in FIG. 1.

As indicated in FIG. 1, after ultrafiltration the retentate may be subjected to further processing, such as PEG precipitation or other types of purification to yield the desired product (for instance, see FIG. 1 steps M or J). Such processing is not necessarily automated and is separate from the automated processing apparatus of the present invention. For instance, the target species, either virus or protein/peptide, after separation from other components of the green juice by one or more cycles of centrifugation, re-suspension, and ultrafiltration, may further be purified by such procedure as PEG-precipitation or purifying proteins and peptides by such procedures as chromatography, including affinity separation, and/or salt precipitation.

The automated processing apparatus of the present invention is controlled from a single computer 500 that is housed in, for instance, the control room 490 depicted in FIG. 2. The computer 500, shown schematically in FIG. 19 (FIGS. 19A and 19B), is connected to many peripheral devices, such as a monitor, a printer, a keyboard, mouse or other digitizing device and an I/O device. The computer 500 includes storage devices such as a hard drive, removable disk drive devices, tape recording devices, or the like. As described above, the computer 500 is further connected to various sensors, motors and valves to monitor and control each of the various portions of the automated processing system via a programmable logic controller (PLC). The computer 500 is further connected to a plurality of nodes, node 1 through node N, each node being a supervisory control and data acquisition (SCADA) station, such as a personal computer. Each of the nodes 1 through N are located at strategic positions around the automated processing apparatus. For instance, one node is located proximate to the grinding and pressing apparatus 22, another node located proximate the centrifuge 125, etc. Specifically a node is located proximate each of the major components of the automated processing apparatus to enable local servicing of that component of the system. Computer control of the automated processing system is described below with reference to FIGS. 19–30.

The depiction of the connections between the computer 500 and the various sensors and motors is schematic in nature and does not include the typical relays and intermediate connections necessary for communication between mechanical devices and a computer well known in the art.

Several devices such as the conveyor 5, the pumps 276 and 278, valve $V_6$, flowmeter 286 and weigh belts 475 (an optional part of the conveyor 10), are shown in FIG. 19 in dashed line boxes to indicate that these elements are optionally connected to the computer 500 in an alternate embodiment.

Figure 20:
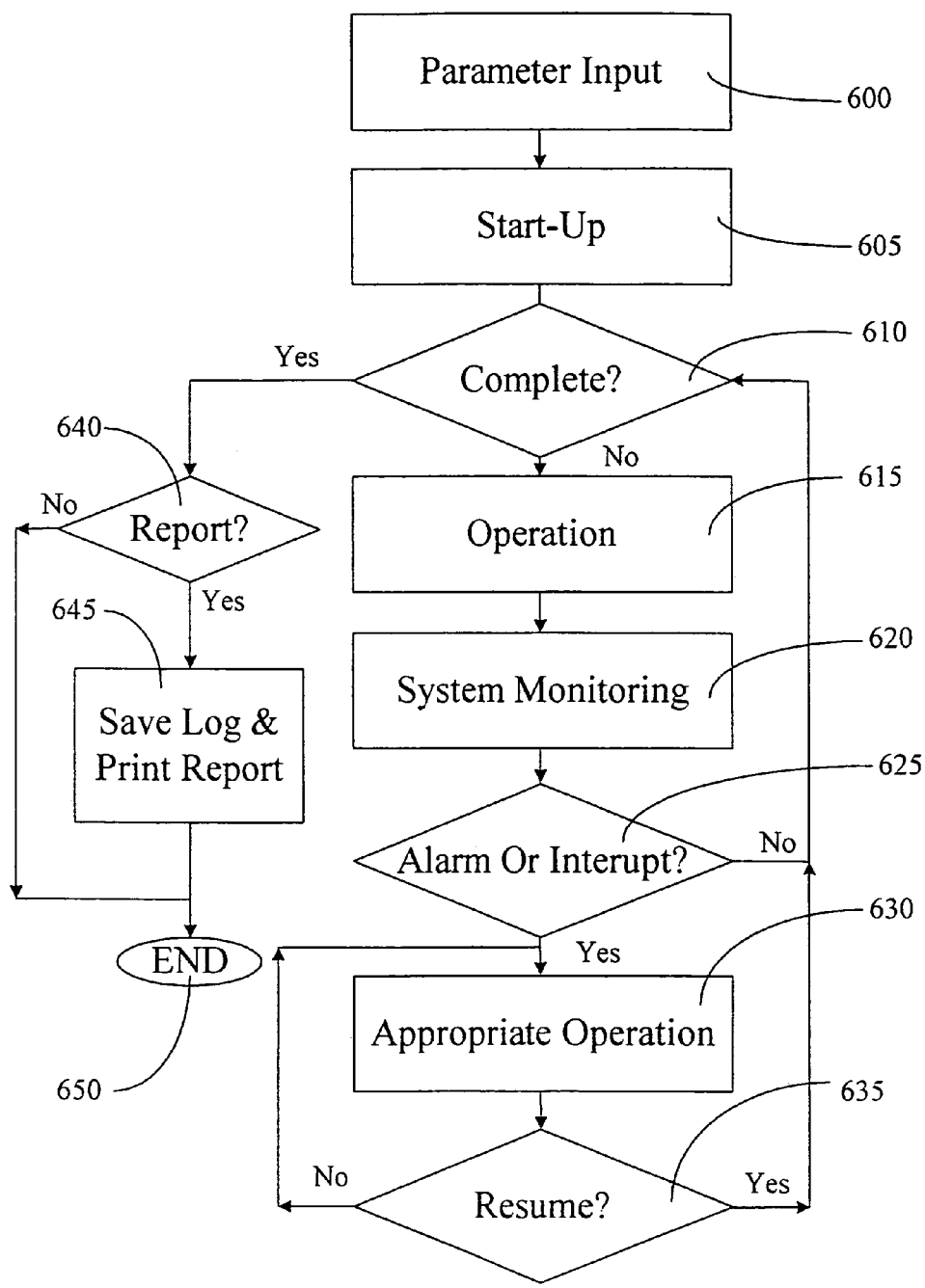
FIG. 20 is a flowchart showing basic operational steps of a computer system that monitor and control various portions of the automated processing apparatus of the present invention.
Figure 21:
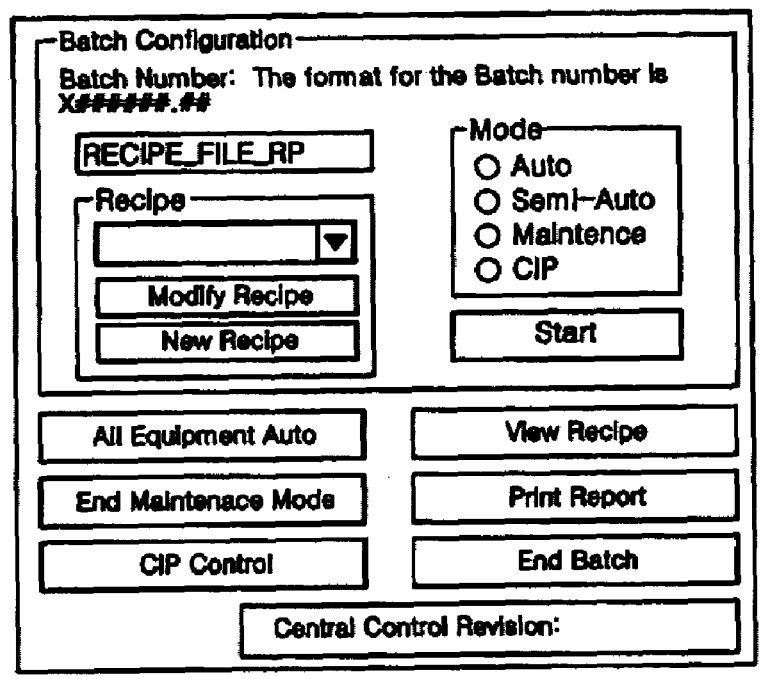
FIG. 21 is a representation of a central control screen displayed on a monitor of the computer depicted in FIG. 19, one of many computer images utilized in the automated control of the automated processing apparatus depicted in FIG. 2, in accordance with the present invention.

FIG. 20 is a flowchart showing one embodiment of operating steps of the computer 500. For instance, upon start-up (or restart) parameters of a predetermined processing sequence or batch are inputted, as represented by box 600 in FIG. 20. FIG. 21 shows a CENTRAL CONTROL screen displayed on the monitor of the computer 500 for parameter input. The CENTRAL CONTROL screen may be displayed at any time during the operation of the automated processing apparatus of the present invention by clicking (using a digitizer such as a mouse) on a CENTRAL CONTROL button displayed on each screen displayed on the monitor of the computer 500 (see FIGS. 24–30 near the lower right hand corner). From the CENTRAL CONTROL screen, a previously stored recipe having parameters of a batch may be recalled and run or modified. Various other preprogrammed controls are accessible from the CENTRAL CONTROL screen, such as the mode of operation of the automated processing system. Specifically, the automated processing system may be operated in: a fully automated mode, a semi-automated mode where elements of the automated processing apparatus are manually manipulated, while others continue under the control of the computer 500; a maintenance mode where individual portions of the automated processing apparatus may be manually started and stopped for servicing; and a CIP (clean in place) mode where cleaning water feeds (not shown) are engaged to automatically clean and rinse each of the various mechanical elements of the system.

From the CENTRAL CONTROL screen it is also possible to create a new recipe. It is also possible to change the mode of operation to make all equipment operate in an automatic mode, end the maintenance mode, access a CIP control panel (not shown), view the current recipe, print a report of all parameters of a completed processing batch, and end a particular batch.

If the New Recipe button is pressed on the CENTRAL CONTROL screen, the monitor of the computer 500 displays the RECIPE screen shown in FIG. 22. The RECIPE screen provides access to a variety of tabs, each tab associated with a plurality of parameters that are displayed for data input. The tabs include: Sol Prep (solution preparation); GJ Extract (green juice extraction); pH Adjustment; Heat Treatment; Centrifuge 1, Centrifuge 2, and Ultrafiltration. It should be recognized that in FIG. 22, the parameters for all of the tabs is displayed together as a group only for the purposes of the instant document, and that when each tab is chosen (via mouse click) only the parameters for that tab are displayed.

Specifically, if the tab Sol Preparation is selected, the parameters for the solution in the tank 101 are displayed for data input. The parameters for the tank 101 include: Water Flow To Disintegrator (in liters per minute); Water Flow To Press (also in liters per minute) Agitator Speed (for the agitator in the tank 101); Tank 101 Mix Time, for setting the length of time deemed necessary to dissolve a determined amount of buffering agent in solution within the tank 101 based upon the amount of bio-matter to be processed; and Concentration of Buffer (in grams per liter).

For the GJ Extract tab, the following parameters are displayed for data input: Grinder 1 Speed (grinder 20); and optionally (but not shown) Grinder 2 Speed (grinder 25).

For the pH Adjustment tab in FIG. 22, the following parameters are displayed for data input: Ideal pH in Tank 102 (in pH×100 units); Agitator 102 Speed (speed of agitator in tank 102); and Pump 102 Flow Rate (rate of pump 70 drawing green juice out of the tank 102 in litters per minute).

If the heat treatment tab in FIG. 22 is selected, the following parameters are displayed: Temp. Setpoint For Hold Tube (in ° C.); Max Hold Time (in minutes); and Holding Tube Configuration. The holding tube configurations are pre-programmed based, for instance, upon the number of pipes 91 connected together to define the length of the green juice heat retention path (described above with respect to FIG. 10).

If the Centrifuge 1 tab in FIG. 22 is selected, the following parameters are displayed: Agitator 103 Speed Output (for speed of agitator in the tank 103); Agitator 110 Speed Output (for speed of agitator in the tank 110); Green Juice Flow To Centrifuge 1 (in liters per minute); Centrifuge 1 Shot Frequency (for dwell time on the centrifuge, i.e. time duration for expulsion of semi-solid material in seconds); and the Recipe Type.

If the Centrifuge 2 tab in FIG. 22 is selected, the following parameters are displayed: Ideal pH in Tank 108; Agitator 108 Speed Output (for speed of agitator in the tank 108); Agitator 202 Speed Output (for speed of agitator in the tank 202); Green Juice Flow To Centrifuge 2 (in liters per minute); Centrifuge 2 Shot Frequency (for dwell time on the centrifuge, i.e. time duration for expulsion of semi-solid material in seconds); Tank 108 Initial Make-Up of Water (based upon predicted amount of pellet P1); and Tank 108 Fill Water % of Green Juice (operator enters a percentage and computer 500 calculates tank 108 Fill Water amount based upon amount of green juice processed based upon measurements from flowmeter 54).

In the depicted embodiment, the Ultrafiltration tab in FIG. 22 has no parameters to display. However, in an alternate embodiment, the Ultrafiltration tab includes the parameter: Concentration Factor to set the desired concentration of the retentate (not shown).

Figure 23:
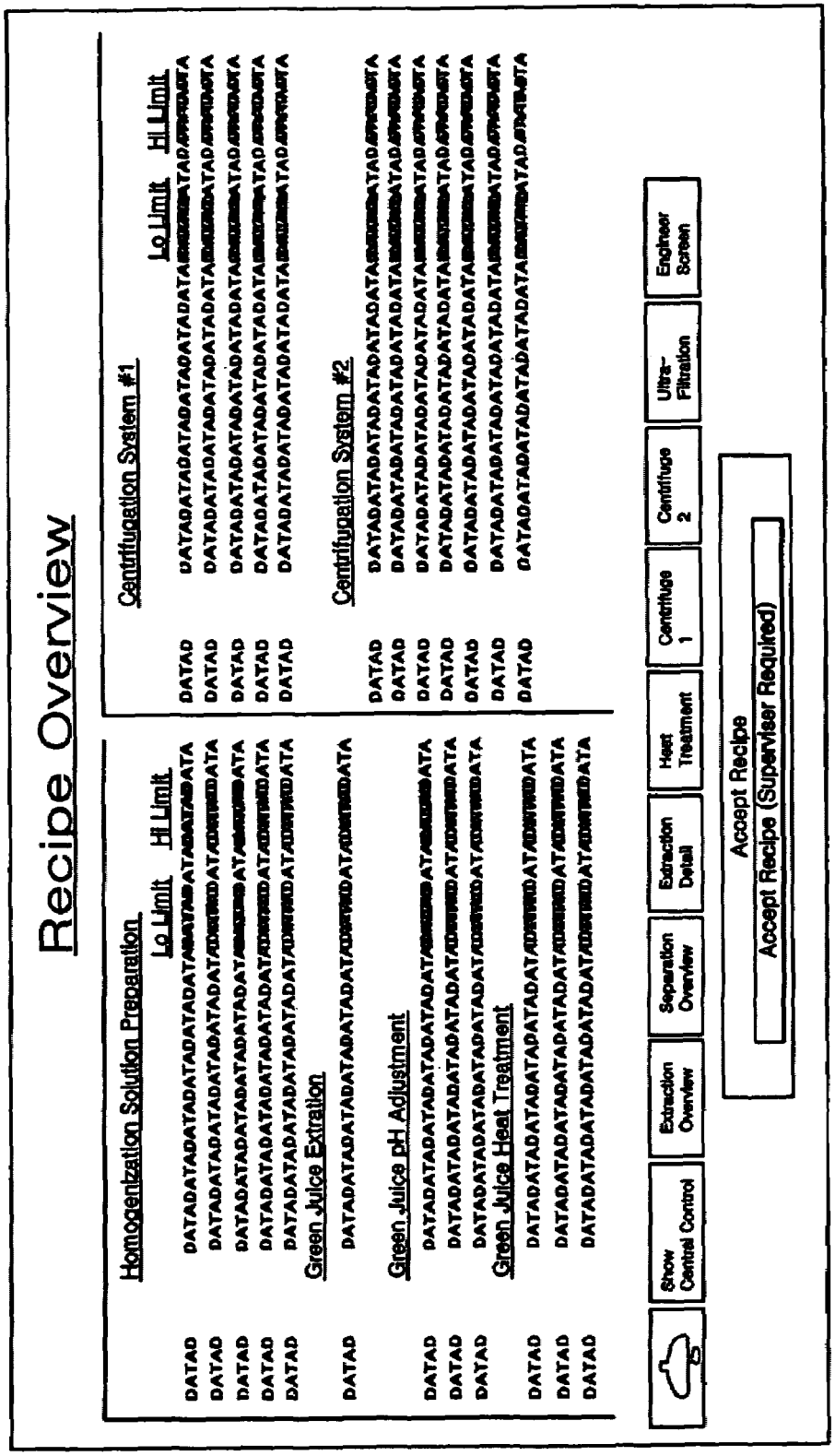
FIG. 23 is a representation of a Recipe Overview screen displayed on the computer depicted in FIG. 19, utilized in the automated control of the automated processing apparatus depicted in FIG. 2, in accordance with the present invention.

In FIG. 21, if the View Recipe button is selected, the RECIPE OVERVIEW screen depicted in FIG. 23 is displayed and an operator can review all of the selected and pre-set parameters currently selected.

In FIG. 23, a range is entered such that if the actual pH determined by the Computer 500 (based on signals from the sensor 102 pH in FIG. 8) is in an unacceptable range, an alarm is triggered (see box 625 in FIG. 20, as described further below) and appropriate action can be taken. Range parameters are predefined and preprogrammed into the computer 500, but may alternatively be entered or altered in an Engineering Screen display (not shown). It should be understood that various levels of access may be programmed into the computer to limit the number of operators able to change or alter settings.

Returning to FIG. 23, the following elements of the automated processing system are displayed: Homogenization Solution Preparation (mixture in tank 101); Green Juice Extraction (operation of the grinder and press apparatus 22); Green Juice pH Adjustment (for adjustment of pH in the tank 102); Green Juice Heat Treatment; Centrifuge System #1; and Centrifuge System #2. Specifically, for each system, the sensors associated with each system are monitored.

Once appropriate parameters are inputted the computer 500 is ready to initiate a start-up procedure where various portions of the automated processing system become operable, as represented by box 605 in FIG. 20. The start-up procedure includes providing power to each of the motors in accordance with the parameters displayed in FIGS. 22 and 23, checking the status of each sensor connected to the computer and processing signals from each sensor.

The computer continuously checks to verify if commands have been inputted by a human operator indicating a change in operations or that the batch is completed, etc., as represented by box 610 in FIG. 20. As is explained in greater detail below, the human operator may input a variety of commands during operation of the automated processing system of the present invention, such as a command indicating completion of the current batch.

Once operation commences, as represented by the box 615 in FIG. 20, the grinder and press apparatus 22 is operated in order to grind and disintegrate bio-matter fed to it via the conveyors 5 and 10. Liquid is provided to the grinder and press apparatus 22 from the tank 101 via pumps 31 and 32 based upon preprogrammed parameters to ensure an adequate bio-matter/liquid ratio, as mentioned previously above. Operation of the pumps 31 and 32 is controlled by the computer 500, but is alternatively manually operated. In an alternate embodiment, weigh belts (not shown) with weight sensors 475 (shown in FIG. 19) are provided on the conveyor 10 to provide mass (weight) data to the computer 500 in order to provide the computer 500 with further information for regulating the flow of liquid into the grinder and press apparatus 22.

Figure 24:
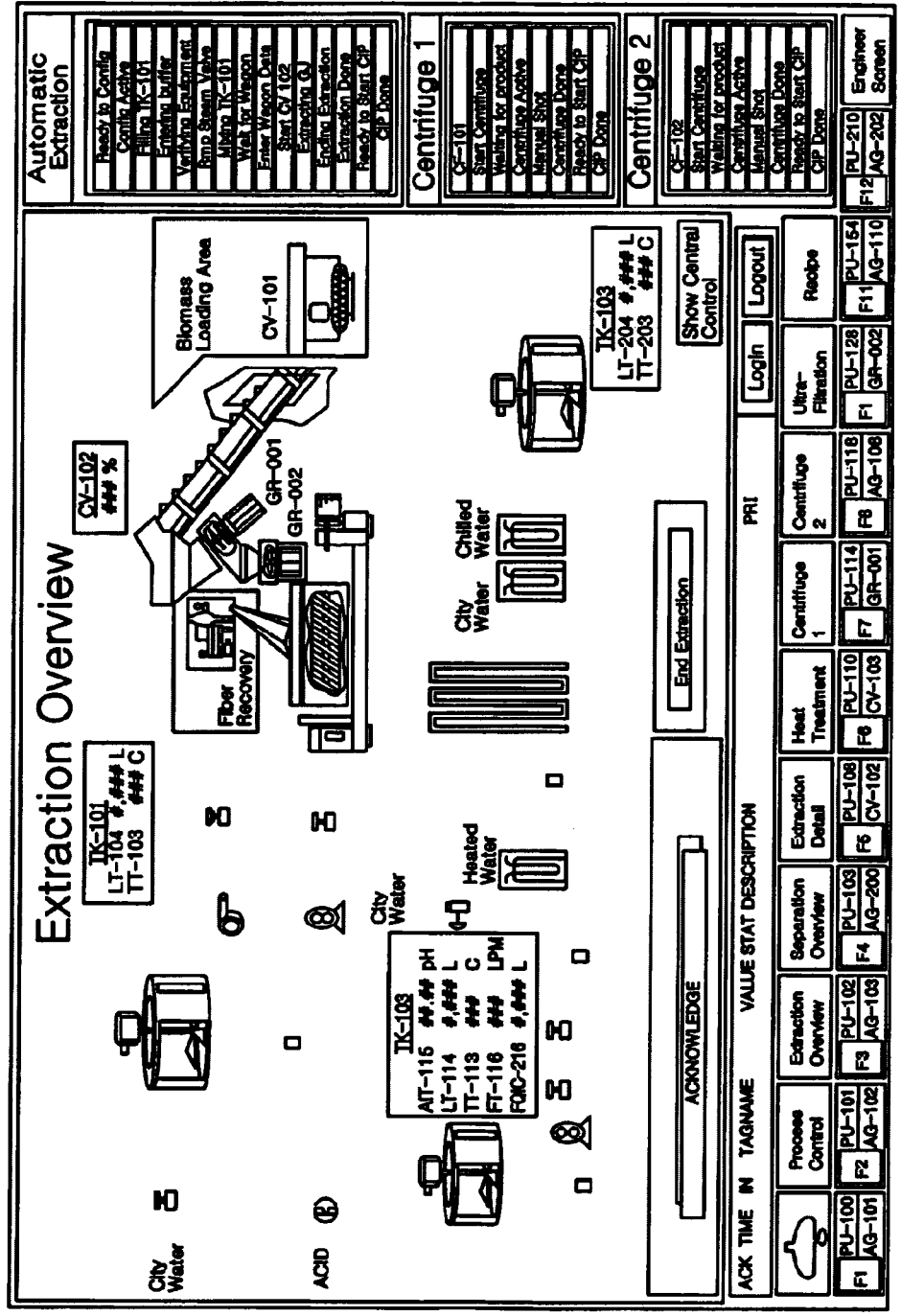
FIG. 24 is a representation of an Extraction Overview screen displayed on the monitor of the computer depicted in FIG. 19, utilized in the automated control of the automated processing apparatus depicted in FIG. 2, in accordance with the present invention.

The status of the operation of the grinder and press apparatus 22 is further displayed on the monitor of the computer 500, as shown in FIG. 24 and described further below after description of the flowchart depicted in FIG. 20.

During operation (box 615 in FIG. 20) the various sensors described above are monitored to ensure that all systems are operating within specified parameters, as represented by box 620 in FIG. 20. In box 625, a decision is made to determine whether or not an alarm has been set due to a sensor reading outside the set parameters. If no alarm has been set, operation returns to box 610. At box 610, a decision is made to determine whether or not the batch is complete.

Returning to box 625 in FIG. 20, if an alarm has been triggered, then appropriate actions are made to restore or amend the batch process, as represented by box 630. It should be understood that the appropriate action depends upon the alarm triggered.

A warning or alarm is triggered for any sensor that indicates a reading outside the pre-determined limits displayed in the screen depicted in FIG. 23. For instance, for the level sensors 102L and 108L in the tanks 102 and 108, respectively, there are four separate levels of concern. During operation of the automated processing apparatus of the present invention, the level sensor 102 pH continuously provides level signals to the computer 500. If the level in the tank 102 is below an alarm level $L_{LA}$, (shown in FIG. 8) then an alarm is triggered by the computer 500 is the step represented by box 630 and operation of the tank 102 is halted (i.e. pH adjuster no is no longer fed into the tank, the agitator stops rotating, and the tank 102 may go to re-circulation mode). If the level in the tank 102 is below a warning level $L_{LW}$ then a warning is indicated on the computer screen or display and in step 630, the appropriate action is taken (for instance, agitator may be set to stop rotating upon warning and tank 102 may be put into re-circulation mode). If the level in the tank 102 is above a high warning level $L_{HW}$ then a warning is indicated on the computer screen or display. In box 630, appropriate action may include slowing down the conveyers to reduce the speed of green juice production, or may merely put warning indication on the computer screen, depending upon pre-determined parameters. If the level in the tank 102 is above an alarm level $L_{HA}$ (shown in FIG. 8) then an alarm is triggered by the computer 500.

In the flowchart depicted in FIG. 20, at box 625, the computer 500 determines whether or not a warning or an alarm has been triggered, alerting an operator of the need for appropriate action or operations. However, for most sensor readings, the computer 500 is programmed to compensate for readings that approach an upper or lower limit.

The computer 500 is programmed to compensate for most sensor fluctuations without triggering a warning or an alarm. For instance, if the pH in the tank 102 approaches a predetermined limit, the flow of pH adjuster is altered accordingly via control of the pump 53. The computer 500 may also determine that the valve $V_1$ must be set to re-circulation mode for the tank 102 in order to allow time for proper pH adjustment or in response to a low level warning signal.

Alarms that may be triggered by the computer 500 include: temperatures that are out of the set limits sensed by any of the plurality of temperature sensors throughout the automated processing system of the present invention; pressure(s) not within preset limits; levels within any of the tanks that are outside the set limits, etc.

Another example of a warning and appropriate action (steps 625 and 630 in FIG. 20) is as follows: if the computer 500 determines in step 625 that a portion of the green juice has been overheated, in step 630 flow of green juice to the heater is stopped by setting the valve $V_1$ to re-circulation mode. Next, water is allowed to flow into the heater via the feed pipe 112 and out of the heater via the waste pipe W, via control of the valves $V_W$ and $V_2$, respectively, shown in FIG. 9.

Yet another example of an alarm and appropriate action is as follows: if the computer 500 determines that the pressure sensor 102P is sending pressure signals above a pre-set value, then the tank 102 goes to re-circulation mode and an alarm is triggered for operator intervention. High pressure readings from the sensor 102P may indicate a blocked pipe in the heater or pipe assembly 90, requiring human intervention.

After appropriate action is taken, a decision is made in box 635 whether to resume or not. If operations are not to be resumed, operation returns to box 630 until all appropriate actions are taken and/or an operator intervenes. If operations are to resume, control returns to box 610. Some alarms trigger an automatic response preprogrammed into the computer 500, and other alarms stop portions of the automated processing apparatus and await input and/or actions by an operator.

At some point in the batch process, operations are completed. For instance, the operator selects the End Batch command in the screen depicted in FIG. 21 causing operations in box 610 to move to the box 640 where a further decision is made for final operations. Final operations include printing a log of the batch process, cleaning the system and/or saving data. If a final operation command is given, operation moves from box 640 to box 645 where, for instance, a log of the batch process printed for record keeping or other required purposes. Thereafter operation control returns to box 640.

The computer 500 is programmed to maintain a log of all events, and parameters of each batch run where a specific bio-matter has been processed to extract a material of interest. All automatic procedures and any human or manual interventions are logged and recorded. For instance, the pH levels maintained in the tanks 102 and 108, the temperature readings from selected temperature sensors, all sensor reading and any other predetermined data are maintained in the computer 500 in memory and saved in the storage-device for archiving purposes. If desired, a report of the logged information is printed out using the printer in FIG. 19.

During regular operation of the automated processing system of the present invention, various screens are displayed on the monitor of the computer 500. FIG. 24 is one of the screens displayed and shows an EXTRACTION OVERVIEW with the grinder and press apparatus 22 (CV-102), the tank 101 (TK-101), the tank 102 (TK-102), the heater 75, the pipe assembly 90, the coolers 96 and 104 and the tank 103 (TK-103) all depicted. For each element above displayed in the screen EXTRACTION OVERVIEW, the sensor readings of each element are displayed as well. For instance, for the grinder and press apparatus 22 the power percentage supplied to the first grinder is displayed in the box CV-102. For the tank 101 the level and temperature of the liquid inside the tank are displayed in the box TK-101. For the tank 102. several sensed parameters are displayed in the box TK-102 as follows: the pH sensed by the sensor 102 pH, the level of green juice sensed by the sensor 102L, the temperature sensed by the senor 102T, the flow of green juice measured by the flow meter 54 and the flow of pH adjuster (acid) via the pump 53 into the tank 102. For the tank 103, the level and temperature of the green juice therein is displayed in the box TK-103. Other parameters of the various sensors, such as temperature sensors, are also displayed but are not shown in FIG. 24 to provide greater clarity.

In the EXTRACTION OVERVIEW screen in FIG. 24, a command button End Extraction is included to stop the grinder and press apparatus 22 if a problem is detected by the operator or if an alarm is triggered by the computer 500. At the bottom of the screen and at the bottom of the each of the screens depicted in FIGS. 25–30, a row of command buttons is provided allowing the operator to view each operation of the automated processing system of the present invention. Specifically, starting from left to right the following buttons when selected display the corresponding screens: the button Process Control displays FIG. 21; the button Extraction Overview displays FIG. 24; the button Separation Overview displays FIG. 25; the button Extraction Detail displays FIG. 26; the button Heat Treatment displays FIG. 27; the button Centrifuge 1 displays FIG. 28, the button Centrifuge 2 displays FIG. 29; the button Ultrafiltration displays FIG. 30; and the button Recipe displays FIG. 22.

Along the right hand side of the monitor screen display in FIG. 24 is an array of command buttons. These same buttons appear in each of the screens depicted in FIGS. 24–30 and appear independent of the remainder of the screen displayed on the monitor of the computer 500. The array of command buttons changes depending upon the mode of operations that was selected in the screen depicted in FIG. 21. For instance, if the Auto (Automatic) mode is selected the buttons at the right of the screen in FIG. 24 are displayed in three groups as follows:

Group I: Automatic Extraction
    Ready to Config
    Config Active
    Recipe Loaded
    Filling TK-101
    Entering Buffer
    Verify Equipment
    Rmp Steam Valve
    Mixing TK-101
    Wait for Wagon
    Enter Wagon Data
    Start CV-102
    Extracting GJ
    Ending Extraction
    Extraction Done
    Ready to Start CIP
    CIP Done
Group II: Centrifuge 1
    CF-101 Off
    Start Centrifuge
    Waiting for Product Centrifuge Active
    Manual Shot
    Centrifuge Done
    Ready to Start CIP
    CIP Done
Group III: Centrifuge 2
    CF-102 Off
    Start Centrifuge
    Waiting for Product
    Centrifuge Active
    Manual Shot
    Centrifuge Done
    Ready to Start CIP
    CIP Done If the Semi-Auto mode in FIG. 21 is selected the buttons at the right of the screens in FIGS. 24–30 are displayed in same three groups of buttons as in the Automatic mode.

If the Maintenance mode in FIG. 21 is selected the buttons at the right of the screens in FIGS. 24–30 are displayed in a single group as follows:

Maintenance
    Solution Preparation
    Green Juice Extr.
    Fiber Removal
    PH Adjustments
    Heat Treatment
    First Centrifuge
    Second Centrifuge
    Ultrafiltration If the CIP (clean in place) mode in FIG. 21 is selected the buttons at the right of the screens in FIGS. 24–30 are displayed in a single group as follows:

CIP
    Extraction System
    Cent. 101
    Cent. 102
    Ultrafiltration
    CIP Done Although the buttons at the right of the screens depicted in FIGS. 24–30 change in accordance with the mode of operation, each of FIGS. 24–30 are shown with only those buttons active in the Automatic mode of operation. However it should be understood that each of the screen displays represented in FIGS. 24–30 change to show the appropriate command buttons in response to selection of an operation mode different from the Automatic mode.

During Automatic mode operation of the automated processing system, the computer 500 automatically manipulates and controls the pumps 53 and 70 and valve $V_1$ in order to adjust and maintain the green juice in the tank 102 at the desired pH level in response to signals from the pH sensor 102 pH, the level sensor 102L and the flow meter 54. Similarly, the computer 500 automatically manipulates and controls the pumps 153 and 138 and valve $V_5$ in order to adjust and maintain the green juice in the tank 108 at the desired pH level in response to signals from the pH sensor 108pH, the level sensor 108L and the flow meter 147. The computer also controls the valve $V_3$, the pump 120 and the operation of the centrifuge 125 in order to separate pellet P1 from supernatant S1. The computer 500 also controls the valve V₅, the pump 153 and the operation of the centrifuge 175 in order to separate waste pellet from supernatant S2. The computer also monitors the temperature of green juice detected by the sensor 205 exiting the heater 75 and manipulates the pump P3 to maintain the temperature of the green juice within the desired temperature range. The computer 500 similarly may control the flow of chilled liquid to the chiller 104 in response to detected temperature readings from the sensor 100 downstream from the chiller 104. Alternatively, the chiller 104 may be operated at full cooling with no set feedback control.

Figure 25:
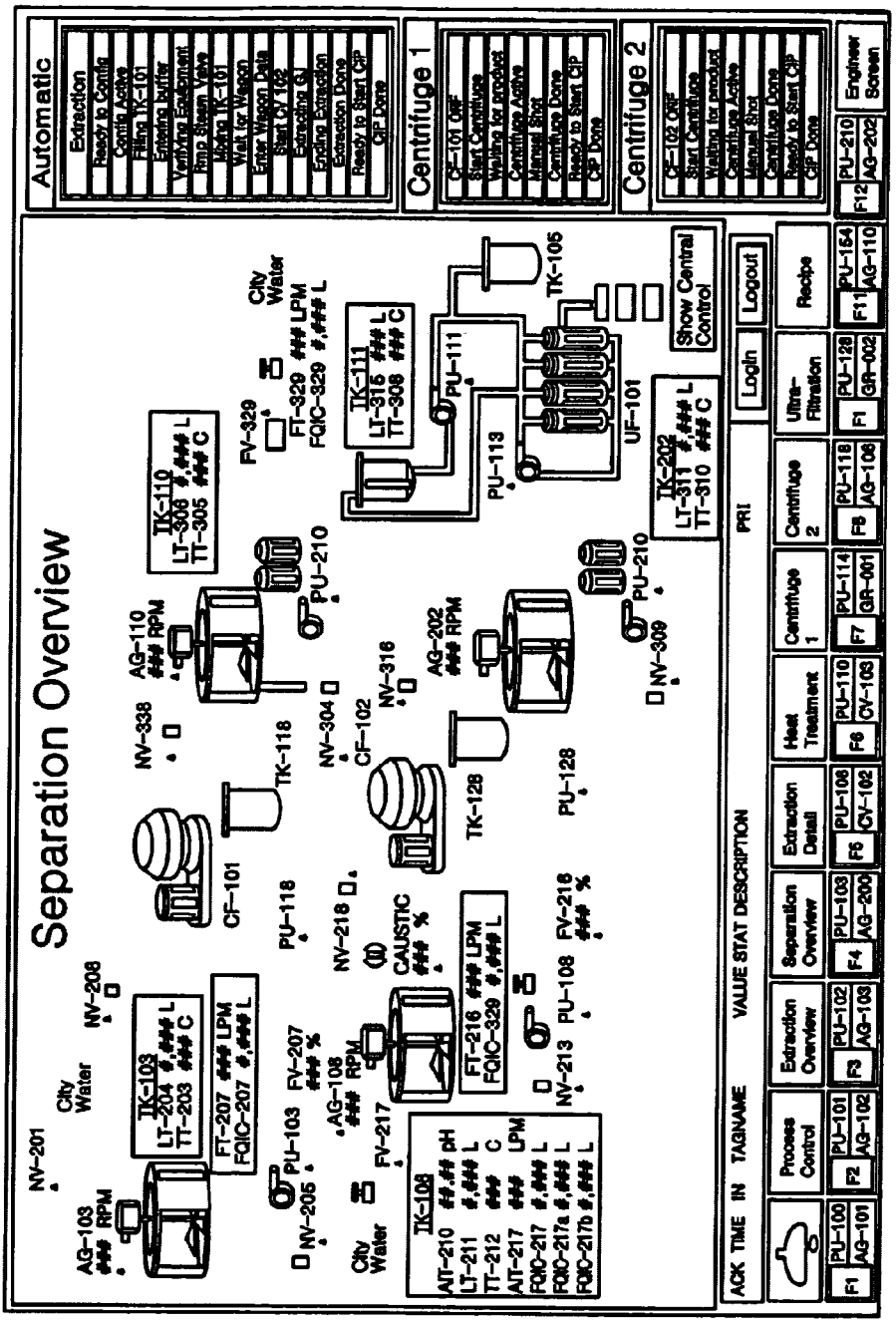
FIG. 25 is a representation of a separation overview screen displayed on the computer depicted in FIG. 19, utilized in the automated control of the automated processing apparatus depicted in FIG. 2, in accordance with the present invention.

FIG. 25 shows a Separation Overview screen display focusing on the separation of pellet P1 from supernatant S1 by the centrifuge 125 (designated in FIG. 25 as CV-101) and further includes the various parameters of the elements of the automated processing apparatus with sensed parameters detected by the corresponding sensors (described above).

Figure 26:
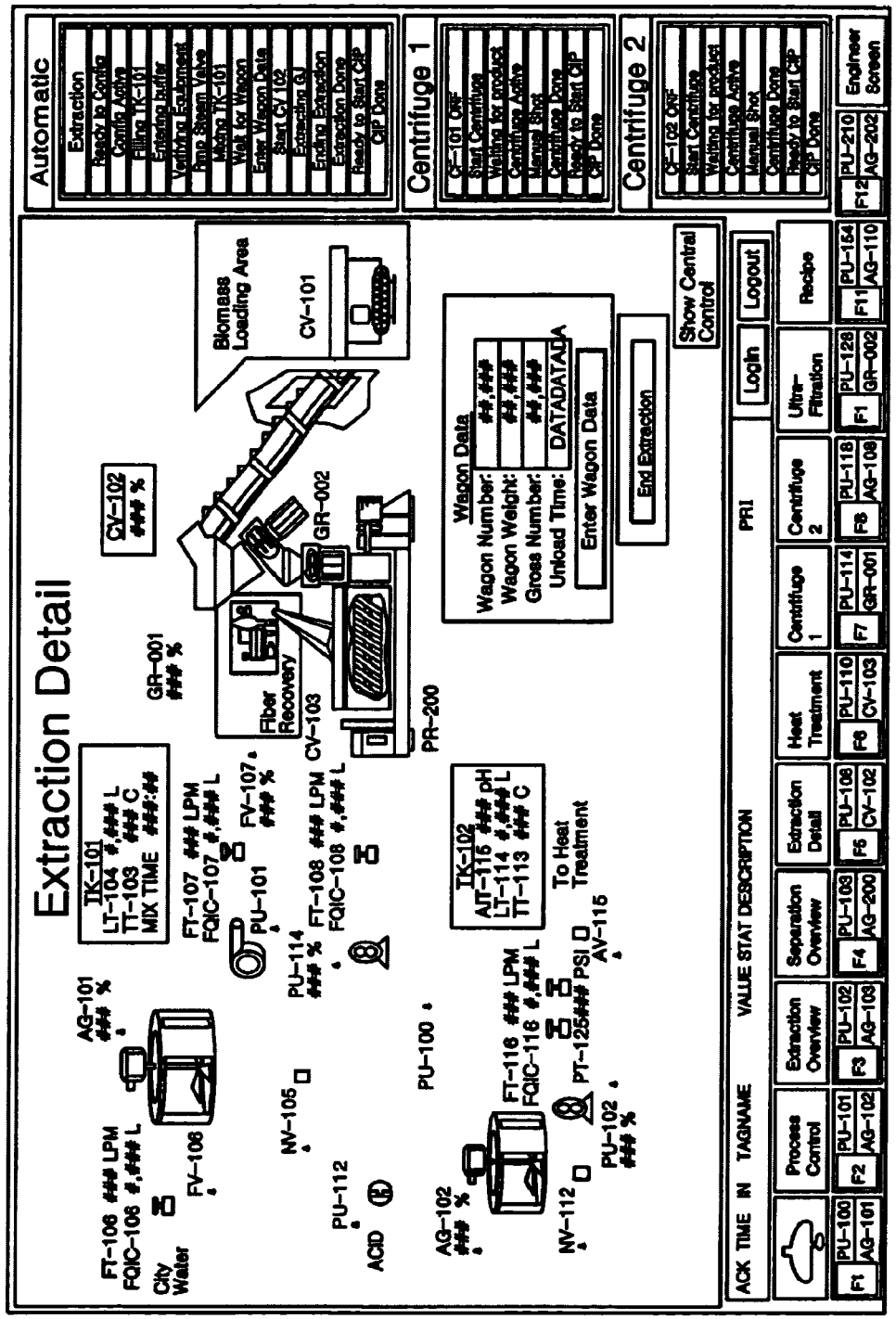
FIG. 26 is a representation of an extraction detail screen displayed on the computer depicted in FIG. 19, utilized in the automated control of the automated processing apparatus depicted in FIG. 2, in accordance with the present invention.

FIG. 26 shows an Extraction Detail screen display focusing on those elements related to the grinder and press apparatus 22 for extraction of the green juice from the bio-matter. Various sensed parameters are displayed on the screen display based upon readings from the above described sensors. Further, an additional window appears in the display for entry of wagon data. Each wagon is identified based upon the harvested material delivered to the conveyor 5 and 10.

Figure 27:
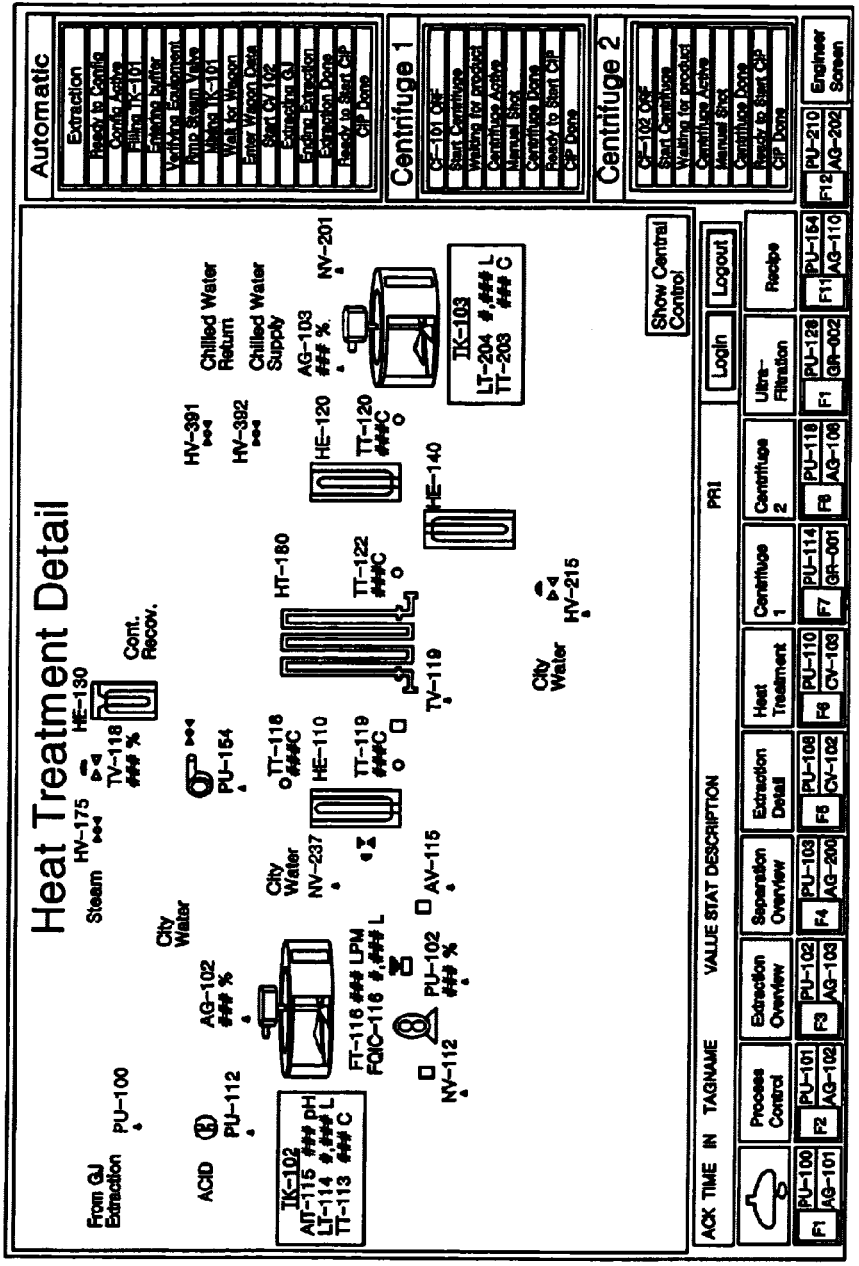
FIG. 27 is a representation of a heat treatment screen displayed on the computer depicted in FIG. 19, utilized in the automated control of the automated processing apparatus depicted in FIG. 2, in accordance with the present invention.

FIG. 27 shows a Heat Treatment Detail screen display where elements such as the heater apparatus 75 are displayed along with related elements and sensed parameters detected by the above described sensors.

Figure 28:
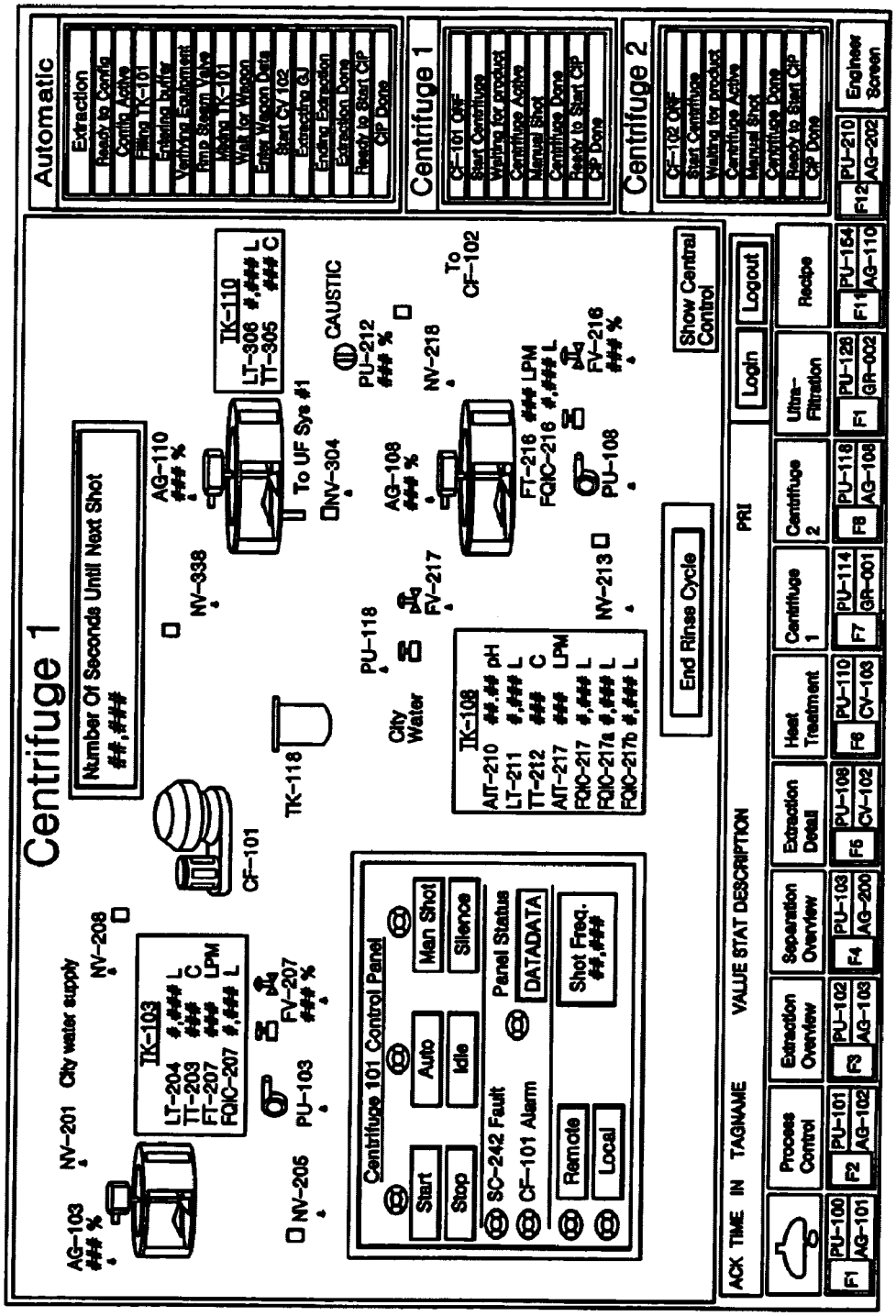
FIG. 28 is a representation of a centrifuge 1 screen displayed on the computer depicted in FIG. 19, utilized in the automated control of the automated processing apparatus depicted in FIG. 2, in accordance with the present invention.

FIG. 28 shows a Centrifuge 1 screen display where the centrifuge 125 (CF-101) is depicted along with the tank 103 (TK-103), tank 110 (TK-110) and tank 108 (TK-108). As with the other screen displays, FIG. 28 also shows sensed parameters detected by the various sensors described above. Further, a command window is included in FIG. 28 with command buttons allowing for manual or automatic control of the centrifuge 125.

FIG. 29 shows a Centrifuge 2 screen display showing the centrifuge 175 (CF-102) with the tank 108 (TK-108) shown along with the tank 202 (TK-202). As with the other screen displays, FIG. 29 also shows sensed parameters detected by the various sensors described above. Further, a command window is included in FIG. 29 with command buttons allowing for manual or automatic control of the centrifuge 175.

FIG. 30 shows an Ultrafiltration System screen display showing the tanks 110 and 202 (TK-110 and TK-202) along with the ultrafiltration system 300. Again, as with the other screen displays, FIG. 30 also shows sensed parameters detected by the various sensors described above.

Via the above described interconnected elements and devices, the computer 500 provides a means for automating an extraction process. Further, the flexible configuration of the grinder and press apparatus 22 provides the capability to process any of a variety of plant materials. The adjustable nature of the pH adjusting features of the tanks 102 and 108 provides the capability to extract any of a variety of materials of interest from bio-matter.

It should be understood that the automated processing apparatus may be modified in any of a variety of ways to further automate the system, or reduce the computer control of the system. For instance, the grinders 20 and 25 and press 35 may alternatively be operated entirely in a manual, on/off manner without computer control. Other components of the system may be operated without computer control. However, for processing operations were record keeping is of importance it is desirable for a computer to maintain records of all phases and portions of the processing operation. Therefore, having each element of the system connected to the computer 500 and at least partially controlled by the computer 500 is advantageous and further ensures reproducibility from processing batch to processing batch.

While several preferred embodiments have been chosen to illustrate the present invention, it will be readily apparent to those skilled in the art from this disclosure that various changes and modifications can be made herein without departing from the scope of the invention as defined in the appended claims. Furthermore, the foregoing description of the embodiments according to the present invention are provided for illustration only, and not for the purpose of limiting the invention as defined by the appended claims and their equivalents.

What is claimed is:

1. An automated bio-matter processing apparatus, comprising:
  a grinder adapted to receive the bio-matter and to extract juice from the bio-matter;
  a juice pH monitoring and adjustment system located downstream of the grinder to receive the juice from the grinder and to monitor and adjust pH of the juice;
  a heater located downstream of the juice pH monitoring and adjustment system to receive pH adjusted juice and to heat the pH adjusted juice to a first temperature for a first length of time;
  a centrifuge located downstream of the heater to receive heated pH adjusted juice and to separate the heated pH adjusted juice into a pellet stream and a supernatant stream;
  said grinder, said juice pH monitoring and adjustment system, said heater and said centrifuge being connected together for continuous processing of said bio-matter; and
  a computerized control system communicated with the grinder, the juice pH monitorizing and adjustment system, the heater and the centrifuge, so that the control system monitors and controls the automated processing apparatus.

2. An automated bio-matter processing apparatus, comprising:
  a grinder adapted to receive the bio-matter and to extract juice from the bio-matter;
  a juice pH monitoring and adjustment system located downstream of the grinder to receive the juice from the grinder and to monitor and adjust pH of the juice;
  a heater located downstream of the juice pH monitoring and adjustment system to receive pH adjusted juice and to heat the pH adjusted juice to a first temperature for a first length of time;
  a centrifuge located downstream of the heater to receive heated pH adjusted juice and to separate the heated pH adjusted juice into a pellet stream and a supernatant stream;
  a computerized control system communicated with the grinder, the juice pH monitorizing and adjustment system, the heater and the centrifuge, so that the control system monitors and controls the automated processing apparatus; and
  a filtering system located downstream of the supernatant stream from the centrifuge to filter the supernatant stream.

3. The apparatus of claim 2, wherein the filtering system comprises:
  at least one first filter; and
  a separate ultrafiltration system.

4. An automated bio-matter processing apparatus, comprising:
- a grinder adapted to receive the bio-matter and to extract juice from the bio-matter;
- a juice pH monitoring and adjustment system located downstream of the grinder to receive the juice from the grinder and to monitor and adjust pH of the juice;
- a heater located downstream of the juice pH monitoring and adjustment system to receive pH adjusted juice and to heat the pH adjusted juice to a first temperature for a first length of time;
- a centrifuge located downstream of the heater to receive heated pH adjusted juice and to separate the heated pH adjusted juice into a pellet stream and a supernatant stream;
- a computerized control system communicated with the grinder, the juice pH monitorizing and adjustment system, the heater and the centrifuge, so that the control system monitors and controls the automated processing apparatus;
- a resuspension tank located downstream of the pellet stream from the centrifuge;
- a pellet stream pH monitoring and adjustment system located downstream of the resuspension tank; and
- a second centrifuge located downstream of the pellet stream pH monitoring adjustment system.

5. The apparatus of claim 1, wherein the grinder comprises:
- a first cutter, including blades to cut leafy material;
- a second cutter, including blades to cut leafy material; and
- a press.

6. The apparatus of claim 1, wherein the heater comprises:
- a flexible length piping apparatus including a pipe capable of having fluid flowing therethrough.

* * * * *